(12) United States Patent
Deliencourt-Godefroy et al.

(10) Patent No.: US 9,434,670 B2
(45) Date of Patent: Sep. 6, 2016

(54) FAMILY OF ARYL, HETEROARYL, O-ARYL AND O-HETEROARYL CARBASUGARS

(75) Inventors: Geraldine Deliencourt-Godefroy, Bois d'Ennebourg (FR); Lenaig Lopes, Le Petit Quevilly (FR)

(73) Assignee: TFCHEM, Val de Reuil (FR)

( * ) Notice: Subject to any disclaimer, the term of this patent is extended or adjusted under 35 U.S.C. 154(b) by 0 days.

(21) Appl. No.: 14/119,265

(22) PCT Filed: May 29, 2012

(86) PCT No.: PCT/EP2012/060050
§ 371 (c)(1),
(2), (4) Date: Nov. 21, 2013

(87) PCT Pub. No.: WO2012/160218
PCT Pub. Date: Nov. 29, 2012

(65) Prior Publication Data
US 2014/0105839 A1 Apr. 17, 2014

(30) Foreign Application Priority Data
May 26, 2011 (EP) .................................... 11305645

(51) Int. Cl.
| | | |
|---|---|---|
| C07C 43/29 | (2006.01) |
| A61K 31/085 | (2006.01) |
| C07C 43/225 | (2006.01) |
| C07C 43/23 | (2006.01) |
| C07C 43/247 | (2006.01) |
| C07C 43/253 | (2006.01) |
| C07D 231/20 | (2006.01) |
| C07D 333/16 | (2006.01) |
| A61K 8/34 | (2006.01) |
| A61K 8/49 | (2006.01) |
| A61Q 19/02 | (2006.01) |
| C07C 41/09 | (2006.01) |
| C07C 41/22 | (2006.01) |
| C07C 41/24 | (2006.01) |

(52) U.S. Cl.
CPC .............. *C07C 43/29* (2013.01); *A61K 8/347* (2013.01); *A61K 8/494* (2013.01); *A61K 8/4986* (2013.01); *A61Q 19/02* (2013.01); *C07C 41/09* (2013.01); *C07C 41/22* (2013.01); *C07C 41/24* (2013.01); *C07C 43/225* (2013.01); *C07C 43/23* (2013.01); *C07C 43/247* (2013.01); *C07C 43/253* (2013.01); *C07D 231/20* (2013.01); *C07D 333/16* (2013.01)

(58) Field of Classification Search
CPC ............................ C07C 43/225; C07C 43/23
See application file for complete search history.

(56) References Cited

U.S. PATENT DOCUMENTS
2010/0167989 A1 7/2010 Gant

FOREIGN PATENT DOCUMENTS
| | | | |
|---|---|---|---|
| WO | WO 2005/044256 A1 | 5/2005 |
| WO | WO 2008/070609 A1 | 6/2008 |
| WO | WO 2009/076550 A1 | 6/2009 |

OTHER PUBLICATIONS

International Search Report issued in application No. PCT/EP2012/060050 on Jul. 16, 2012.
Arakawa et al., "Improved diabetic syndrome in C57BL/KsJ-db/db mice by oral administration of the Na+-glucose cotransporter inhibitor T-1095," British Journal of Pharmacology, 2001, vol. 132, pp. 578-586.
Chao et al., SGLT2 inhibition—a novel strategy for diabetes treatment, Nature Reviews, Jul. 2010, vol. 9, pp. 551-559.
Chao, "A Paradigm Shift in Diabetes Therapy—Dapagliflozin and Other SGLT2 Inhibitors," Discovery Medicine, Mar. 2011, vol. 11, No. 58, pp. 255-263.
Cumpstey, "Short synthesis of a benzyl ether protected building block for the synthesis of carbocyclic galactopyranose mimics," Carbohydrate Research, 2010, vol. 345, pp. 1056-1060.
Dookhun et al., "Synthesis and biological evaluation of a bicyclo[4.1.0]heptyl analogue of glucose-1-phosphate," Can. J. Chem., 2004, vol. 82, pp. 1361-1364.
Greene et al., "Protective Groups in Organic Synthesis," copyright 1991 by John Wiley & Sons, Inc., 12 pages.

(Continued)

*Primary Examiner* — Jessica Worsham
(74) *Attorney, Agent, or Firm* — Foley & Lardner LLP

(57) ABSTRACT

The present invention relates to a compound of the following formula (I): as well as its process of preparation, pharmaceutical and cosmetics composition comprising it and use thereof, notably as an inhibitor of the sodium-dependent glucose co-transporter, such as SGLT1, SGLT2 and SGLT3, in particular in the treatment or prevention of diabetes, and more particularly type-II diabetes, diabetes-related complications, such as arthritis of the lower extremities, cardiac infarction, renal insufficiency, neuropathy or blindness, hyperglycemia, hyperinsulinemia, obesity, hypertriglyceridemia, X syndrome and arteriosclerosis, as well as for its use as an anticancer, anti-infective, anti-viral, anti-thrombotic or anti-inflammatory drug, or for lightening, bleaching, depigmenting the skin, removing blemishes from the skin, particularly age spots and freckles, or preventing pigmentation of the skin.

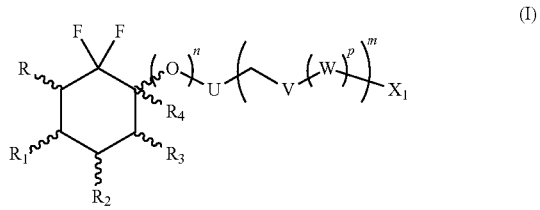

16 Claims, 8 Drawing Sheets

(56) References Cited

OTHER PUBLICATIONS

Ismail et al., "β-Glycosidase Activity toward Different Glycosidic Forms of Isoflavones," J. Agric. Food Chem., 2005, vol. 53, pp. 4918-4924.

Johannsson et al., "Growth Hormone Treatment of Abdominally Obese Men Reduces Abdominal Fat Mass, Improves Glucose and Lipoprotein Metabolism, and Reduces Diastolic Blood Pressure," Journal of Clinical Endocrinology and Metabolism, 1997, vol. 82, No. 3, pp. 727-734.

Kahn et al., "Normalization of Blood Glucose in Diabetic Rats with Phlorizin Treatment Reverses Insulin-resistant Glucose Transport in Adipose Cells without Restoring Glucose Transporter Gene Expression," Journal of Clinical Investigation, Feb. 1991, vol. 87, pp. 561-570.

Meng et al., "Discovery of Dapagliflozin: A Potent, Selective Renal Sodium-Dependent Glucose Cotransporter 2 (SGLT2) Inhibitor for the Treatment of Type 2 Diabetes," Journal of Medicinal Chemistry, 2008, vol. 51, pp. 1145-1149.

Rossetti et al., "Correction of Hyperglycemia with Phlorizin Normalizes Tissue Sensitivity to Insulin in Diabetic Rats," Journal of Clinical Investigation, May 1987, vol. 79, pp. 1510-1515.

Rossetti et al., "Effect of Chronic Hyperglycemia on In Vivo Insulin Secretion in Partially Pancreatectomized Rats," Journal of Clinical Investigation, Oct. 1987, vol. 80, pp. 1037-1044.

Tsujihara et al., "$Na^+$-Glucose Cotransporter (SGLT) Inhibitors as Antidiabetic Agents. 4. Synthesis and Pharmacological Properties of 4'-Dehydroxyphlorizin Derivatives Substituted on the B Ring," J. Med. Chem., 1999, vol. 42, pp. 5311-5324.

FAMILY OF ARYL, HETEROARYL, O-ARYL AND O-HETEROARYL CARBASUGARS

This invention relates to a family of fluorinated aryl, heteroaryl, O-aryl and O-heteroaryl glycoside compounds, the process for their preparation, as well as the application of same in the pharmaceutical or cosmetic fields, in particular for the treatment or prevention of diabetes and obesity, and as depigmenting or lightening agent.

Sugars and the derivatives thereof constitute one of the most common classes of compounds in nature. Based on their chemical structures, they exhibit various physico-chemical properties and can play a key role in a wide variety of biological processes.

In recent years, there has been a growing interest in discovering new glycosides having advantageous properties in terms of improved efficacy, selectivity and stability.

Found among these compounds, in particular, are aryl glycosides or phenol glycosides having applications in the field of cosmetics or in the treatment or prevention of diseases such as diabetes, obesity, cancer, inflammatory diseases, auto-immune diseases, infections, thromboses, and with regard to numerous other therapeutic fields. By their biological properties and their structure, these compounds interest numerous research teams.

Phlorizin may be cited in particular, as a molecule known for its inhibiting activity with regard to sodium-dependent glucose co-transporters (SGLT) (Journal of Clinical Investigation, vol. 79, p. 1510, (1987); ibid., vol. 80, p. 1037 (1987); ibid., vol. 87, p. 561 (1991); J. of Med. Chem., vol. 42, p. 5311 (1999); British Journal of Pharmacology, vol. 132, p. 578, (2001)).

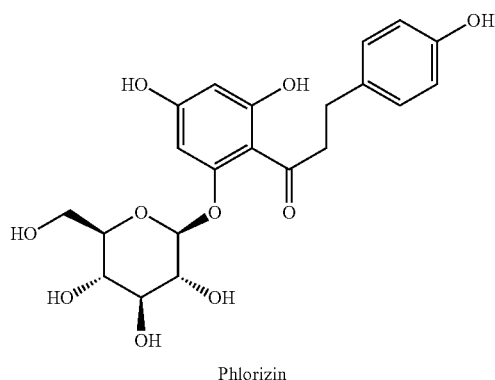

Phlorizin

Inhibitors of sodium-dependent glucose co-transporters (SGLT), found in particular in the intestines and kidney, are potentially usable for treating diabetes, and more specifically type-II diabetes, but also for hyperglycemia, hyperinsulinemia, obesity, hypertriglyceridemia, syndrome X (also known by the name of metabolic syndrome, J. of Clin. Endocrinol. Metabol., 82, 727-734 (1997)), diabetes-related complications or else atherosclerosis. As a matter of fact, it is known that hyperglycemia participates in the onset and evolution of diabetes and leads to a reduction in the secretion of insulin and a reduction in insulin sensitivity, which results in an increase in the glucose level, thereby exacerbating diabetes. The treatment of hyperglycemia can thus be considered as a mean to treat diabetes.

Such being the case, one of the methods for treating hyperglycemia is to promote the excretion of excess of glucose directly into the urine, e.g., by inhibiting the sodium-dependent glucose co-transporter in the proximal tubules of the kidneys, the effect of which is to inhibit the re-absorption of glucose and to thereby promote the excretion thereof into the urine, leading thus to a reduction in the blood-sugar level.

At present, a large number of drugs exist, which can be used for treating diabetes, such as biguanides, sulfonylureas, insulin resistance-improving agents, and inhibitors of α-glycosidases. However, these compounds have numerous side effects, thereby increasing the need for new drugs.

Therefore, the invention provides new compounds, which are useful, in particular, for the treatment or prevention of diabetes and obesity.

These compounds are $CF_2$-analogues of aryl, heteroaryl, O-aryl, O-heteroaryl glycosides, wherein the intracyclic glycosidic oxygen is replaced by a carbon atom, carrying two fluorine atoms. These compounds will have the distinctive feature of being stable analogues of O-aryl and O-heteroaryl glycosides, when confronted with enzymatic degradation processes, in particular via glycosidase-type enzymes. Moreover, difluorinated carbon is a good mimic of the oxygen atom.

Stable aryl-glycoside analogues, wherein it is the anomeric oxygen which is replaced by a carbon atom carrying two fluorine atoms, are described in the patent application WO 2009/121 939.

The synthesis of O-aryl glycosides wherein the intracyclic or anomeric oxygen is replaced by a carbon atom, carrying two fluorine atoms is described in the patent applications WO 2005/044 256. The synthesis of the following compound is notably described:

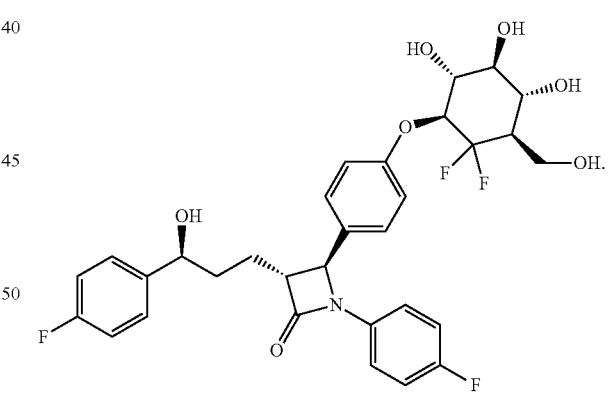

O-aryl and aryl analogues wherein the endocyclic oxygen is replaced by a carbon atom carrying two halogen atoms have also been reported in WO 2009/076 550 but have not been exemplified.

The inventors have thus developed new synthetic approaches enabling access to new aryl, heteroaryl, O-aryl and O-hetero-aryl compounds, useful as SGLT inhibitors, in particular for the treatment or prevention of diabetes and obesity, and useful as Tyrosinase inhibitors, notably for cosmetic applications and especially as depigmenting or lightening agents and also as antioxydants.

Therefore, the present invention relates to a compound having the following formula (I):

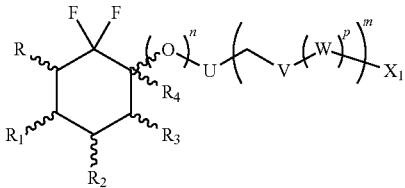

or a pharmaceutically or cosmetically acceptable salt thereof, a tautomer, a stereoisomer or a mixture of stereoisomers in any proportion, in particular a mixture of enantiomers, and particularly a racemate mixture,
wherein:
n, m and p represent, independently from one another, 0 or 1,
R represents a hydrogen or a fluorine atom or a $CH_3$, $CH_2F$, $CH_2OH$, $CH_2OSiR^aR^bR^c$, $CH_2OR^{11}$, $CH_2OCOR^{11}$, $CH_2OCO_2R^{11}$, $CH_2OCONR^{12}R^{13}$, $CH_2OP(O)(OR^{14})_2$ or $CH_2OSO_3R^{14}$ group,
$R_1$ and $R_2$ represent, independently from one another, a fluorine atom or an OH, $OSiR^dR^eR^f$, $OR^{15}$, $OCOR^{15}$, $OCO_2R^{15}$ or $OCONR^{16}R^{17}$ group,
$R_3$ represents a hydrogen or fluorine atom or an OH, $OSiR^gR^hR^i$, $OR^{18}$, $OCOR^{18}$, $OCO_2R^{18}$, $OCONR^{19}R^{20}$, $NR^{19}R^{20}$ or $NR^{19}COR^{18}$ group,
$R_4$ represents a hydrogen atom when n=1, and $R_4$ represents a hydrogen atom, an halogen atom or an OH, $OSiR^jR^kR^l$, $OR^{21}$, $OCOR^{21}$, $OCO_2R^{21}$, or $OCONR^{22}R^{23}$ group when n=0,
or R and $R_1$, together with the carbon atoms carrying them, form a cyclic acetal having the following formula:

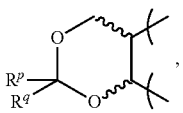

and/or ($R_1$ and $R_2$), ($R_2$ and $R_3$), and/or ($R_3$ and $R_4$), together with the carbon atoms carrying them, form a cyclic acetal having the following formula:

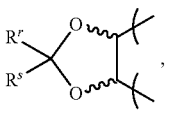

and
$X_1$ represents a hydrogen atom, an halogen atom, a CN, OH, $SO_2$, $SiR'''R''R^o$, $(C_1-C_6)$-alkyl, $(C_2-C_6)$-alkenyl, $(C_2-C_6)$-alkynyl, $(C_3-C_7)$-cycloalkyl, $OR^{24}$, $COR^{24}$, $OCOR^{24}$, $CO_2R^{24}$, $NR^{25}R^{26}$, $NR^{25}COR^{24}$, $CONR^{25}R^{26}$, $SR^{24}$, $SO_2R^{24}$, $CSR^{24}$ or $OSO_3R^{24}$ group, and
U, V and W represent, independently from one another, a phenyl, pyrazolyl, N—$(C_1-C_6)$alkyl-pyrazolyl, or thienyl ring,
the said ring being optionally substituted with one or more substituents selected from the group consisting of an halogen atom, a CN, OH, $SO_2$, $SiR'''R''R^o$, $(C_1-C_6)$-alkyl, $(C_2-C_6)$-alkenyl, $(C_2-C_6)$-alkynyl, $(C_3-C_7)$-cycloalkyl, $OR^{24}$, $COR^{24}$, $OCOR^{24}$, $CO_2R^{24}$, $NR^{25}R^{26}$, $NR^{25}COR^{24}$, $CONR^{25}R^{26}$, $SR^{24}$, $SO_2R^{24}$, and $OSO_3R^{24}$ group,
with:
$R^{11}$, $R^{15}$, $R^{18}$, $R^{21}$ and $R^{24}$ representing, independently from one another, a $(C_1-C_6)$-alkyl, $(C_2-C_6)$-alkenyl, $(C_2-C_6)$-alkynyl, $(C_3-C_7)$-cycloalkyl, 5 to 7 ring-membered heterocycloalkyl, aryl, aryl-$(C_1-C_6)$-alkyl or $(C_1-C_6)$-alkyl-aryl group, this group being possibly substituted by one or more groups chosen among an halogen atom, an OH, COOH and CHO group,
$R^{12}$, $R^{13}$, $R^{16}$, $R^{17}$, $R^{19}$, $R^{20}$, $R^{22}$, $R^{23}$, $R^{25}$ and $R^{26}$ representing, independently from one another, a hydrogen atom or a $(C_1-C_6)$-alkyl or aryl-$(C_1-C_6)$-alkyl group,
$R^{14}$ representing a hydrogen atom or a $(C_1-C_6)$-alkyl group,
$R^a$ to $R^o$ representing, independently from one another, a $(C_1-C_6)$-alkyl, aryl or aryl-$(C_1-C_6)$-alkyl group, and
$R^p$ to $R^s$ representing, independently from one another, a hydrogen atom, a $(C_1-C_6)$-alkyl group, aryl or aryl-$(C_1-C_6)$-alkyl group.

In this invention, "pharmaceutically or cosmetically acceptable" is understood to mean what is useful in the preparation of a pharmaceutical or cosmetic composition which is generally safe, non-toxic and neither biologically nor otherwise undesirable and which is acceptable for veterinary and human pharmaceutical use, as well as cosmetic use.

In this invention, "pharmaceutically or cosmetically acceptable salts" of a compound, is understood to designate salts which are pharmaceutically or cosmetically acceptable, as defined herein, and which possess the desired pharmacological activity of the parent compound. Such salts include:

(1) hydrates and solvates, such as (S)-propylene glycol solvate, (2) acid addition salts formed with inorganic acids such as hydrochloric acid, bromhydric acid, sulphuric acid, nitric acid, phosphoric acid or the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, mandelic acid, methanesulfonic acid, muconic acid, 2-naphtalenesulfonic acid, propionic acid, salicylic acid, succinic acid, dibenzoyl-L-tartaric acid, tartaric acid, p-toluenesulfonic acid, trimethylacetic acid, trifluoroacetic acid and the like; and (3) salts formed when an acid proton present in the parent compound is either replaced by a metal ion, e.g., an alkali metal ion (e.g., $Na^+$, $K^+$ or $Li^+$), an alkaline-earth metal ion (like $Ca^{2+}$ or $Mg^{2+}$) or an aluminium ion; or coordinates with an organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide.

In this invention, "tautomer" is understood to designate an isomer obtained by prototropy, i.e. migration of a hydrogen atom and change of localisation of a double bond. The different tautomers of a compound are generally interconvertible and present in equilibrium in solution, in various proportions which can depend on the solvent used, on the temperature or on the pH.

In this invention, "stereoisomers" mean isomers having the same molecular formula and sequence of bonded atoms but which differ in the three-dimensional orientations of their atoms in space. They designate thus E/Z isomers, diastereoisomers and enantiomers. E/Z isomers are compounds having a double bond, the substituents present on this double bond being not on the same side of the double bond. Stereoisomers which are not mirror images of one another are thus designated as "diastereoisomers", and stereoisomers which are non-superimposable mirror images are designated as "enantiomers".

Notably, the sugar moiety of the compounds of the invention can belong to the D or L series, and preferably to the D series.

A carbon atom bound to four non-identical substituents is called a "chiral centre".

An equimolar mixture of two enantiomers is called a racemate mixture.

Within the meaning of this invention, "halogen" is understood to mean an atom of fluorine, bromine, chlorine or iodine.

Within the meaning of this invention, "$(C_1-C_6)$-alkyl" group is understood to mean a saturated, linear or branched hydrocarbon chain comprising from 1 to 6 carbon atoms, in particular the methyl, ethyl, n-propyl, isopropyl, n-butyl, iso-butyl, sec-butyl, tert-butyl, n-pentyl, n-hexyl groups.

Within the meaning of this invention, "$(C_2-C_6)$-alkenyl" group is understood to mean a linear or branched hydrocarbon chain comprising at least one double bond and comprising from 2 to 6 carbon atoms, e.g., such as an ethenyl (vinyl) or propenyl group.

Within the meaning of the invention, "$(C_2-C_6)$-alkynyl" group is understood to mean a linear or branched hydrocarbon chain comprising at least one triple bond and comprising from 2 to 6 carbon atoms, e.g., such as an ethynyl or propynyl group.

Within the meaning of this invention, "$(C_3-C_7)$-cycloalkyl" group is understood to mean a saturated hydrocarbon ring comprising from 3 to 7, advantageously from 5 to 7, carbon atoms, in particular the cyclohexyl, cyclopentyl or cycloheptyl group.

Within the meaning of this invention, "5 to 7 ring-membered heterocycloalkyl" group is understood to mean a saturated hydrocarbon ring having 5 to 7 members and containing one or more, advantageously one or two, heteroatoms in place of the carbon atoms, e.g., such as sulphur, nitrogen or oxygen atoms, e.g., such as the tetrahydrofuranyl, piperidinyl, pyrrolidinyl, tetrahydropyranyl, 1,3-dioxolanyl group.

Within the meaning of this invention, "aryl" group is understood to mean a hydrocarbon aromatic group preferably comprising from 5 to 10 carbon atoms and including one or more fused rings, e.g., such as a phenyl or naphtyl group. This is advantageously phenyl.

Within the meaning of this invention, "aryl-$(C_1-C_6)$-alkyl" group is understood to mean any aryl group as defined above, which is bound to the molecule by means of a $(C_1-C_6)$-alkyl group as defined above. In particular, a group such as this can be a benzyl group.

Within the meaning of this invention, "$(C_1-C_6)$-alkyl-aryl" group is understood to mean a $(C_1-C_6)$-alkyl group as defined above, which is bound to the molecule by means of an aryl group as defined above. In particular, a group such as this can be a methylphenyl group.

Within the meaning of this invention, "N—$(C_1-C_6)$alkyl-pyrazolyl" group is a group of the following formula, wherein X represents a $(C_1-C_6)$alkyl group as defined above:

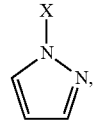

this group being bound to the rest of the molecule by two of the carbon atoms of the pyrazolyl moiety.

The compounds of the invention are advantageously based on the following formulas (Ia), (Ib) and (Ic), and in particular (Ia) and (Ic):

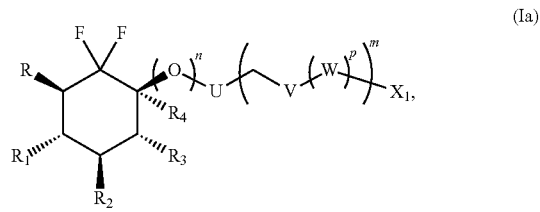
(Ia)

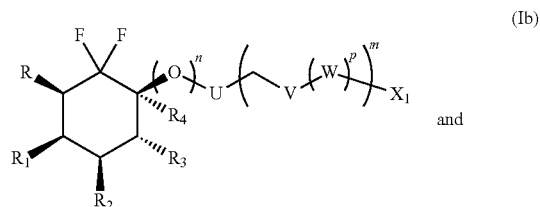
(Ib)

and

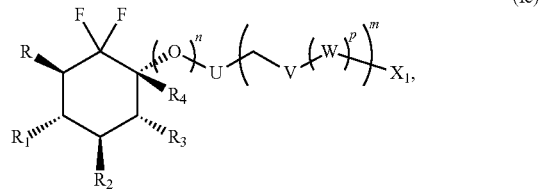
(Ic)

with R, $R_1$, $R_2$, $R_3$, $R_4$, $X_1$, U, V, W, n, m and p as defined above.

Advantageously, $R_1$ and $R_2$ represent, independently from one another, a fluorine atom or an OH, $OSiR^dR^eR^f$, $OR^{15}$, $OCOR^{15}$, $OCO_2R^{15}$ or $OCONR^{16}R^{17}$ group and $R_3$ represents a fluorine atom or an OH, $OSiR^gR^hR^i$, $OR^{18}$, $OCOR^{18}$, $OCO_2R^{18}$ or $OCONR^{19}R^{20}$ group.

More advantageously, $R_1$ and $R_2$ represent, independently from one another, an OH, $OR^{15}$ or $OCOR^{15}$ group and $R_3$ represents an OH, $OR^{18}$ or $OCOR^{18}$ group.

Even more advantageously, $R_1$, $R_2$ and $R_3$ may be chosen, independently from one another, among an OH, —O—$(C_1-C_6)$-alkyl, —O-aryl, —O—$(C_1-C_6)$-alkyl-aryl and —OCO—$(C_1-C_6)$-alkyl group.

In particular, $R_1$, $R_2$ and $R_3$ may be chosen, independently from one another, among an OH, $OSiMe_3$ and benzyloxy (OBn) group, and preferably among OH and OBn.

According to a particular embodiment, $R_1$, $R_2$ and $R_3$ are identical.

According to another particular embodiment, $R_1$, $R_2$ and $R_3$ are identical and represent each an OH group and R represents a $CH_2OH$ group.

R advantageously represents a hydrogen atom or a $CH_3$, $CH_2OH$, $CH_2OR^{11}$, $CH_2OSiR^aR^bR^c$, $CH_2OCOR^{11}$, $CH_2OP$ (O)(OH)$_2$ or CH$_2$OSO$_3$H group, and in particular a hydrogen atom or a CH$_3$, CH$_2$OH, CH$_2$OR$^{11}$, CH$_2$OCOR$^{11}$, CH$_2$OP(O)(OH)$_2$ or CH$_2$OSO$_3$H group, with R$^a$, R$^b$, R$^c$ and R$^{11}$ as defined above, and with CH$_2$OR$^{11}$ advantageously representing a —CH$_2$O—(C$_1$-C$_6$)-alkyl, —CH$_2$O-aryl and —CH$_2$O—(C$_1$-C$_6$)-alkyl-aryl, and CH$_2$OCOR$^{11}$ group, more advantageously representing a —CH$_2$OCO—(C$_1$-C$_6$)-alkyl group.

Even more advantageously, R represents a CH$_2$OH, CH$_2$OSiR$^a$R$^b$R$^c$, CH$_2$OR$^{11}$ or CH$_2$OCOR$^{11}$ group, and more advantageously a CH$_2$OH, CH$_2$OR$^{11}$ or CH$_2$OCOR$^{11}$ group, with R$^a$, R$^b$, R$^c$ and R$^{11}$ as defined above.

Yet even more advantageously, R represents a CH$_2$OH, —CH$_2$O—(C$_1$-C$_6$)-alkyl, —CH$_2$O-aryl, —CH$_2$O—(C$_1$-C$_6$)-alkyl-aryl and —CH$_2$OCO—(C$_1$-C$_6$)-alkyl group.

In particular, R can represent a CH$_2$OH, CH$_2$OSiMe$_3$ or CH$_2$OBn group, and preferably a CH$_2$OH or CH$_2$OBn group.

In the same way, R$_4$ may advantageously represent a hydrogen or halogen atom or an OH or OR$^{24}$ group, and in particular a hydrogen atom or an OH or OR$^{24}$ group, with R$^{24}$ as defined above.

Yet even more advantageously, R$_4$ may represent a hydrogen or halogen atom or an OH, —O—(C$_1$-C$_6$)-alkyl, —O-aryl and —O—(C$_1$-C$_6$)-alkyl-aryl group, and in particular, a hydrogen atom or an OH, —O—(C$_1$-C$_6$)-alkyl, —O-aryl and —O—(C$_1$-C$_6$)-alkyl-aryl group.

In particular, R$_4$ can represent a hydrogen or halogen (such as Br, Cl, F) atom or an OH group, and advantageously, a hydrogen atom or an OH group, and notably a hydrogen atom.

Preferably, R$_4$=H when n=1 and R$_4$=H or OH when n=0.

Advantageously, X$_1$ is selected from the group consisting of a hydrogen atom, an halogen atom, a OH, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$, CO$_2$R$^{24}$, NR$^{25}$R$^{26}$, NR$^{25}$COR$^{24}$ and CONR$^{25}$R$^{26}$ group; more advantageously from the group consisting of a hydrogen atom, an halogen atom, a OH, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$ and CO$_2$R$^{24}$ group; even more advantageously from the group consisting of a hydrogen atom, an halogen atom, a OH, (C$_1$-C$_6$)-alkyl and OR$^{24}$ group.

Advantageously, U, V and W represent, independently from one another, a phenyl, pyrazolyl, N—(C$_1$-C$_6$)alkyl-pyrazolyl, or thienyl ring, the said ring being optionally substituted with one or more substituents selected from the group consisting of an halogen atom, a OH, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$, CO$_2$R$^{24}$, NR$^{25}$R$^{26}$, NR$^{25}$COR$^{24}$ and CONR$^{25}$R$^{26}$ group; more advantageously from the group consisting of an halogen atom, a OH, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$ and CO$_2$R$^{24}$ group; even more advantageously from the group consisting of an halogen atom, a OH, (C$_1$-C$_6$)-alkyl and OR$^{24}$ group.

(1) In a first embodiment, n is 1.

In a first subclass of this embodiment, m=0 and U is an optionally substituted phenyl. The compounds according to the invention can thus be represented by the following formula (I-1), and more particularly by the following formulas (I-1a), (I-1b) and (I-1c), and in particular (I-1a) and (I-1c):

(I-1)

(I-1a)

(I-1b)

and

(I-1c)

or a pharmaceutically or cosmetically acceptable salt thereof, a tautomer, a stereoisomer or a mixture of stereoisomers in any proportion, in particular a mixture of enantiomers, and particularly a racemate mixture, wherein:

R, R$_1$, R$_2$, and R$_3$ are as defined above, and

X$_1$, X$_2$, X$_3$, X$_4$ and X$_5$ represent, independently from one another, a hydrogen atom, an halogen atom, a CN, OH, SO$_2$, SiR$^m$R$^n$R$^o$, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$, CO$_2$R$^{24}$, NR$^{25}$R$^{26}$, NR$^{25}$COR$^{24}$, CONR$^{25}$R$^{26}$, SR$^{24}$, SO$_2$R$^{24}$, CSR$^{24}$ or OSO$_3$R$^{24}$ group; advantageously from the group consisting of a hydrogen atom, an halogen atom, a OH, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$, CO$_2$R$^{24}$, NR$^{25}$R$^{26}$, NR$^{25}$COR$^{24}$ and CONR$^{25}$R$^{26}$ group; more advantageously from the group consisting of a hydrogen atom, an halogen atom, a OH, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$ and CO$_2$R$^{24}$ group; even more advantageously from the group consisting of a hydrogen atom, an halogen atom, a OH, (C$_1$-C$_6$)-alkyl and OR$^{24}$ group.

Examples within this first subclass include but are not limited to:

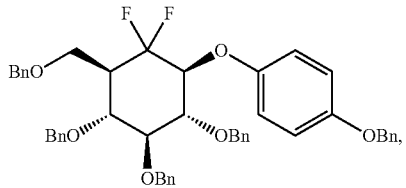

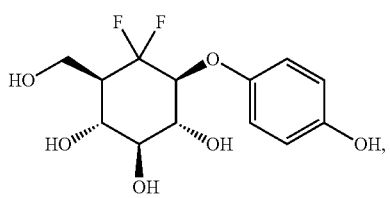

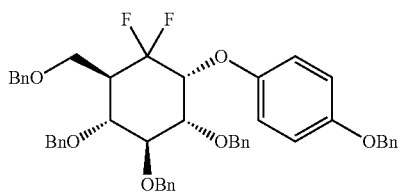

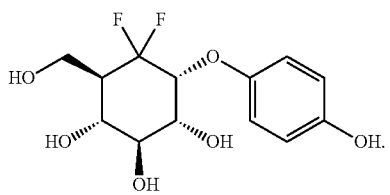

In a second subclass of this embodiment, m=1, p=0 and U and V represent, independently from one another, an optionally substituted phenyl. The compounds according to the invention can thus be represented by the following formula (I-2), and more particularly by the following formulas (I-2a) and (I-2b), and in particular (I-2a):

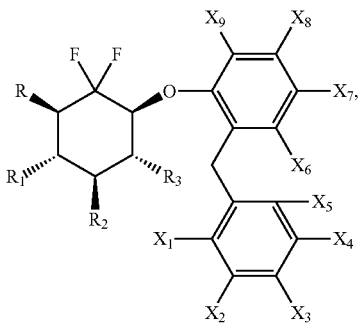

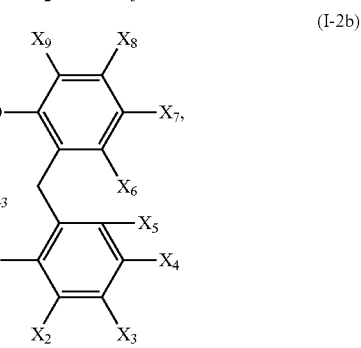

or a pharmaceutically or cosmetically acceptable salt thereof, a tautomer, a stereoisomer or a mixture of stereoisomers in any proportion, in particular a mixture of enantiomers, and particularly a racemate mixture,
wherein:
R, $R_1$, $R_2$, and $R_3$ are as defined above, and
$X_1$, $X_2$, $X_3$, $X_4$, $X_5$, $X_6$, $X_7$, $X_8$ and $X_9$ represent, independently from one another, a hydrogen atom, an halogen atom, a CN, OH, $SO_2$, $SiR'''R''R°$, $(C_1-C_6)$-alkyl, $(C_2-C_6)$-alkenyl, $(C_2-C_6)$-alkynyl, $(C_3-C_7)$-cycloalkyl, $OR^{24}$, $COR^{24}$, $OCOR^{24}$, $CO_2R^{24}$, $NR^{25}R^{26}$, $NR^{25}COR^{24}$, $CONR^{25}R^{26}$, $SR^{24}$, $SO_2R^{24}$, $CSR^{24}$ or $OSO_3R^{24}$ group; advantageously from the group consisting of a hydrogen atom, an halogen atom, a OH, $(C_1-C_6)$-alkyl, $(C_2-C_6)$-alkenyl, $(C_2-C_6)$-alkynyl, $(C_3-C_7)$-cycloalkyl, $OR^{24}$, $COR^{24}$, $OCOR^{24}$, $CO_2R^{24}$, $NR^{25}R^{26}$, $NR^{25}COR^{24}$ and $CONR^{25}R^{26}$ group; more advantageously from the group consisting of a hydrogen atom, an halogen atom, a OH, $(C_1-C_6)$-alkyl, $(C_2-C_6)$-alkenyl, $(C_2-C_6)$-alkynyl, $(C_3-C_7)$-cycloalkyl, $OR^{24}$, $COR^{24}$, $OCOR^{24}$ and $CO_2R^{24}$ group; even more advantageously from the group consisting of a hydrogen atom, an halogen atom, a OH, $(C_1-C_6)$-alkyl and $OR^{24}$ group.

Examples within this second subclass include but are not limited to:

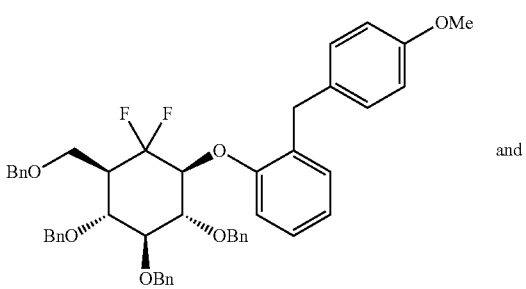

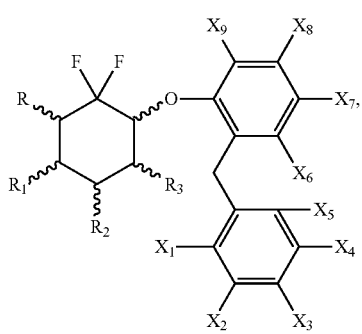

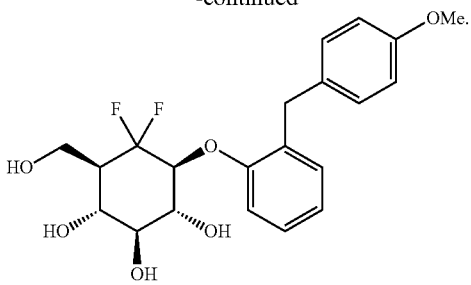

In a third subclass of this embodiment, m=1, p=0, U is a pyrazolyl or N—(C$_1$-C$_6$)alkyl-pyrazolyl group and V is an optionally substituted phenyl. The compounds according to the invention can thus be represented by the following formula (I-3), and more particularly by the following formulas (I-3a) and (I-3b), and in particular (I-3a):

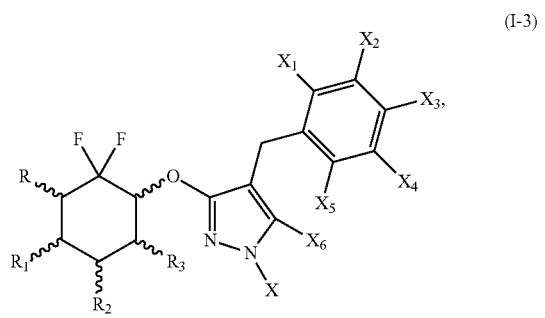
(I-3)

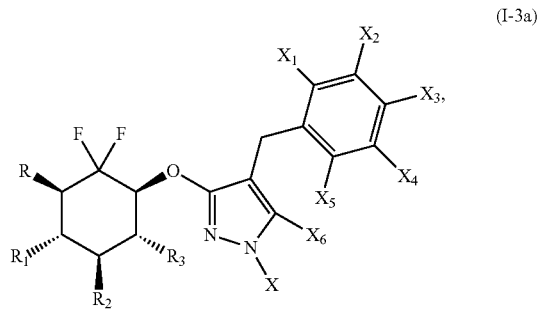
(I-3a)

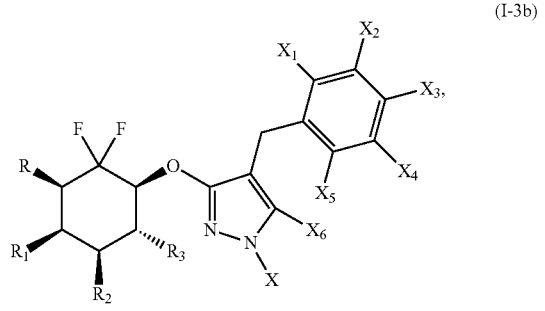
(I-3b)

or a pharmaceutically or cosmetically acceptable salt thereof, a tautomer, a stereoisomer or a mixture of stereoisomers in any proportion, in particular a mixture of enantiomers, and particularly a racemate mixture,
wherein:
R, R$_1$, R$_2$, and R$_3$ are as defined above,
X$_1$, X$_2$, X$_3$, X$_4$, X$_5$ and X$_6$ represent, independently from one another, a hydrogen atom, an halogen atom, a CN, OH, SO$_2$, SiR'''R''R°, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$, CO$_2$R$^{24}$, NR$^{25}$R$^{26}$, NR$^{25}$COR$^{24}$, CONR$^{25}$R$^{26}$, SR$^{24}$, SO$_2$R$^{24}$, CSR$^{24}$ or OSO$_3$R$^{24}$ group; advantageously from the group consisting of a hydrogen atom, an halogen atom, a OH, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$, CO$_2$R$^{24}$, NR$^{25}$R$^{26}$, NR$^{25}$COR$^{24}$ and CONR$^{25}$R$^{26}$ group; more advantageously from the group consisting of a hydrogen atom, an halogen atom, a OH, (C$_1$-C$_6$)-alkyl, (C$_2$-C$_6$)-alkenyl, (C$_2$-C$_6$)-alkynyl, (C$_3$-C$_7$)-cycloalkyl, OR$^{24}$, COR$^{24}$, OCOR$^{24}$ and CO$_2$R$^{24}$ group; even more advantageously from the group consisting of a hydrogen atom, an halogen atom, a OH, (C$_1$-C$_6$)-alkyl and OR$^{24}$ group, and X represents a hydrogen atom or a (C$_1$-C$_6$)-alkyl group.

Examples within this third subclass include but are not limited to:

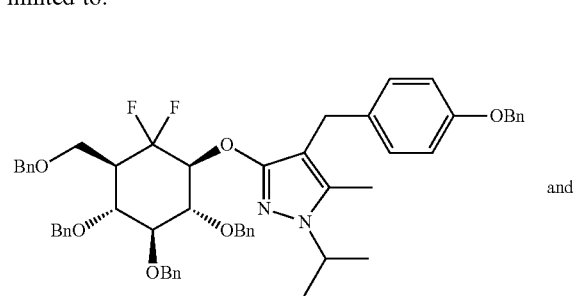
and

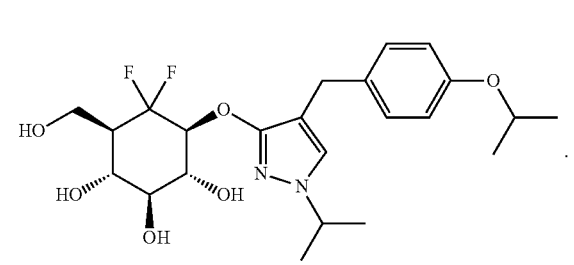

(2) In a second embodiment, n is 0.

In a first subclass of this embodiment, m=1, p=0 and U and V are independently an optionally substituted phenyl. The compounds according to the invention can thus be represented by the following formula (I-4), and more particularly by the following formulas (I-4a) and (I-4b), and in particular (I-4a):

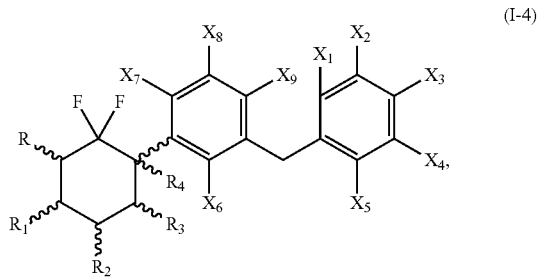
(I-4)

-continued

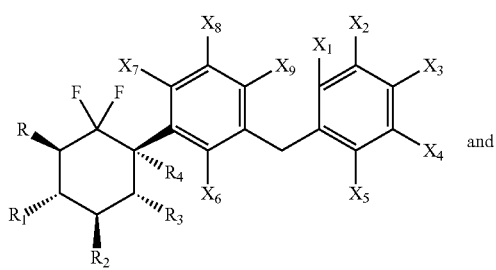
(I-4a)

and

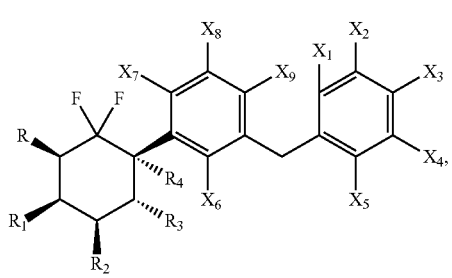
(I-4b)

or a pharmaceutically or cosmetically acceptable salt thereof, a tautomer, a stereoisomer or a mixture of stereoisomers in any proportion, in particular a mixture of enantiomers, and particularly a racemate mixture, wherein:

R, $R_1$, $R_2$, $R_3$ and $R_4$ are as defined above, and $X_1$, $X_2$, $X_3$, $X_4$, $X_5$, $X_6$, $X_7$, $X_8$ and $X_9$ represent, independently from one another, a hydrogen atom, an halogen atom, a CN, OH, $SO_2$, $SiR'''R''R^o$, $(C_1-C_6)$-alkyl, $(C_2-C_6)$-alkenyl, $(C_2-C_6)$-alkynyl, $(C_3-C_7)$-cycloalkyl, $OR^{24}$, $COR^{24}$, $OCOR^{24}$, $CO_2R^{24}$, $NR^{25}R^{26}$, $NR^{25}COR^{24}$, $CONR^{25}R^{26}$, $SR^{24}$, $SO_2R^{24}$, $CSR^{24}$ or $OSO_3R^{24}$ group; advantageously from the group consisting of a hydrogen atom, an halogen atom, a OH, $(C_1-C_6)$-alkyl, $(C_2-C_6)$-alkenyl, $(C_2-C_6)$-alkynyl, $(C_3-C_7)$-cycloalkyl, $OR^{24}$, $COR^{24}$, $OCOR^{24}$, $CO_2R^{24}$, $NR^{25}R^{26}$, $NR^{25}COR^{24}$ and $CONR^{25}R^{26}$ group; more advantageously from the group consisting of a hydrogen atom, an halogen atom, a OH, $(C_1-C_6)$-alkyl, $(C_2-C_6)$-alkenyl, $(C_2-C_6)$-alkynyl, $(C_3-C_7)$-cycloalkyl, $OR^{24}$, $COR^{24}$, $OCOR^{24}$ and $CO_2R^{24}$ group; even more advantageously from the group consisting of a hydrogen atom, an halogen atom, a OH, $(C_1-C_6)$-alkyl and $OR^{24}$ group.

Examples within this first subclass include but are not limited to:

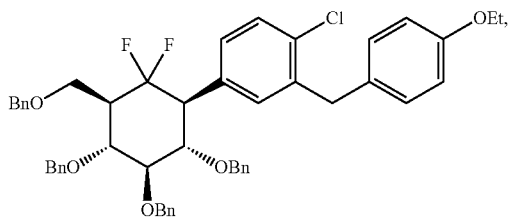

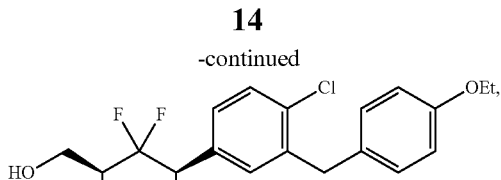

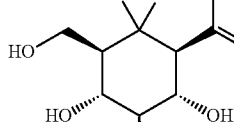

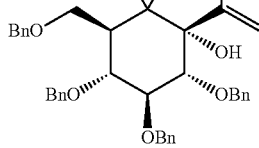

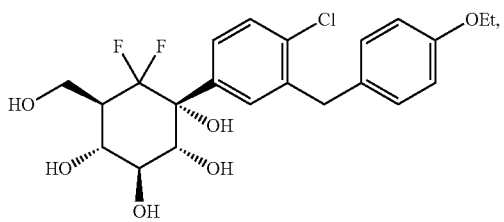

In a second subclass of this embodiment, m=1, p=1, U and W are independently an optionally substituted phenyl and V is an optionally substituted thienyl. The compounds according to the invention can thus be represented by the following formula (I-5) and more particularly by the following formulas (I-5a) and (I-5b), and in particular (I-5a):

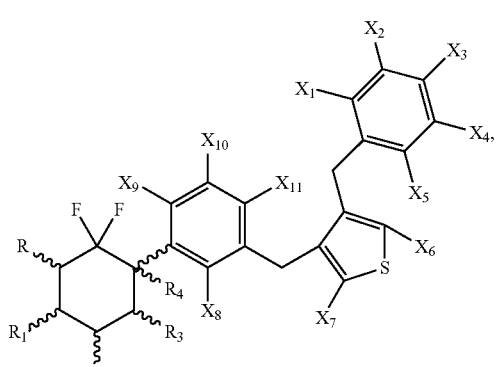

(I-5)

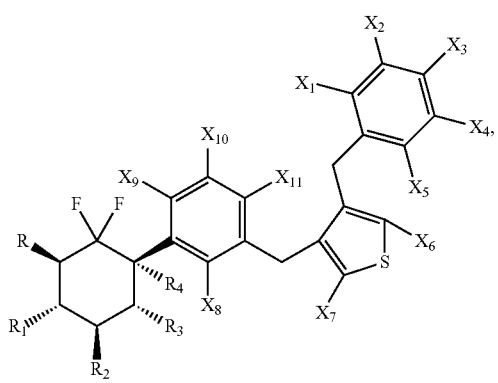

(I-5a)

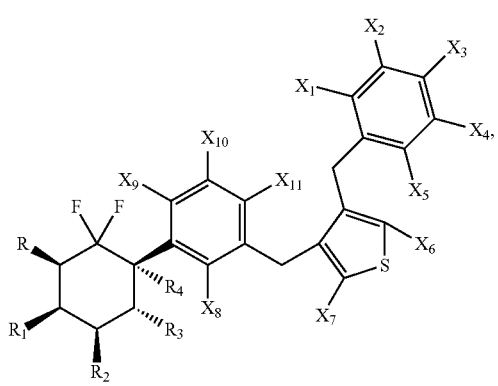

(I-5b)

or a pharmaceutically or cosmetically acceptable salt thereof, a tautomer, a stereoisomer or a mixture of stereoisomers in any proportion, in particular a mixture of enantiomers, and particularly a racemate mixture,
wherein:
R, $R_1$, $R_2$, $R_3$ and $R_4$ are as defined above, and
$X_1, X_2, X_3, X_4, X_5, X_6, X_7, X_8, X_9, X_{10}$ and $X_{11}$ represent, independently from one another, a hydrogen atom, an halogen atom, a CN, OH, $SO_2$, $SiR'''R''R^o$, $(C_1\text{-}C_6)$-alkyl, $(C_2\text{-}C_6)$-alkenyl, $(C_2\text{-}C_6)$-alkynyl, $(C_3\text{-}C_7)$-cycloalkyl, $OR^{24}$, $COR^{24}$, $OCOR^{24}$, $CO_2R^{24}$, $NR^{25}R^{26}$, $NR^{25}COR^{24}$, $CONR^{25}R^{26}$, $SR^{24}$, $SO_2R^{24}$, $CSR^{24}$ or $OSO_3R^{24}$ group; advantageously from the group consisting of a hydrogen atom, an halogen atom, a OH, $(C_1\text{-}C_6)$-alkyl, $(C_2\text{-}C_6)$-alkenyl, $(C_2\text{-}C_6)$-alkynyl, $(C_3\text{-}C_7)$-cycloalkyl, $OR^{24}$, $COR^{24}$, $OCOR^{24}$, $CO_2R^{24}$, $NR^{25}R^{26}$, $NR^{25}COR^{24}$ and $CONR^{25\text{-}26}$ group; more advantageously from the group consisting of a hydrogen atom, an halogen atom, a OH, $(C_1\text{-}C_6)$-alkyl, $(C_2\text{-}C_6)$-alkenyl, $(C_2\text{-}C_6)$-alkynyl, $(C_3\text{-}C_7)$-cycloalkyl, $OR^{24}$, $COR^{24}$, $OCOR^{24}$ and $CO_2R^{24}$ group; even more advantageously from the group consisting of a hydrogen atom, an halogen atom, a OH, $(C_1\text{-}C_6)$-alkyl and $OR^{24}$ group.

Examples within this second subclass include but are not limited to:

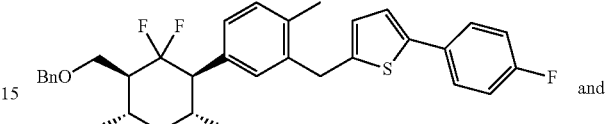 and

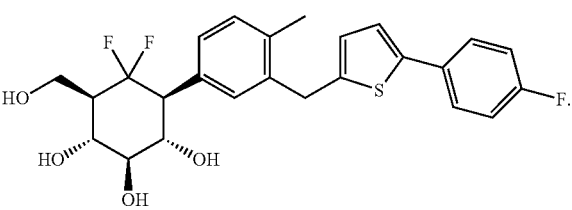

Compounds according to the invention can thus be selected from the following compounds:

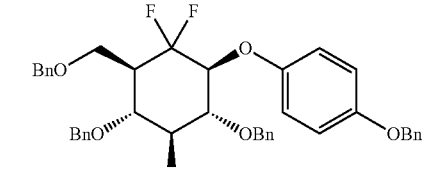

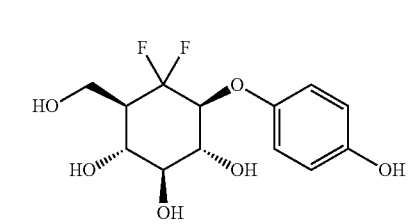

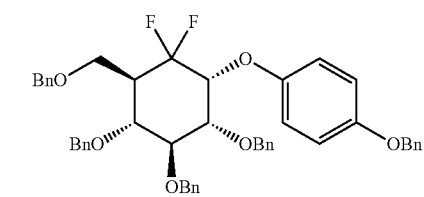

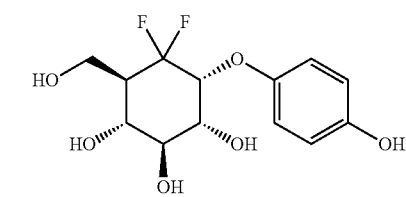

17
-continued

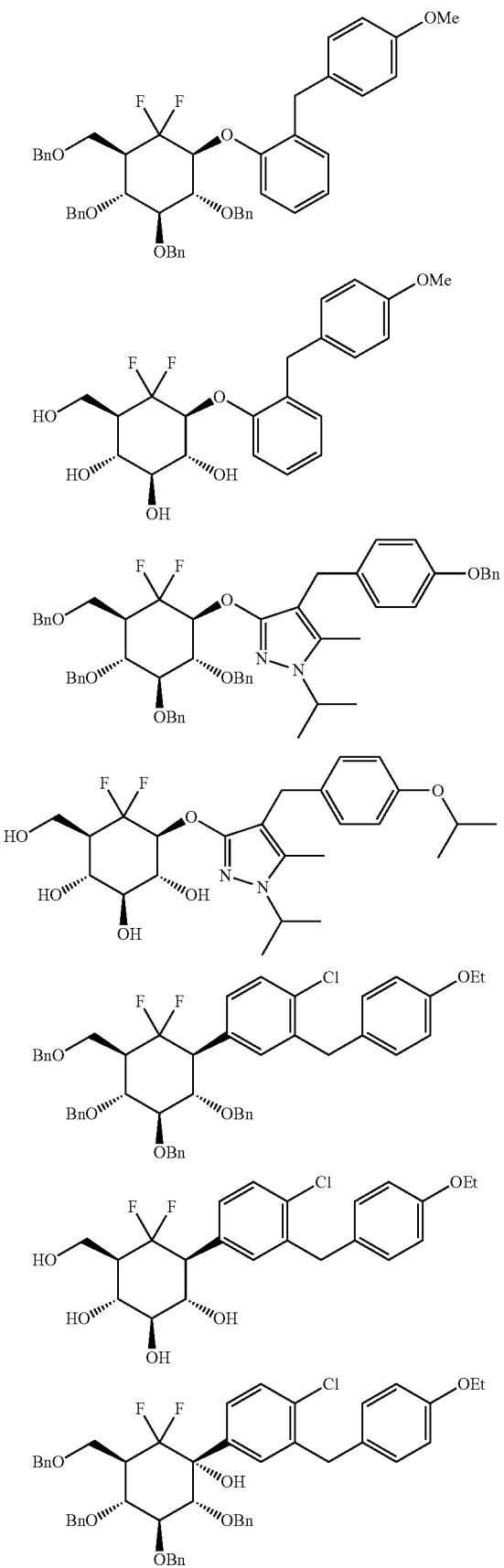

18
-continued

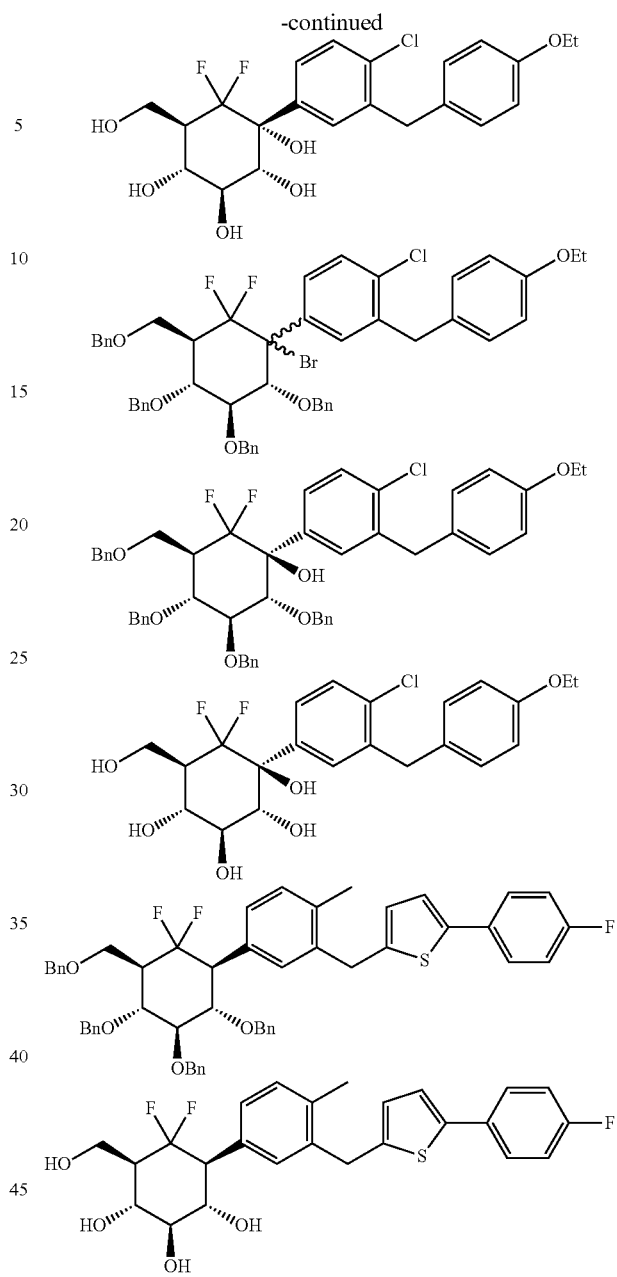

Another object of this invention is a compound as defined above, for use as a drug, in particular as an inhibitor of the sodium-dependent glucose co-transporter, such as SGLT1, SGLT2 and SGLT3.

Within the meaning of this invention, "inhibitor of the sodium-dependent glucose co-transporter" is understood to mean a compound capable of inhibiting partially or totally the sodium-dependent glucose co-transporter.

More particularly, the compounds of the invention may be used for treating or preventing diabetes, and more particularly type-II diabetes, diabetes-related complications, such as arteritis of the lower extremities, cardiac infarction, renal insufficiency, neuropathy or blindness, hyperglycemia, hyperinsulinemia, obesity, hypertriglyceridemia, X syndrome and arteriosclerosis. The compounds of the invention are used in particular for treating or preventing diabetes.

The compounds of the invention may likewise be used as an anti-cancer, anti-infective, anti-viral, anti-thrombotic or anti-inflammatory drug.

The invention likewise relates to a compound of the invention for its use in the treatment or prevention of diabetes, and more particularly type-II diabetes, diabetes-related complications, such as arteritis of the lower extremities, cardiac infarction, renal insufficiency, neuropathy or blindness, hyperglycemia, hyperinsulinemia, obesity, hypertriglyceridemia, X syndrome and arteriosclerosis, as well as for its use as an anti-cancer, anti-infective, anti-viral, anti-thrombotic or anti-inflammatory drug, and in particular in the treatment or prevention of diabetes.

The invention likewise relates to the use of a compound of the invention for the manufacture of a drug intended for the treatment or prevention of diabetes, and more particularly type-II diabetes, diabetes-related complications, such as arteritis of the lower extremities, cardiac infarction, renal insufficiency, neuropathy or blindness, hyperglycemia, hyperinsulinemia, obesity, hypertriglyceridemia, X syndrome and arteriosclerosis, as well as for the manufacture of an anti-cancer, anti-infective, anti-viral, anti-thrombotic or anti-inflammatory drug, and in particular for the treatment or prevention of diabetes.

The invention likewise relates to a method for the treatment or prevention of diabetes, and more particularly type-II diabetes, diabetes-related complications, such as arteritis of the lower extremities, cardiac infarction, renal insufficiency, neuropathy or blindness, hyperglycemia, hyperinsulinemia, obesity, hypertriglyceridemia, X syndrome and arteriosclerosis, as well as for an anti-cancer, anti-infective, anti-viral, anti-thrombotic or anti-inflammatory treatment, and in particular in for the treatment or prevention of diabetes, including the administration of an effective amount of at least one compound of the invention to a patient in need thereof.

Silylated compounds of the present invention, as well as compounds with $R=CH_2OBn$, $R_1=OBn$, $R_2=OBn$ and/or $R_3=OBn$, will not be preferred for their use as medicament.

The compounds useful as a drug, and notably in the treatment or prevention of diabetes, are more particularly the compounds of formula (Ia) or (Ib), and in particular (Ia); notably the compounds of formula (I-2) to (I-5), such as (I-2a) to (I-5a) and (I-2b) to (I-5b), and in particular (I-2a) to (I-5a).

Another object of this invention is the cosmetic use of a compound of the invention as defined above, for lightening, bleaching, depigmenting the skin, removing blemishes from the skin, particularly age spots and freckles, or preventing pigmentation of the skin, or as antioxidant, via topical application in particular.

The present invention relates thus to a method for lightening, bleaching, depigmenting the skin, removing blemishes from the skin, particularly age spots and freckles, or preventing pigmentation of the skin, comprising the topical application of at least one compound of the invention.

Silylated compounds of the present invention, as well as compounds with $R=CH_2OBn$, $R_1=OBn$, $R_2=OBn$ and/or $R_3=OBn$, will not be preferred for their cosmetic use.

The compounds useful in the cosmetic field, in particular as depigmenting or lightening agents, are more particularly the compounds of formula (Ia), (Ib) or (Ic), and in particular (Ic); notably the compounds of formula (I-1), such as (I-1a), (I-1b) and (I-1c), and more particularly (I-1c).

In particular, compounds with depigmenting activity are tyrosinase inhibitors. They are in particular compounds of the following formula:

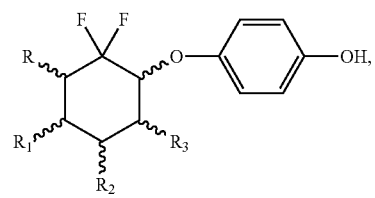

and preferably a compound of the following formula:

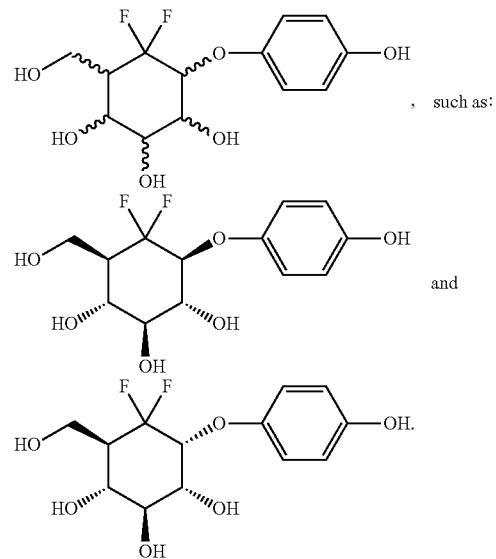

, such as:

and

Another object of this invention is a pharmaceutical or cosmetic composition including at least one compound of the invention as defined above and at least one pharmaceutically or cosmetically acceptable vehicle.

The compounds according to the invention can be administered orally, sublingually, parenterally, subcutaneously, intramuscularly, intravenously, transdermally, locally or rectally.

In the pharmaceutical compounds of this invention, for oral, sublingual, parenteral, subcutaneous, intramuscular, intravenous, transdermal, local or rectal administration, the active ingredient can be administered in unit forms of administration, mixed together with conventional pharmaceutical carriers, for animals or human beings. Suitable unit forms of administration include oral forms such as tablets, gel capsules, powders, granules and oral solutions or suspensions, sublingual or buccal forms of administration, parenteral, subcutaneous, intramuscular, intravenous, intranasal or intraocular forms of administration and rectal forms of administration.

When a solid composition is prepared in the form of tablets, the principal active ingredient is mixed with a pharmaceutical vehicle such as gelatine, starch, lactose, magnesium stearate, talc, gum arabic or the like. The tablets can be coated with sucrose or other suitable materials or else treated in such a way that they have an extended or delayed activity and continuously release a predetermined amount of active principle.

A gel capsule preparation is obtained by mixing the active ingredient with a diluent and by pouring the mixture obtained into soft or hard capsules.

A preparation in the form of a syrup or elixir can contain the active ingredient in conjunction with a sweetening agent, antiseptic, as well as a flavour-producing agent and appropriate colouring agent.

Powders or granules dispersible in water can contain the active ingredient mixed together with dispersing agents, wetting agents, or suspending agents, as well as with taste correctors or sweetening agents.

For rectal administration, suppositories are used, which are prepared with binding agents melting at rectal temperature, e.g., cocoa butter or polyethylene glycols.

For parenteral, intranasal or intraocular administration, aqueous suspensions are used, isotonic saline solutions or sterile and injectable solutions, which contain pharmacologically compatible dispersing agents and/or wetting agents.

The active principle can also be formulated as microcapsules, possibly with one or more additive carriers.

The compounds of the invention can be used at doses of between 0.01 mg and 1000 mg per day, given in a single dose once a day or administered in several doses throughout the day, e.g., twice daily in equal doses. The daily dose administered is advantageously between 0.1 mg and 100 mg, even more advantageously between 2.5 mg and 50 mg. It may be necessary to use doses exceeding these ranges, of which those skilled in the art will themselves be aware.

In one particular embodiment of the invention, the pharmaceutical or cosmetic composition can also be formulated for topical administration. It may be introduced in forms commonly known for this type of administration, i.e., in particular, lotions, foams, gels, dispersions, sprays, shampoos, serums, masks, body milks or creams, for example, with excipients enabling, in particular, penetration of the skin so as to improve the properties and accessibility of the active principle. Besides the composition according to the invention, these compositions generally further contain a physiologically acceptable medium, which generally contains water or a solvent, e.g., alcohols, ethers or glycols. They can also contain surface-active agents, preservatives, stabilizers, emulsifiers, thickeners, other active principles producing a complementary or possibly synergic effect, trace elements, essential oils, perfumes, colouring agents, collagen, chemical or mineral filters, hydrating agents or thermal waters.

In one particular embodiment, the pharmaceutical composition of the invention may include at least one other active principle, in addition to the compound of the invention.

Examples of active principles that can be cited are antidiabetic agents, such as sulfonylurea-type compounds which are hypoglycemic sulfamides which increase insulin secretion like, e.g., chlorpropamide, tolbutamide, tolazamide, glipizide, gliclazide, glibenclamide, gliquidone and glimepiride, biguanides which reduce the hepatic glyconeogenesis and the insulin resistance like metformine, thiazolidinediones (also called glitazones) which increase the sensibility to insulin like rosiglitazone, pioglitazone and ciglitazone, alpha-glucosidases inhibitors which slow down the intestinal absorption of carbohydrates like acarbose, miglitol and voglibose, meglitinides (also called glitinides) which increase insulin pancreatic secretion like repaglinide and nateglinide, incretin mimics like exenatide or dipeptidylpeptidase-4 (DPP4) inhibitors like sitagliptin, vildagliptin and insulin, or antilipidic agents, such as statins which reduce cholesterol by inhibiting the enzyme HMG-CoA reductase like atorvastatin and cerivastatin, fibrates like bezafibrate, gemfibrozil and fenofibrate, or ezetimibe.

The present invention concerns also processes for preparing a compound according to the invention.

The present invention concerns thus a process for preparing a compound of formula (I) according to the invention for which $R_4$=H comprising the fluorination of a compound of the following formula (II):

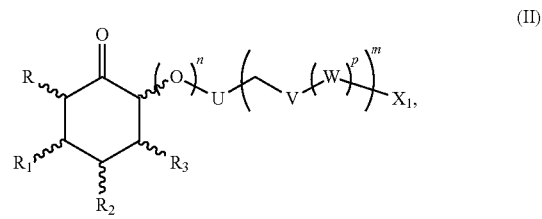

wherein R, $R_1$, $R_2$, $R_3$, $X_1$, U, V, W, n, m and p are as defined above.

The fluorination will be carried out in the presence of a fluorinating agent, such as DAST (diethylaminosulphurtrifluoride).

If necessary additional steps of protection, deprotection, substitution, etc. can be carried out, these steps being well known to the person skilled in the art.

The compound of formula (I) obtained can be recovered by separation from the reaction medium by methods well known to the person skilled in the art, such as by extraction, evaporation of the solvent or by precipitation or crystallisation (followed by filtration).

The compound can be also purified if necessary by methods well known to the person skilled in the art, such as by recrystallisation, by distillation, by chromatography on a column of silica gel or by high performance liquid chromatography (HPLC).

The compound of formula (II) can be prepared by oxidation of a compound of the following formula (III):

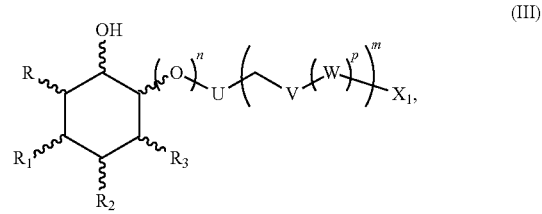

wherein R, $R_1$, $R_2$, $R_3$, $X_1$, U, V, W, n, m and p are as defined above.

The oxidation will be carried out in the presence of an oxidant according to procedures well known to the person skilled in the art. The oxidant can be for example Dess-Martin periodinane, PCC (Pyridinium chlorochromate), etc.

When n=1, the process for preparing the compound of formula (III) can comprise the following successive steps:
  (a1) coupling between a compound of the following formula (IV):

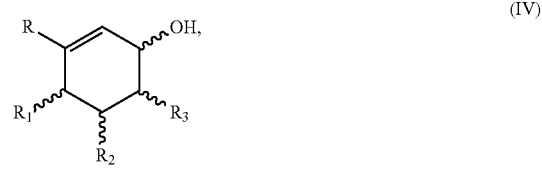

wherein R, $R_1$, $R_2$ and $R_3$ are as defined above, and a compound of the following formula (V):

(V)

wherein $X_1$, U, V, W, m and p are as defined above, to give a compound of the following formula (VI):

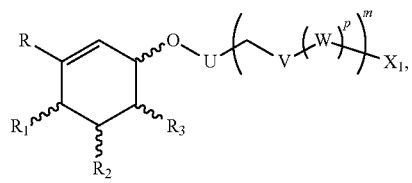
(VI)

wherein R, $R_1$, $R_2$, $R_3$, $X_1$, U, V, W, m and p are as defined above, and (b1) hydroboration-oxidation reaction of the compound of formula (VI) obtained in previous step (a1) to give a compound of formula (III) with n=1.

Step (a1) can be carried out in the conditions of the Mitsunobu reaction well known to the person skilled in the art, notably using DEAD (diethyl azo dicarboxylate), DIAD (diisopropyl azo dicarboxylate) or ADDP (azodicarboxylic acid dipiperidine) as coupling agent and $PPh_3$ or $P(nBu)_3$ as phosphine.

Step (b1) can be carried out in conditions well known to the person skilled in the art, notably by reaction with a borane such as $BH_3$, and in particular $BH_3.THF$ or $BH_3.Me_2S$, in a solvent such as THF, followed by the addition of hydrogen peroxide in the presence of a base such as sodium hydroxide.

When n=0, the process for preparing the compound of formula (III) can comprise the following successive steps:

(a2) coupling between a compound of the following formula (VII):

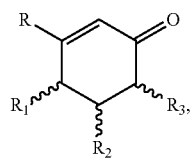
(VII)

wherein R, $R_1$, $R_2$ and $R_3$ are as defined above, and a compound of the following formula (VIII):

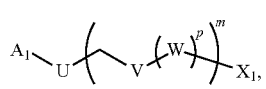
(VIII)

wherein $X_1$, U, V, W, m and p are as defined above and $A_1$ represents —Li or —Mg-Hal, Hal being a halogen atom, to give a compound of the following formula (IX):

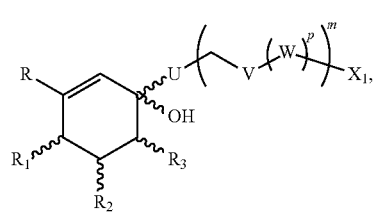
(IX)

wherein R, $R_1$, $R_2$, $R_3$, $X_1$, U, V, W, m and p are as defined above, (b2) reduction of the compound of formula (IX) obtained in previous step (a2) to give a compound of the following formula (X):

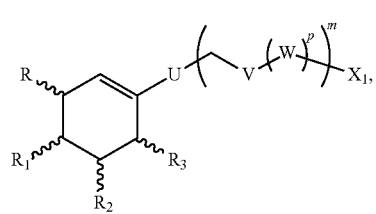
(X)

wherein R, $R_1$, $R_2$, $R_3$, $X_1$, U, V, W, m and p are as defined above, and (c2) hydroboration-oxidation reaction of the compound of formula (X) obtained in previous step (b2) to give a compound of formula (III) with n=0.

Step (a2) can be carried out through the reaction of compound of formula (VIII) obtained from the halogenated derivative by reaction with magnesium to form the Grignard reagent or by halogen exchange using a lithium base such as n-butyllithium to form the corresponding lithiated compound, with compound of formula (VII), in a solvent such as THF.

Such compound of formula (VII) is obtained in conditions well known to the person skilled in the art, and notably according to a process described in EP0240175 or *Carbohydrate Research* 2010, 345, 1056-1060.

The compound of formula (VIII) can be obtained from the halogenated derivative by reaction with magnesium to form the Grignard reagent or by halogen exchange using a lithium base such as n-butyllithium to form the corresponding lithiated compound.

Step (b2) can be carried out in the presence of a reducing agent such as $Et_3SiH$ and a Lewis acid such as $BH_3.Et_2O$.

Step (c2) corresponds to previous step (b1).

The process to prepare compounds according to the invention with $R_4$=H will be better detailed below and in the following experimental part.

Scheme A: Synthetic pathway for compounds of the first embodiment (wherein n = 1)

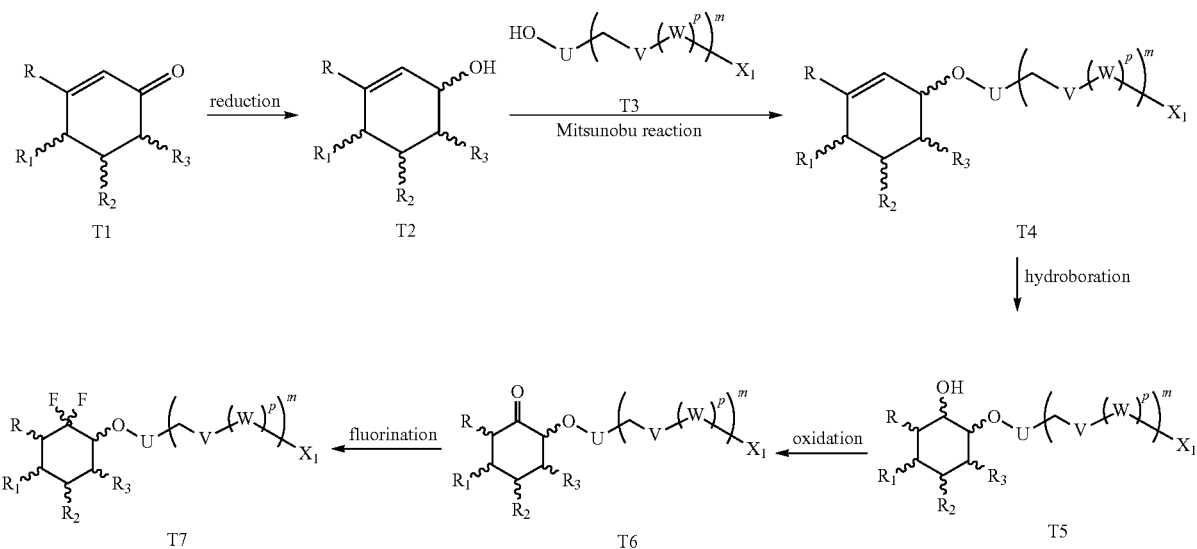

(a) In a first step cyclohexenone T1 undergoes a reduction involving standard conditions such as NaBH₄, NaBH₄/CeCl₃, LiAlH₄ or L-selectride.
(b) A Mitsunobu-coupling reaction between compound T2 and alcohol T3 then occurs under standard conditions using DEAD, DIAD or ADDP as coupling agent and PPh₃ or P(nBu)₃ as phosphine.
(c) Hydroboration of compound T4 using BH₃.THF or BH₃.Me₂S leads to compound T5.

(d) The alcohol function of compound T5 is oxidized into a ketone according to typical procedures involving PCC, Dess-Martin periodinane yielding compound T6.
(e) Compound T6 can be fluorinated using fluorinating agent such as DAST to afford the difluorocarbasugar T7. In a last step, protective groups can be removed according to typical procedures described in Protective groups (*Protective groups in organic synthesis*, T. W. Greene).

More particularly:

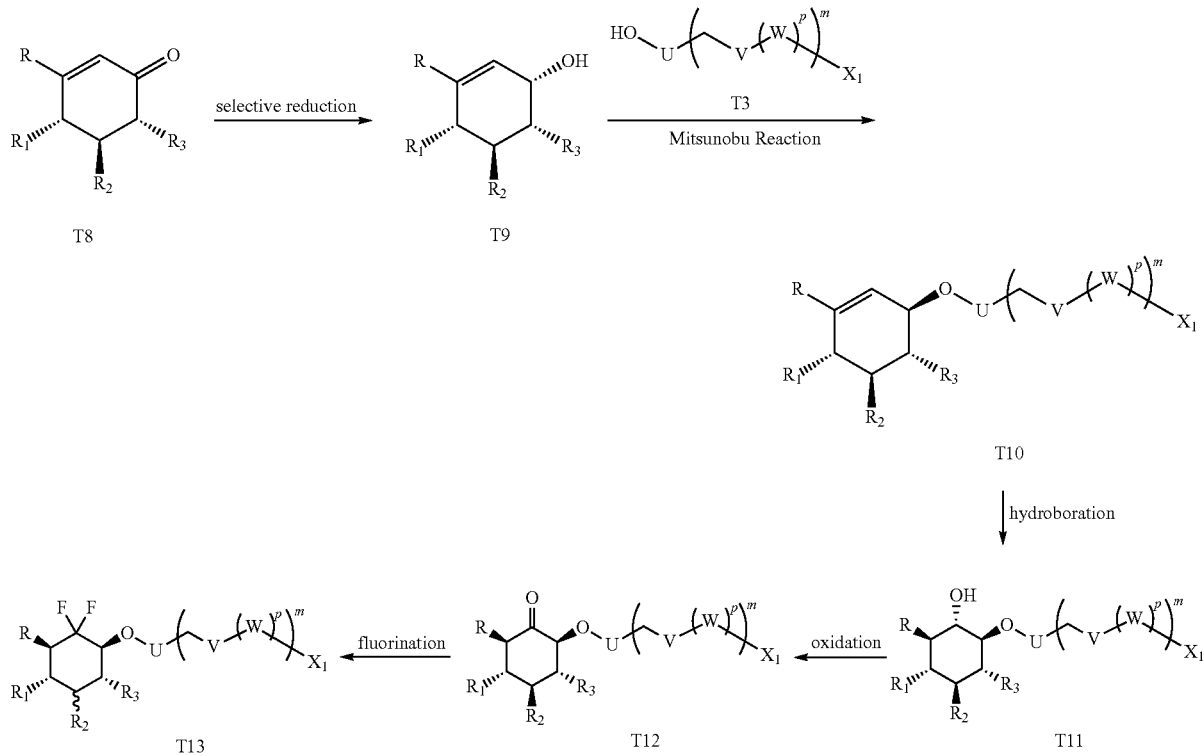

(a) In a first step cyclohexenone T8 undergoes a regioselective reduction involving lithium tri-sec-butylborohydride as described in *Can. J. Chem* 2004, 82, 1361-1364.
(b) A Mitsunobu-coupling reaction between compound T9 and alcohol T3 then occurs under standard conditions using DEAD, DIAD or ADDP as coupling agent and PPh$_3$ or P(nBu)$_3$ as phosphine.
(c) Hydroboration of compound T10 using BH$_3$.THF or BH$_3$.Me$_2$S leads to compound T11.
(d) The alcohol function of compound T11 is oxidized into a ketone according to typical procedures involving PCC, Dess-Martin periodinane yielding compound T12.
(e) Compound T12 can be fluorinated using fluorinating agent such as DAST to afford the difluorocarbasugar T13. In a last step, protective groups can be removed according to typical procedures described *Protective groups in organic synthesis*, T. W. Greene.

Cyclohexenone T8 was prepared according to EP0240175 or Cumpstey, I. *Carbohydrate Research* 2010, 345, 1056-1060, applying the synthesis to the glucose series from the commercially available 2,3,4,6-O-benzyl-D-glucopyranose.

Compound T3 can be either commercially available (first subclass) or synthesized according to:

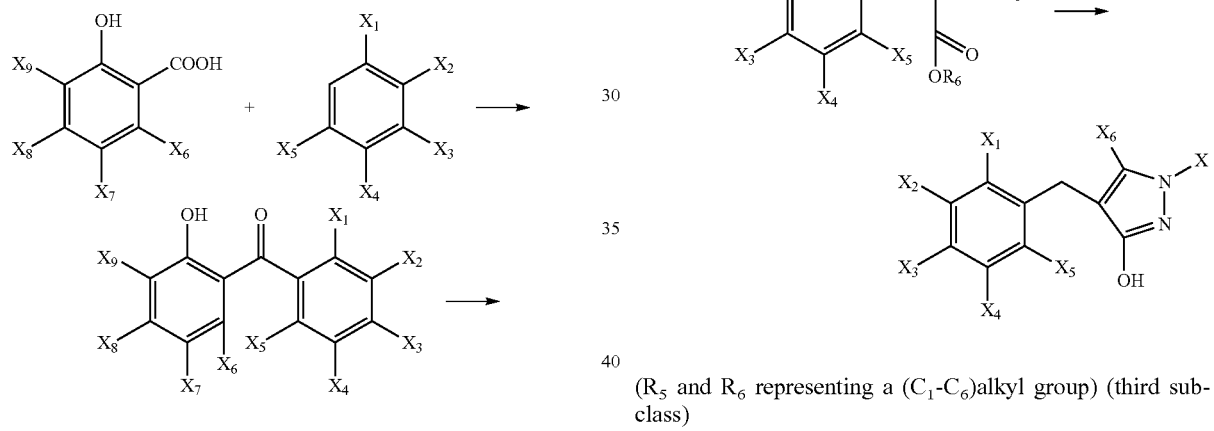

(second subclass)
Or ($R_5$ and $R_6$ representing a ($C_1$-$C_6$)alkyl group) (third subclass)

Scheme B: Synthetic pathway for compounds of the second embodiment (wherein n = 0 and R4 = H)

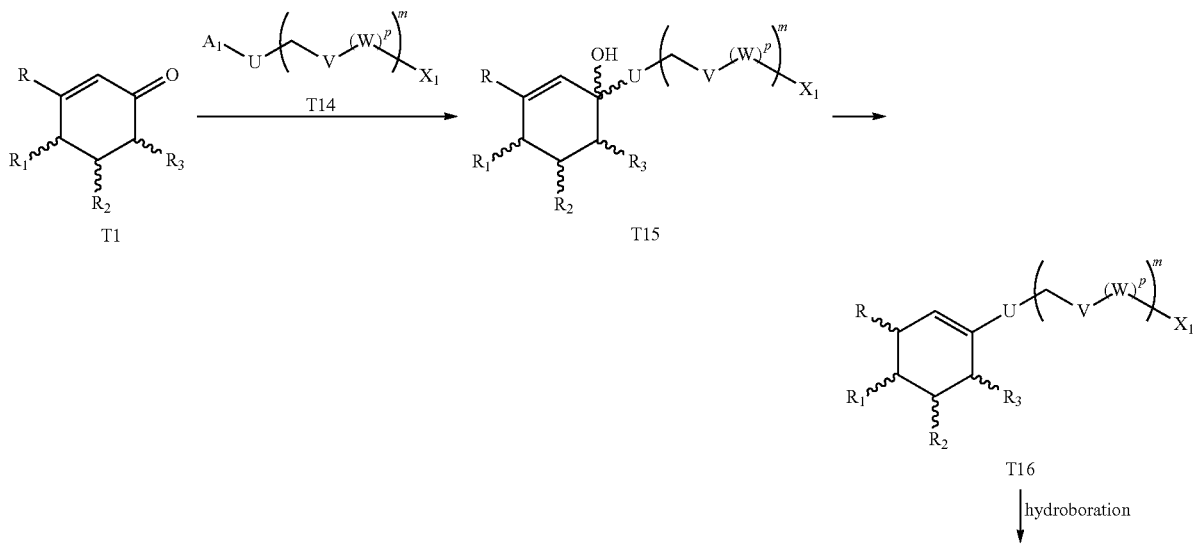

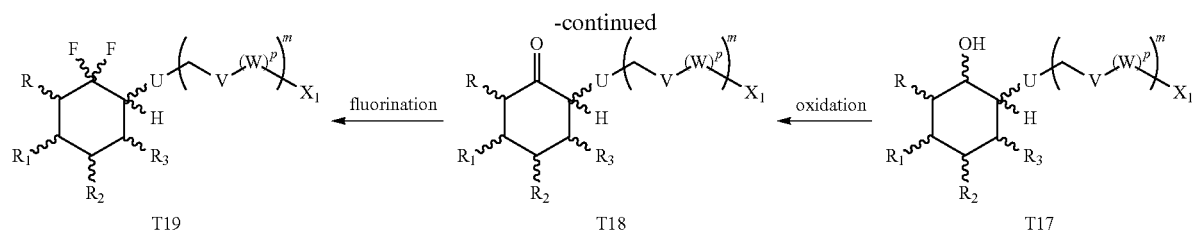

(a) In a first step, a Grignard reagent or a lithiated compound T14, prepared from the corresponding halogenated compound according to a typical procedure, is added onto cyclohexenone T1.
(b) In the next step of the synthesis, compound T15 is treated with a reducing agent such as $Et_3SiH$ in the presence of a Lewis acid such as $BF_3.Et_2O$, yielding compound T16.
(c) Hydroboration of compound T16 using $BH_3.THF$ or $BH_3.Me_2S$ leads to compound T17.
(d) The alcohol function of compound T17 is oxidized into a ketone according to typical procedures involving PCC, Dess-Martin periodinane yielding compound T18.
(e) Compound T18 can be fluorinated using fluorinating agent such as DAST to afford the difluorocarbasugar T19. In a last step, protective groups can be removed according to typical procedures described in *Protective groups in organic synthesis*, T. W. Greene.
And more particularly:

(a) In a first step, a Grignard reagent or a lithiated compound T14, prepared from the corresponding halogenated compound according to a typical procedure, is added onto cyclohexenone T8.
(b) In the next step of the synthesis, compound T20 is treated with a reducing agent such as $Et_3SiH$ in the presence of a Lewis acid such as $BF_3.Et_2O$, yielding compound T21.
(c) Hydroboration of compound T21 using $BH_3.THF$ or $BH_3.Me_2S$ leads to compound T22.
(d) The alcohol function of compound T22 is oxidized into a ketone according to typical procedures involving PCC, Dess-Martin periodinane yielding compound T23.
(e) Compound T23 can be fluorinated using fluorinating agent such as DAST to afford the difluorocarbasugar T24. In a last step, protective groups can be removed according to typical procedures described in *Protective groups in organic synthesis*, T. W. Greene.

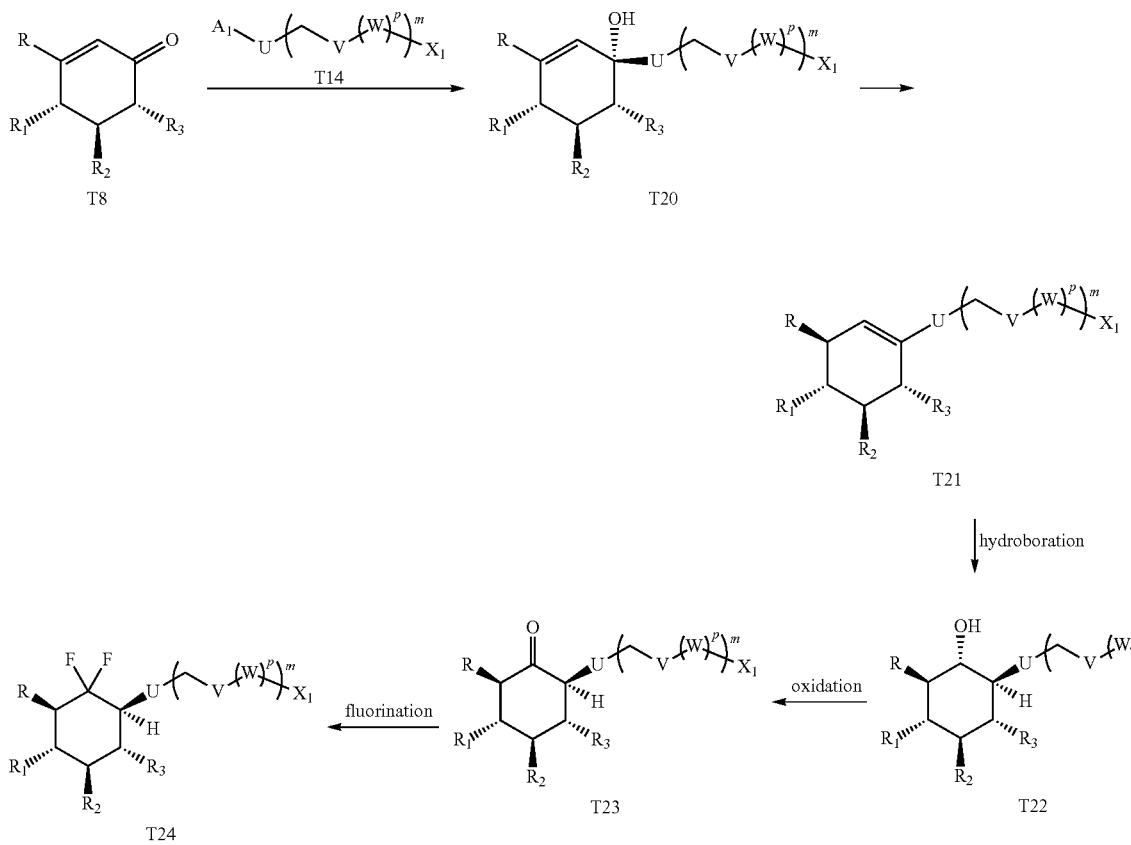

Halogenated compound giving access to compound T14 can be synthesized according to the following scheme:

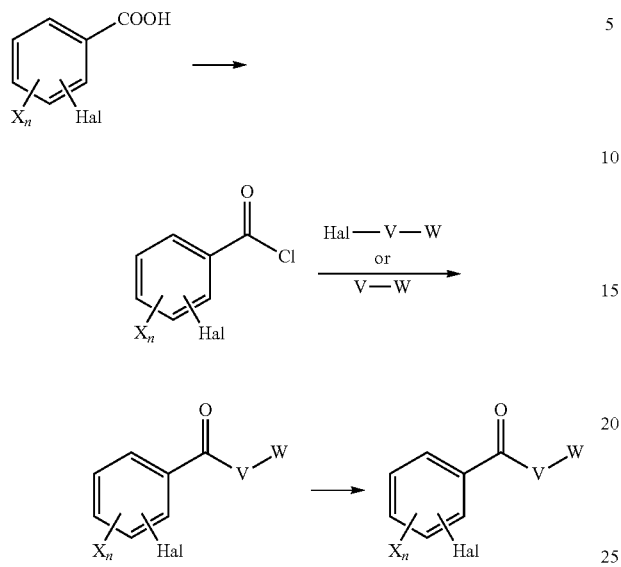

The present invention concerns also a process for preparing a compound of the formula (I) according to the invention for which n=0 and $R_4 \neq H$ comprising the coupling of a compound of formula (VIII) as defined above and a compound of the following formula (XI)

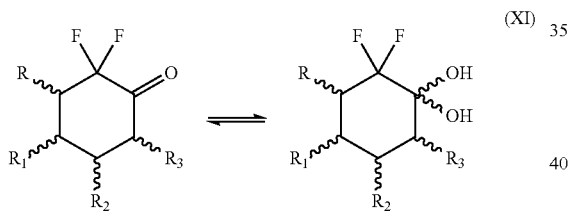

wherein R, $R_1$, $R_2$, and $R_3$ are as defined above, to give a compound of formula (I) for which n=0 and $R_4$=OH,
followed optionally by the substitution of the OH function to give a compound of formula (I) for which n=0 and $R_4$=halogen, $OSiR^jR^kR^l$, $OR^{21}$, $OCOR^{21}$, $OCO_2R^{21}$, or $OCONR^{22}R^{23}$.

These steps of coupling and substitution can be carried out in conditions well known to the person skilled in the art.

If necessary additional steps of protection, deprotection, substitution, etc. can be carried out, these steps being well known to the person skilled in the art.

The compound of formula (I) obtained can be recovered by separation from the reaction medium by methods well known to the person skilled in the art, such as by extraction, evaporation of the solvent or by precipitation or crystallisation (followed by filtration).

The compound can be also purified if necessary by methods well known to the person skilled in the art, such as by recrystallisation, by distillation, by chromatography on a column of silica gel or by high performance liquid chromatography (HPLC).

The process for preparing the compound of formula (XI) can comprise the following successive steps:

(a3) hydroboration-oxidation reaction of the compound of formula (XII)

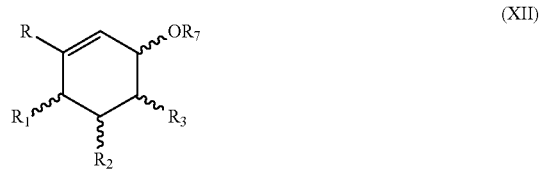

wherein R, $R_1$, $R_2$, and $R_3$ are as defined above and $R_7$=$SiR^{a1}R^{b1}R^{c1}$ or $CH_2OCH_3$ (methoxymethyl—MOM), with $R^{a1}$, $R^{b1}$ and $R^{c1}$ each representing independently a ($C_1$-$C_6$)-alkyl, aryl or aryl-($C_1$-$C_6$)-alkyl group, to give a compound of the following formula (XIII)

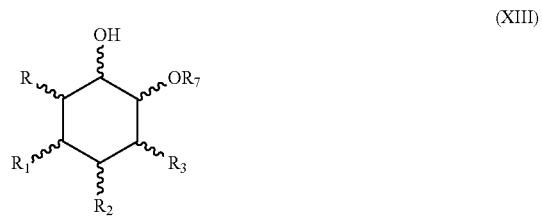

wherein R, $R_1$, $R_2$, and $R_3$ are as defined above and $R_7$=$SiR^{a1}R^{b1}R^{c1}$ or $CH_2OCH_3$ (methoxymethyl—MOM), (b3) oxidation of the compound of formula (XIII) obtained in previous step (a3) to give a compound of the following formula (XIV)

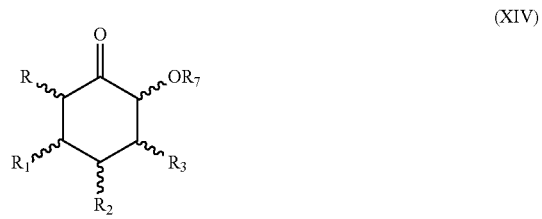

wherein R, $R_1$, $R_2$, and $R_3$ are as defined above and $R_7$=$SiR^{a1}R^{b1}R^{c1}$ or $CH_2OCH_3$ (methoxymethyl—MOM), (c3) when $R_7$=$SiR^{a1}R^{b1}R^{c1}$, deprotection of the compound of formula (XIV) obtained in previous step (b3) to give a compound of formula (XIV) with $R_7$=H, (d3) when $R_7$=H, protection of the compound of formula (XIV) with $R_7$=H obtained in previous step (c3) to give a compound of formula (XIV) with $R_7$=$COR_8$ with $R_8$ representing a ($C_1$-$C_6$)-alkyl, aryl or aryl-($C_1$-$C_6$)-alkyl group, (e3) fluorination of the compound of formula (XIV) with $R_7$=$COR_8$ or $CH_2OCH_3$ obtained in previous step (d3) or (b3) to give a compound of the following formula (XV)

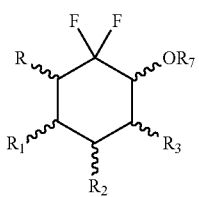

(XV)

wherein R, $R_1$, $R_2$, and $R_3$ are as defined above and $R_7$=$COR_8$ or $CH_2OCH_3$, (f3) deprotection of the compound of formula (XV) with $R_7$=$COR_8$ or $CH_2OCH_3$ obtained in previous step (e3) to give a compound of formula (XV) with $R_7$=H, and (g3) oxidation of the compound of formula (XV) with $R_7$=H obtained in previous step (f3) to give a compound of formula (XI).

Step (a3) corresponds to previous step (b1). Compound of formula (XII) can be prepared from compound of formula (IV) by a protection step, well known to the person skilled in the art.

Steps (b3) and (g3) can be carried out in the presence of an oxidant such as Dess-Martin periodinane, PCC (Pyridinium chlorochromate), etc.

Steps (c3) and (d3) are optional and required only when $R7$=$SiR^{a1}R^{b1}R^{c1}$ in the starting material of formula (XII).

Step (c3), (d3) and (f3) can be carried out in conditions well known to the person skilled in the art.

Step (e3) can be carried out in the presence of a fluorinating agent, such as DAST (diethylaminosulphurtrifluoride).

The present invention concerns also a process for preparing a compound of formula (I) according to the invention for which $R_4$=H comprising the following steps:

(a4) bromination of a compound of formula (I) with $R_4$=OH to give a compound of formula (I) with $R_4$=Br, and (b4) reduction of the compound of formula (I) with $R_4$=Br obtained in previous step (a4) to give a compound of formula (I) with $R_4$=H.

Step (a4) can be carried out in the presence of a brominating agent such as $SOBr_2$. The reaction is advantageously carried out also in the presence of a base such as pyridine. The starting material can be prepared according to the process described above to prepare compounds of formula (I) with $R_4 \neq H$.

Step (b4) can be carried out in the presence of a hydride such as $Bu_3SnH$.

The process to prepare compounds according to the invention with n=0 and $R_4$=OH or H will be better detailed below and in the following experimental part.

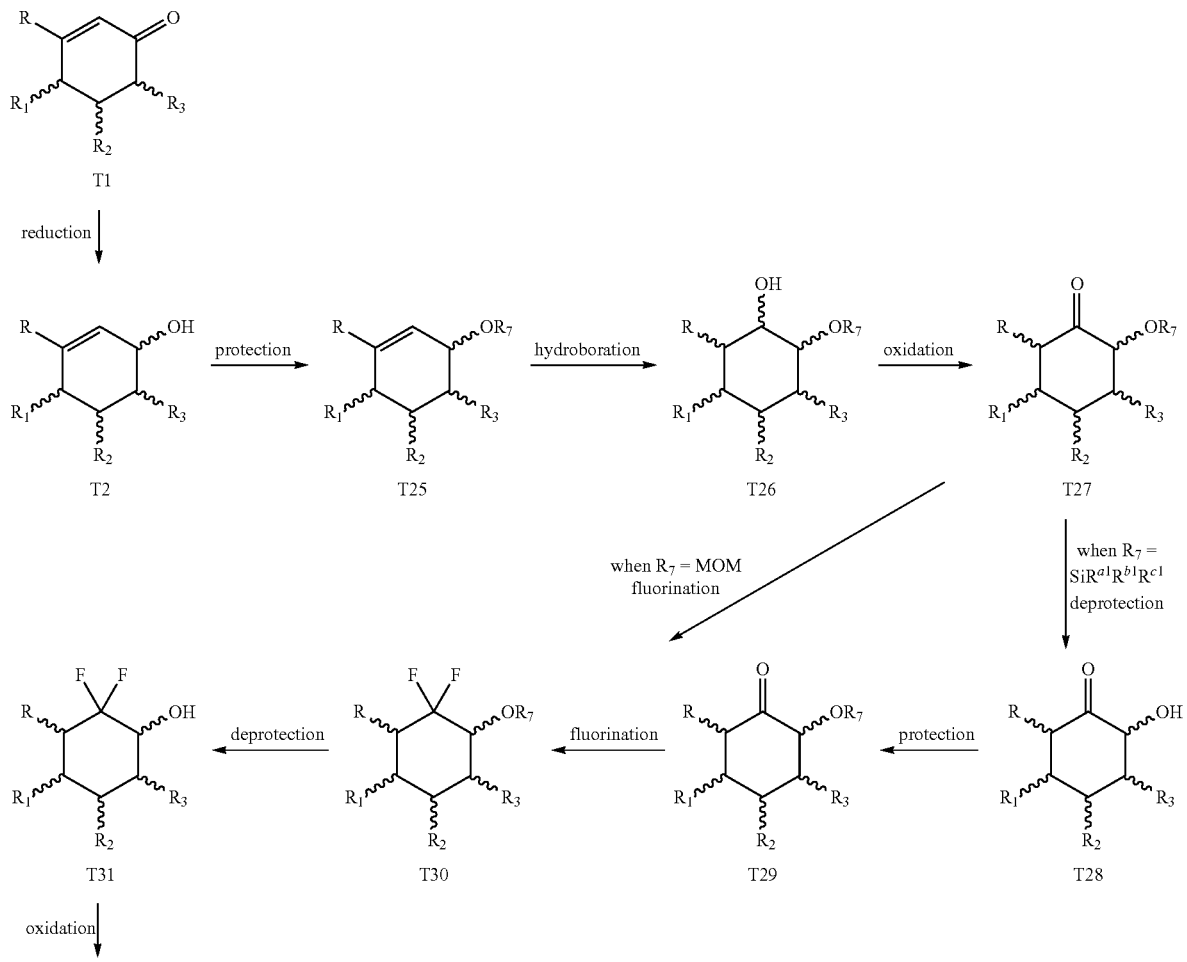

Scheme C: Synthesis of compounds with n = 0 and $R_4$ = OH or H

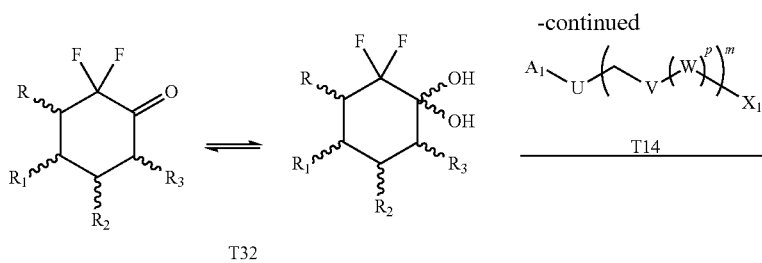

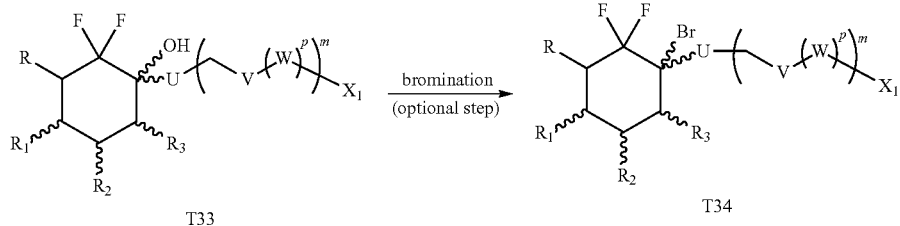

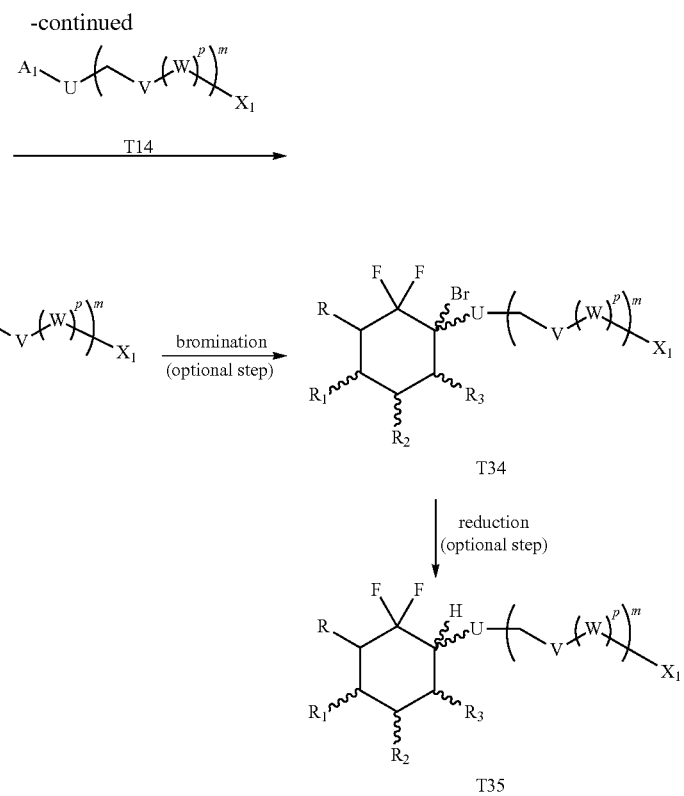

(a) In a first step cyclohexenone T1 undergoes a reduction involving standard conditions such as $NaBH_4$, $NaBH_4/CeCl_3$, $LiAlH_4$ or L-selectride.
(b) Alcohol T2 is then protected in the form of a silyl ether, according to well known procedures described in *Protective groups in organic synthesis*, T. W. Greene, to give compound T25.
(c) Hydroboration of compound T25 using $BH_3.Me_2S$ or $BH_3.THF$ leads to compound T26.
(d) Compound T26 is then oxidized into the corresponding ketone T27 according to typical procedures involving PCC, Dess-Martin periodinane, etc.
(e) When T27 bears a $R_7$ which is a silylated protective group, this silylated protective group of compound T27 is then removed under acidic conditions using typical procedures described in *Protective groups in organic synthesis*, T. W. Greene, to afford alcohol T28.
(f) This alcohol T28 is protected into an ester according to well known procedures described in *Protective groups in organic synthesis*, T. W. Greene, to give compound T29.
(g) Compound T27 (when $R_7$=MOM) or T29 is fluorinated using a fluorinated reagent such as DAST to afford the fluorinated compound no.

(h) The ether or ester protective group ($OR_7$) of compound T30 is removed under typical conditions described in *Protective groups in organic synthesis*, T. W. Greene, to afford alcohol T31.
(i) This alcohol T31 is then oxidized using Dess-Martin periodinane to afford compound T32.
(j) A Grignard reagent or lithiated compound T14, prepared from the corresponding halogenated compound according to a typical procedure, is added onto compound T32 to afford T33.
(k) Compound T33 is brominated according to typical procedures including the use of $SOBr_2$ followed by the addition of pyridine to afford compound T34.
(l) Compound T34 is then reduced in the presence of a hydride such as $Bu_3SnH$.
(m) In a last step, protective groups can be removed according to typical procedures described in *Protective groups in organic synthesis*, T. W. Greene.

It should be noted that steps (k) and (l) are carried out only for the preparation of a compound of formula (I) with $R_4$=H.

And more particularly:

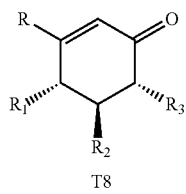

reduction ↓

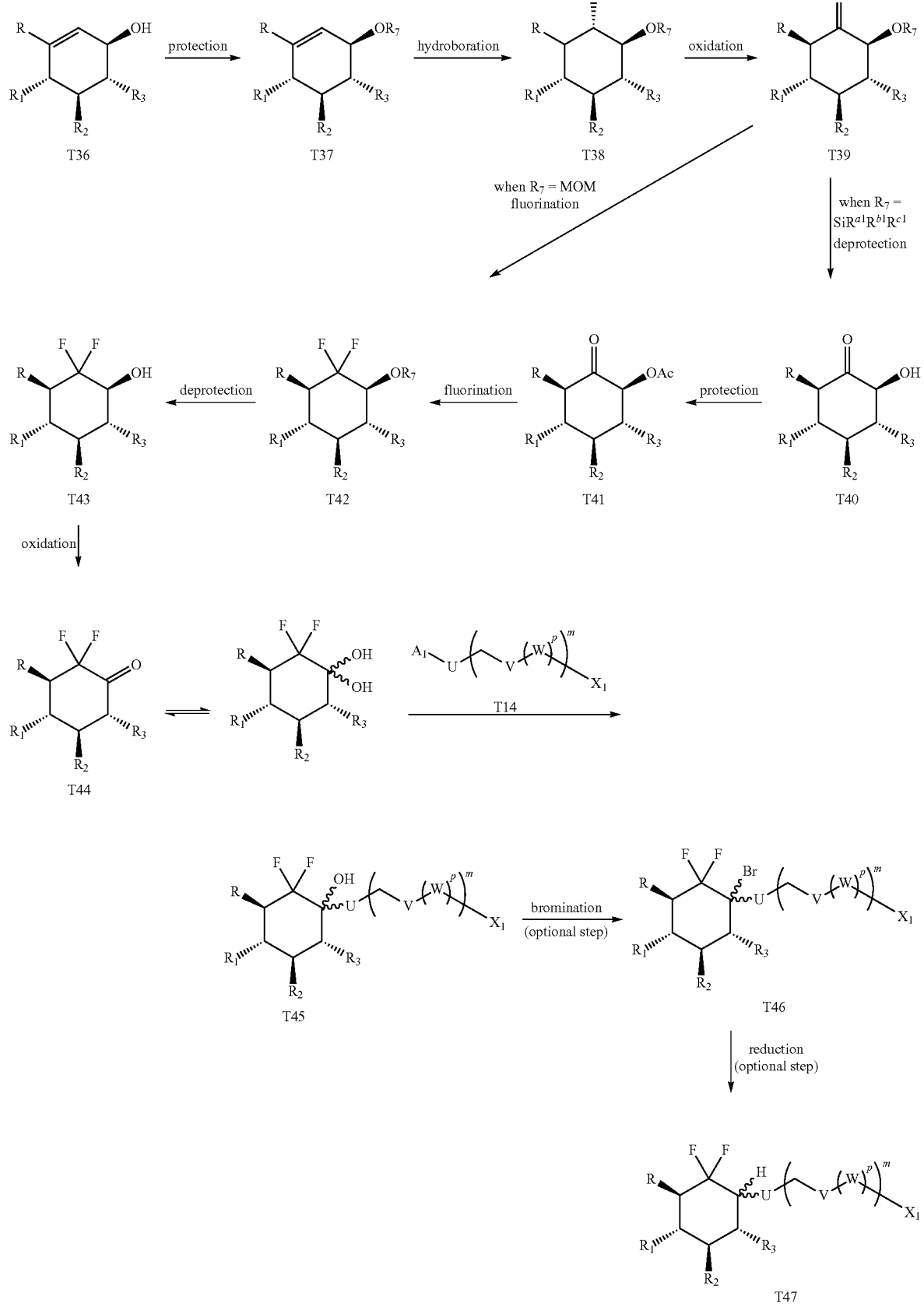

(a) In a first step cyclohexenone T8 undergoes a selective reduction involving $NaBH_4/CeCl_3$, in THF and MeOH.
(b) Alcohol T36 is then protected using imidazole and TBDMSCl to give compound T37 with $R_7$=TBDMS; or dimethoxymethane and $P_2O_5$ to give compound T37 with $R_7$=$CH_2OCH_3$.
(c) Hydroboration of compound. T37 using $BH_3.Me_2S$ leads to compound T38.
(d) Compound T38 is then oxidized into the corresponding ketone T39 according to typical procedures involving PCC, Dess-Martin periodinane, etc.
(e) When $R_7$=TBDMS, this silylated protective group of compound T39 is then removed under acidic conditions such as HCl 12N in methanol and dichloromethane to afford alcohol T40.
(f) This alcohol T40 is protected into an acetate using $Ac_2O$, pyridine and a catalytic amount of DMAP (Dimethylaminopyridine) to give compound T41.
(g) Compound T41 or compound T39 with $R_7$=$CH_2OCH_3$ is fluorinated using DAST in dichloromethane to afford the fluorinated compound T42.
(h) When $R_7$=Ac, the acetate protecting group of compound T42 is removed using sodium methanolate in methanol to afford alcohol T43.
When $R_7$=$CH_2OCH_3$, the MOM protective group of T42 is removed using TFA in dichloromethane to afford alcohol T43.
(i) This alcohol T43 is then oxidized using Dess-Martin periodinane to afford compound T44
(j) A Grignard reagent or a lithiated compound T14, prepared from the corresponding halogenated compound according to a typical procedure, is added onto compound T44 to give compound T45.
(k) Compound T45 is brominated with $SOBr_2$ in dichloromethane followed by the addition of pyridine to afford compound T46.
(l) Compound T46 is then reduced in the presence of $Bu_3SnH$ in toluene to give compound T47.
(m) In a last step, protective groups can be removed according to typical procedures described in *Protective groups in organic synthesis*, T. W. Greene.

It should be noted that steps (k) and (l) are carried out only for the preparation of a compound of formula (I) with $R_4$=H.

The present invention concerns also a process for preparing a compound of formula (I) according to the invention for which R4=H and n=1 comprising a coupling reaction between a compound of the following formula (XVI):

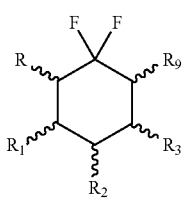

(XVI)

wherein R, $R_1$, $R_2$, and $R_3$ are as defined above and $R_9$ represents a leaving group, with a compound of formula (V) as defined above.

The term "leaving group" as used in the present invention refers to a chemical group which can be easily replaced with a nucleophile during a nucleophile substitution reaction, the nucleophile being in the present case an alcohol, i.e. a molecule carrying a group OH. Such a leaving group can be in particular a halogen atom or a sulfonate. The sulfonate is in particular a group —$OSO2$-R10 with R10 representing a (C1-C6alkyl), aryl, aryl-(C1-C6)-alkyl or (C1-C6)-alkyl-aryl group. The sulfonate can be in a mesylate (CH3-S(O2)O—), a triflate (CF3-S(O)2O—) or a tosylate (p-Me-C6H4-S(O)2O—).

This reaction can be carried out in conditions well known to the person skilled in the art, notably in the presence of a base such as NaH, $K_2CO_3$, or MeONa.

If necessary, additional steps of protection, deprotection, substitution, etc. can be carried out, these steps being well known to the person skilled in the art.

The compound of formula (I) obtained can be recovered by separation from the reaction medium by methods well known to the person skilled in the art, such as by extraction, evaporation of the solvent or by precipitation or crystallisation (followed by filtration).

The compound can be also purified if necessary by methods well known to the person skilled in the art, such as by recrystallisation, by distillation, by chromatography on a column of silica gel or by high performance liquid chromatography (HPLC).

The compound of formula (XVI) can be prepared from a compound of formula (XV) wherein $R_7$=H according to procedures well known to the person skilled in the art. For example, when the leaving group is a halogen atom, the reaction can be carried out in the presence of a halogenating agent. When the leaving group is a sulfonate, the reaction can be carried out in the presence of the corresponding sulfonic acid and a base such as pyridine.

The process to prepare compounds according to the invention with n=1 and $R_4$=H will be better detailed below and in the following experimental part.

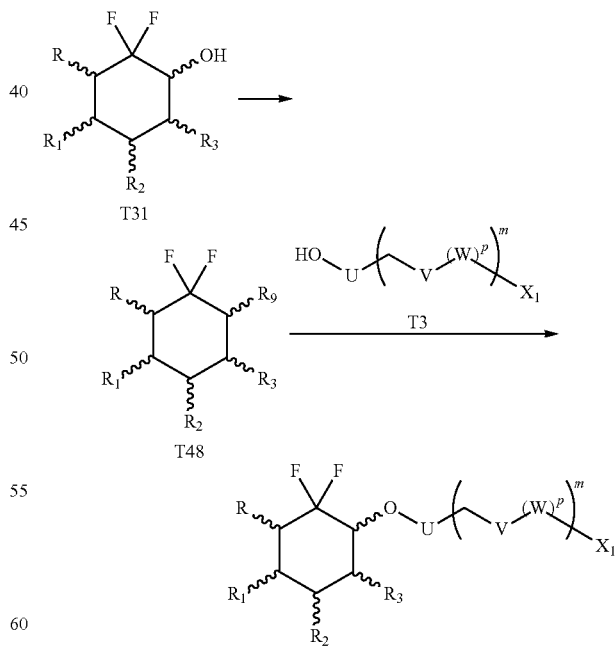

(a) In a first step, the alcohol group of T31 is converted into a leaving group such as a halogen or a mesyl, tosyl or trifluoromethanesulfonyl group according to procedures well known of the person skilled in the art.

(b) T48 is then substituted by the alcoholate generated from T3 by the use of a base such as NaH, K$_2$CO$_3$, or MeONa, to afford T7.

(c) In a last step, protective groups can be removed according to typical procedures described in *Protective groups in organic synthesis*, T. W. Greene.

And more particularly:

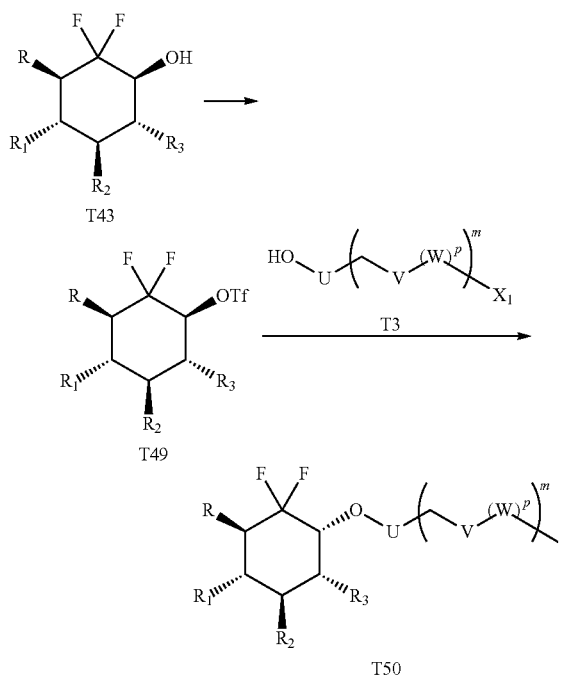

(a) In a first step, the alcohol group of T43 is converted into its corresponding trifluoromethanesulfonyl group in the presence of trifluoromethanesulfonic anhydride and pyridine to afford compound T49.

(b) T49 is then substituted by the alcoholate generated from T3 by the use of NaH to give T50. The reaction is performed in dimethylformamide.

(c) In a last step, protective groups can be removed according to typical procedures described in *Protective groups in organic synthesis*, T. W. Greene.

The invention will be better understood upon reading the following examples and figures, these examples serving solely to illustrate the invention.

FIGURES

FIG. 1 represents urinary glucose excretion for compound 16 and for compound 50 between 0 and 8 hours following oral administration (3 mg/kg po).

FIG. 2 represents urinary glucose excretion for compound 16 and for compound 50 between 16 and 28 hours following oral administration (3 mg/kg po).

Figure 5:
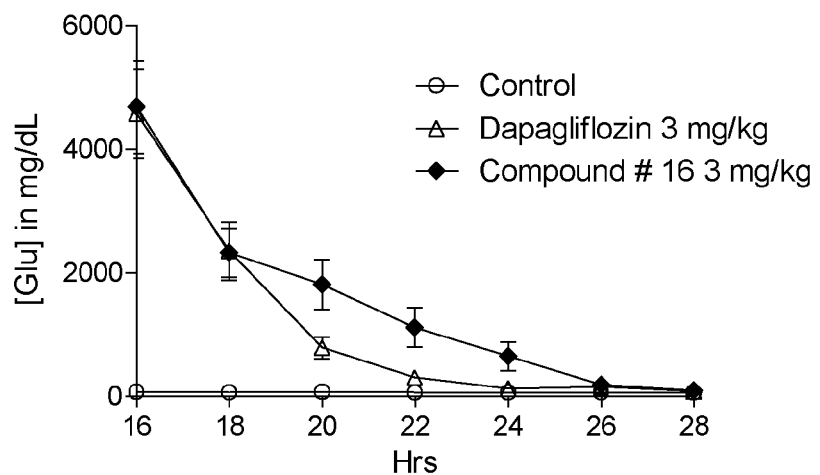

FIG. 5 represents urinary glucose excretion for compound 16 and for compound 50 between 16 and 28 hours following oral administration (3 mg/kg po).

Figure 6:
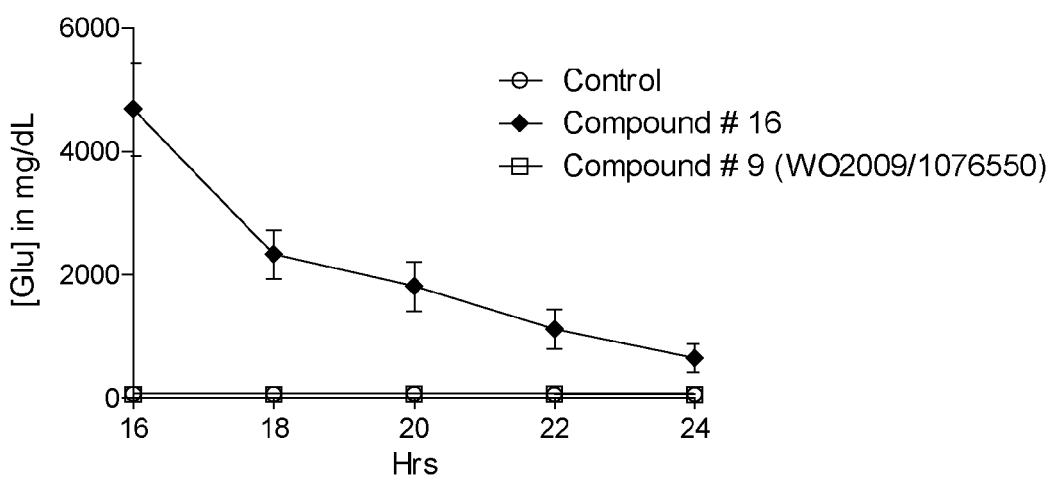

FIG. 6 represents urinary glucose excretion for compound 16 and for compound 9 of WO2009/1076550 between 16 and 28 hours following oral administration (3 mg/kg po).

Figure 7:
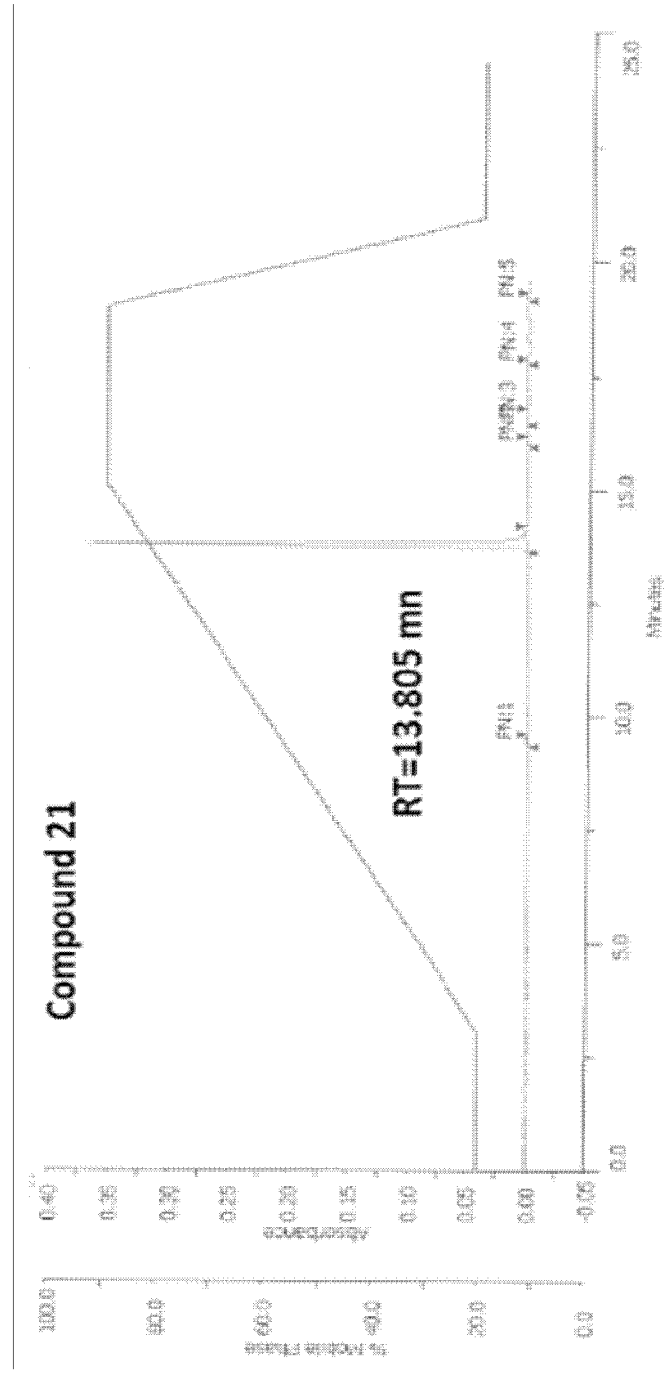

FIG. 7 represents the HPLC spectrum of compound M.

Figure 8:
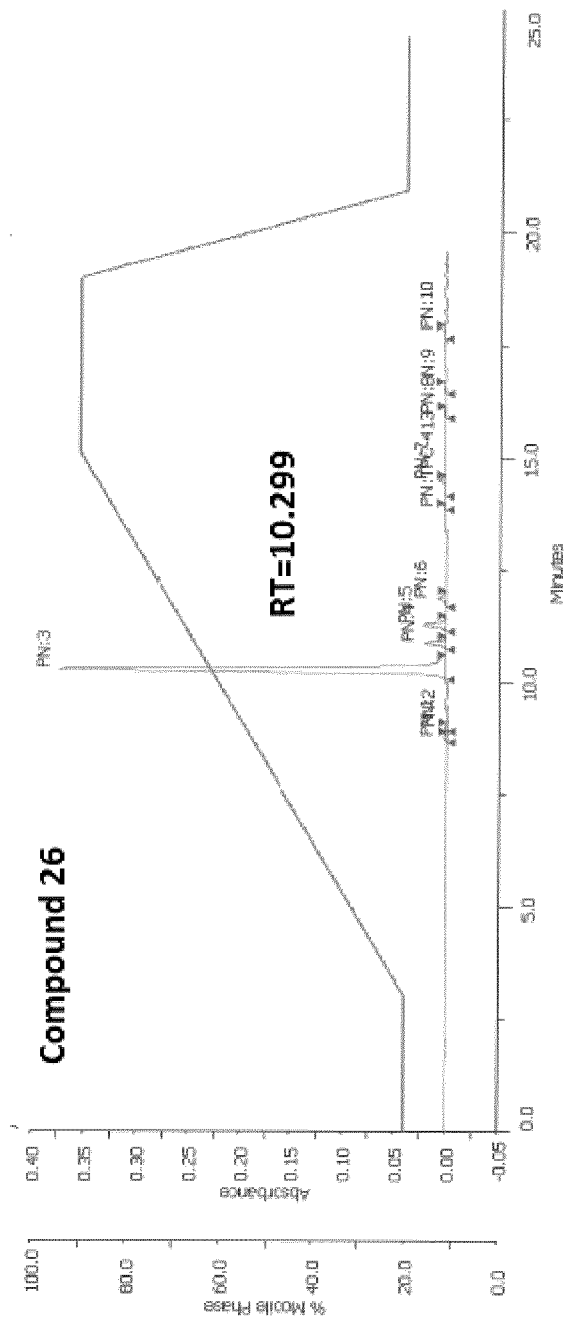

FIG. 8 represents the HPLC spectrum of compound 26.

Figure 9:
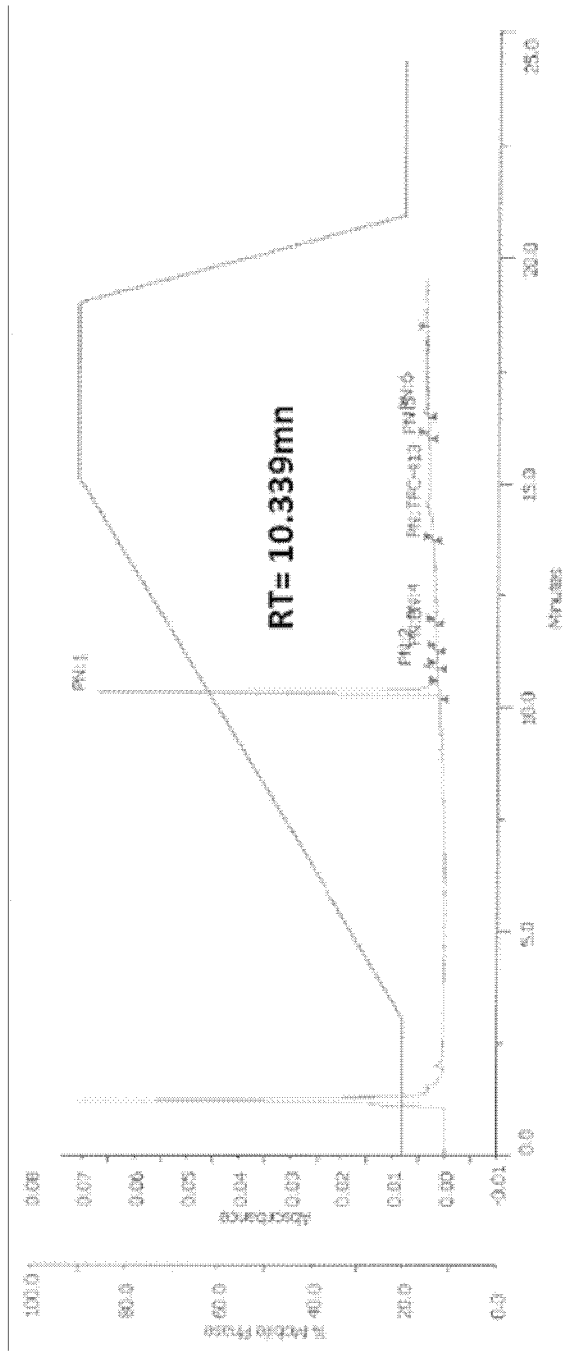

FIG. 9 represents the HPLC spectrum of compound 26 after 4 h of incubation at 37° C. in the presence of β-glucosidase.

Figure 10:
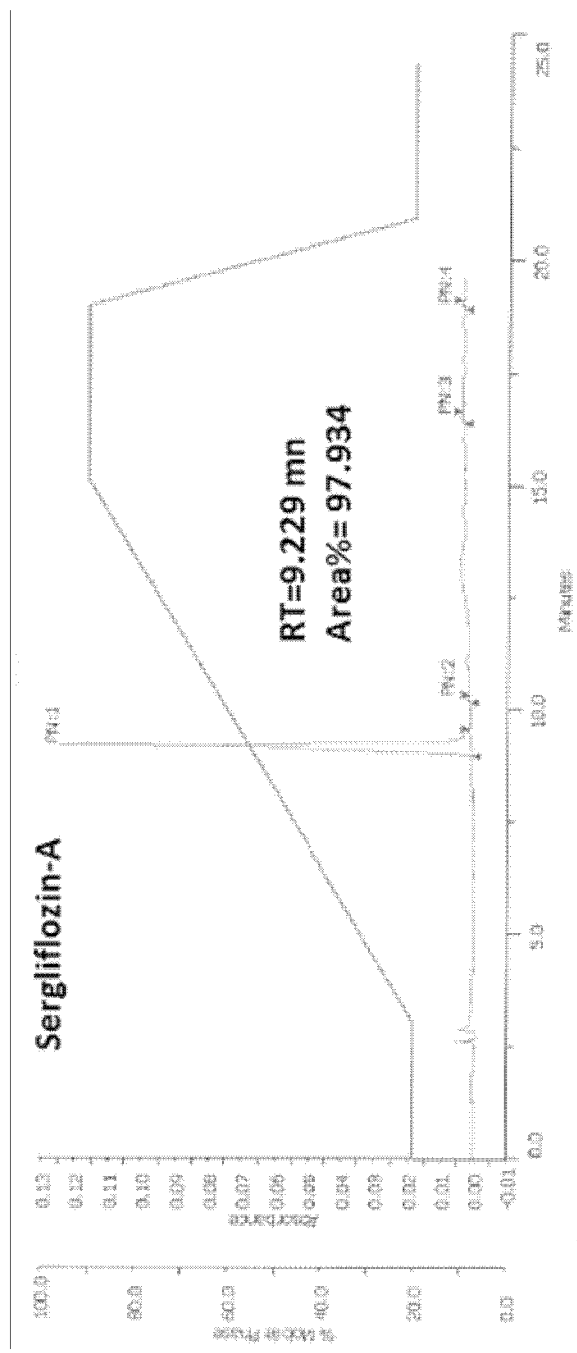

FIG. 10 represents the HPLC spectrum of Sergliflozin-A.

Figure 11:
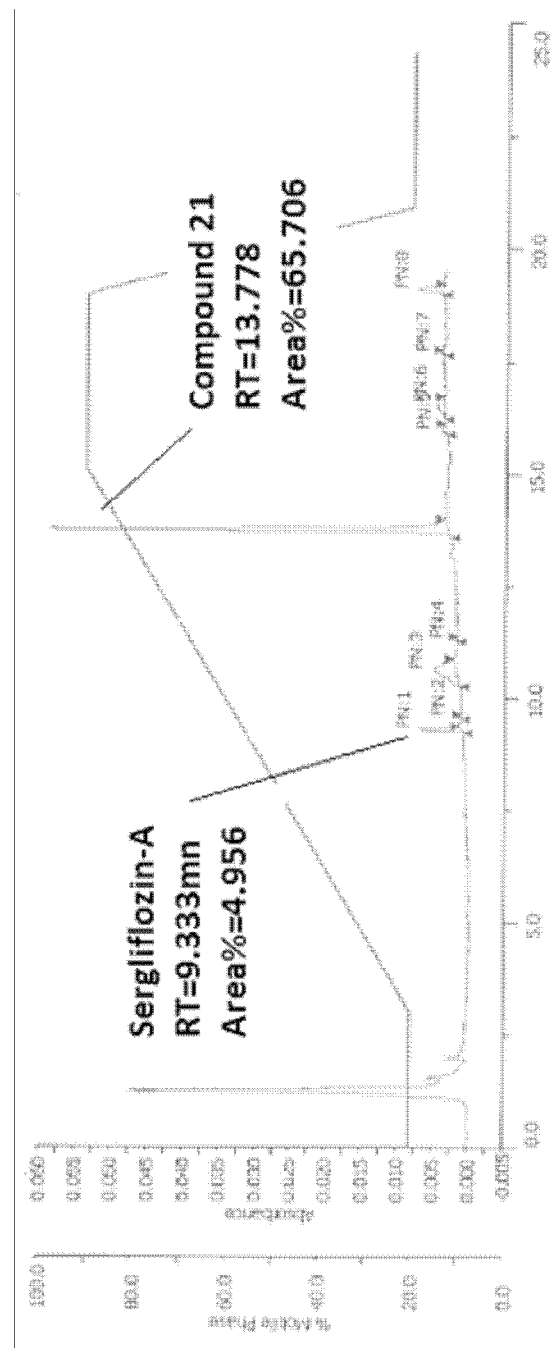

FIG. 11 represents the HPLC spectrum of Sergliflozin-A after 4 h of incubation at 37° C. in the presence β-glucosidase.

EXAMPLES

1. Preparation of the Compounds of the Invention

The abbreviations encountered are defined as follows:
Ac acetyl
ADDP azodicarboxylic acid dipiperidine
Bn benzyl
cat. Catalytic
DAST diethylaminosulphurtrifluoride
DCM dichloromethane
de diastereomeric excess
DMAP 4-Dimethylaminopyridine
DMF dimethylformamide
DMSO dimethylsulfoxide
eq. equivalent
ESI electrospray ionisation
g gram
Hz Hertz
mg milligram
MHz megahertz
min. minute
mL milliliter
mmol millimole
mM millimolar
μmol micromole
nmol nanomole
NMR Nuclear Magnetic Resonance
po per os
PEG Polyethylene glycol
QS Quantum Satis
Rf rate of flow
rt room temperature
TFAA trifluoroacetic anhydride
THF tetrahydrofurane
TLC Thin layer Chromatography
TMS trimethylsilyl
TBDMS Tert-butyldimethylsilyl The features of the devices used to conduct analyses of all of the compounds described in this application are indicated herein below:

The $^{19}$F NMR spectra were recorded on BRUKER DPX 300 spectrometer. The internal reference used is fluorotrichloromethane CFCl$_3$. Chemical shifts (δ) are expressed in parts per million (ppm), and coupling constants (J) in Hertz (Hz).

The following abbreviations were used:
s for singlet, bs for broad singlet, d for doublet, t for triplet, qdt for quartet, m for multiplet or massive, dd for doublet of doublet, etc.

The mass spectra were obtained on a spectrophotometer Waters LCT Premier XE coupled to a LC Waters Acquity.

GC-MS spectra were performed on a Micromass Autospec 8 kV, equipped with a GC HP 6890, Capillar column WCOT, HP 5 MS, 30 m, DI: 0.25 mm, at 50° C. (0.5 mn), from 50 to 280° C. at 10° C./mn, and 280° C. for 5 mn, with IE: 70 eV.

Automated column chromatography was performed on Biotage SP4 instruments using Biotage® SNAP cartridges. Follow-up is ensured via thin-layer chromatography (TLC) with Kieselgel 60E-254-0.25-mm plates. The ratio of the migration distance of a compound on a given support to the migration distance of an eluent is called the retardation factor (Rf).

Exemplary compound preparations according to the invention will be described hereinbelow, for non-limiting, illustrative purposes.

Synthesis of Compound 1

$C_{34}H_{34}O_6$ M=538.63 g·mol$^{-1}$
Mass: (ESI$^+$): 561.2 (M+Na)

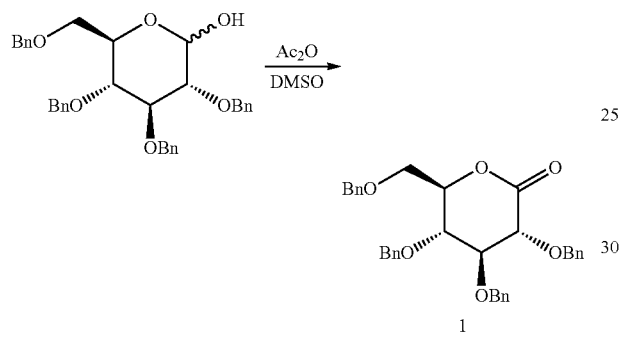

Acetic anhydride (420 mL) was added to a round bottom flask under inert atmosphere containing 2,3,4,6-tetra-O-benzyl-D-glucopyranose (100 g, 185 mmol) in DMS (640 mL). The mixture was stirred overnight at room temperature before being cooled to 0° C. A large volume of water was added and stirring was stopped so that the reaction mixture was allowed to settle for 3 h (the crude lactone lies at the bottom of the flask). The supernatant was removed and the crude mixture was diluted with $Et_2O$ and washed 3 times with water, neutralised with saturated aqueous solution of $NaHCO_3$ and washed again twice with water. The organic layer was then dried over magnesium sulphate, filtered and concentrated. The crude mixture was purified by silica gel chromatography (cyclohexane/ethyl acetate 8:2; Rf=0.61) to afford the desired lactone 1 as a colourless oil with 80% yield.

Synthesis of Compound 2

$C_{37}H_{43}O_9P$ M=662.71 g·mol$^{-1}$
Mass: (ESI$^+$): 685.33 [M+Na]$^+$; 1346.80 [2M+Na]$^+$

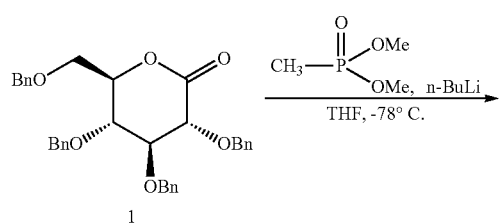

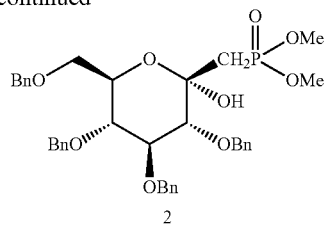

Under inert atmosphere, n-butyllithium (1.6M solution in hexanes, 168 mL, 0.27 mol, 2.9 eq) was added dropwise to a solution of dimethyl methyl-phosphonate (42 mL, 0.39 mol, 4.2 eq) in THF (390 mL) cooled to −78° C. The mixture was stirred for 30 minutes at this temperature before a solution of lactone 1 (50 g, 93 mmol, 1 eq) in tetrahydrofuran (230 mL) was added dropwise at the same temperature. The mixture was stirred for 30 minutes before being allowed to warm to 0° C. with stirring.

The reaction mixture was poured into an ice-cooled mixture of 10% saturated ammonium chloride aqueous solution (100 mL) and ethyl acetate (300 mL). The organic layer was separated, washed with water, dried over sodium sulphate, filtered and then concentrated under reduced pressure to afford quantitatively 3,4,5,7-tetra-O-benzyl-1-deoxy-1-(dimethoxyphosphoryl)-D-gluco-2-heptulopyranose 2 (63 g) as a slightly yellowish oil which gives white crystals overtime.

Synthesis of Compounds 3a/b $C_{37}H_{45}O_9P$ M=664.72 g·mol$^{-1}$
Mass: (ESI$^+$): 665.13 (M+H); 687.27 (M+Na); 696.73 (M+MeOH)

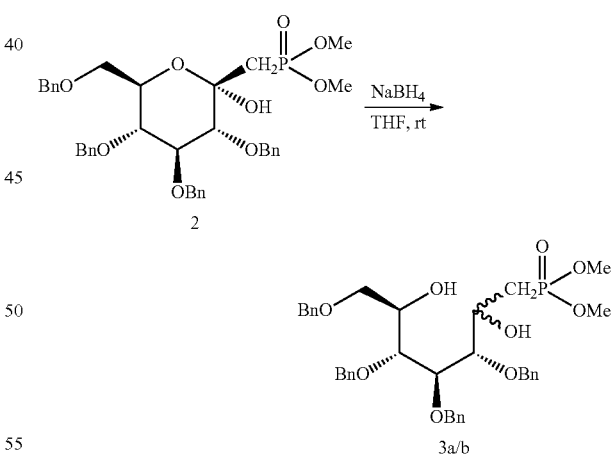

To a solution of 2 (69.5 g, 105 mmol, 1 eq) in tetrahydrofuran (600 mL) was added by portion sodium borohydride (7.44 g, 210 mmol, 2 eq). The mixture was stirred overnight at room temperature prior to be concentrated under reduced pressure. The residue was partitioned between ethyl acetate and water and the organic layer was washed with water, dried over sodium sulphate, filtered and concentrated under reduced pressure. The crude compound 3 (mixture of diastereomers a and b, 70.5 g, 100%) was engaged in the next step without further purification.

Synthesis of Compound 4

$C_{37}H_{41}O_9P$ M=660.69 g·mol$^{-1}$
Mass: (ESI$^+$): 661.00 (M+H); 683.20 (M+Na); 1343.0 (2M+Na)$^+$

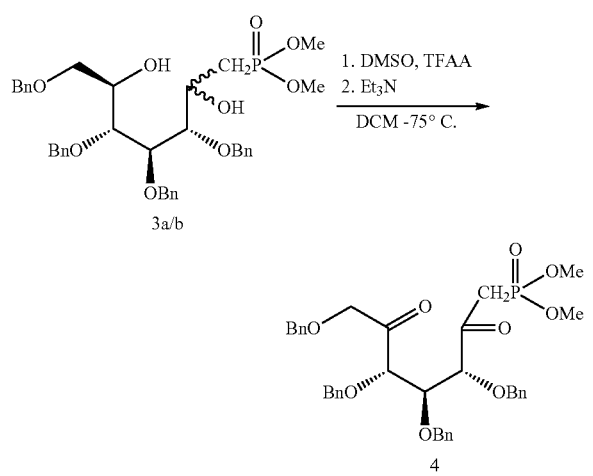

A solution of trifluoroacetic anhydride (27.1 mL, 0.19 mol, 4 eq) in dichloromethane (130 mL), cooled to 0° C. was added dropwise under inert atmosphere to a solution of dimethylsulfoxide (20.8 mL, 0.29 mol, 6 eq) in dichloromethane (260 mL) prepared at ambient temperature before being cooled to −75° C. The mixture was stirred for 45 minutes at −75° C., before a solution of 3 (32.43 g, 48.8 mmol, 1 eq) in dichloromethane (260 mL) cooled to −75° C. was added. The mixture was stirred for 1.5 h at the same temperature. Triethylamine (54.2 mL, 0.39 mmol, 8 eq) was added dropwise to the reaction mixture which was then allowed to warm to 0° C. with stirring. A 2N hydrochloric acid aqueous solution was added to the reaction mixture. The organic layer was separated, washed with a saturated sodium hydrogencarbonate solution, dried over sodium sulphate, filtered and concentrated under reduced pressure. The crude compound 4 (36.3 g, 100%), obtained in the form of a yellowish oil was engaged in the next step without further purification.

Synthesis of Compounds 5a/b $C_{35}H_{40}O_6$ M=556.69 g·mol$^{-1}$
Mass: (ESI$^+$): 557.20 (M+H); 1135.07 (2M+Na)

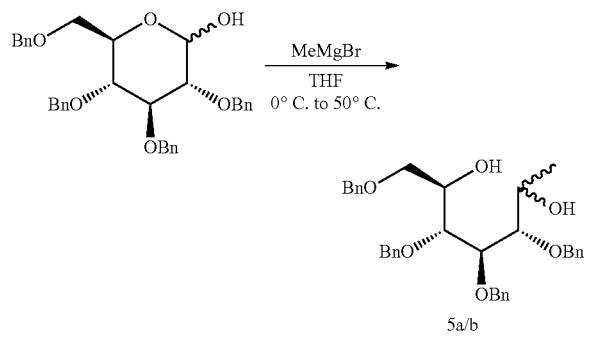

2,3,4,6-tetra-O-benzyl-D-glucopyranose (50 g, 92.7 mmol, 1 eq) was dissolved in THF (645 mL) and cooled to 0°. Methylmagnesium bromide (185 mL of a 1.4M solution in THF/toluene, 259.4 mmol, 2.8 eq) was added dropwise under inert atmosphere and the reaction mixture was stirred for 10 min at 0° C. and 3 h 30 at 50° C. TLC (cyclohexane-ethyl acetate, 7:3) showed complete conversion of starting material into two products (Rfa=0.17 and Rfb=0.25). The reaction mixture was poured into a saturated aqueous solution of ammonium chloride and extracted with ethyl acetate. The combined organic extracts were dried over sodium sulphate, filtered and concentrated to afford quantitatively the desired crude diol 5 (as a mixture of diastereomers a and b) in the form of yellow oil. This compound was engaged in the following step without further purification.

Synthesis of Compound 6

$C_{35}H_{36}O_6$ M=552.66 g·mol$^{-1}$
Mass: (ESI$^+$): 575.40 (M+Na); 575.40 (M+K); 1127.07 (2M+Na); 1142.93 (2M+K)$^+$.

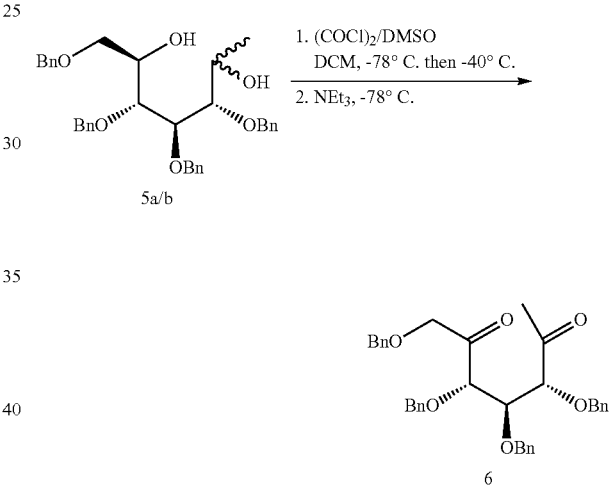

A solution of dimethylsulfoxide (14 mL, 0.20 mol, 9 eq) in dichloromethane (50 mL) was added dropwise to a solution of oxalyl chloride (12.5 mL, 0.13 mol, 6 eq) in dichloromethane (50 mL) cooled to −78° C., under inert atmosphere. The mixture was stirred at −78° C. for 30 min before a solution of diol 5 (12.2 g, 21.9 mmol, 1 eq) in dichloromethane (50 mL) was added dropwise. After 45 min, a precipitate appeared and the reaction mixture was warmed to −40° C. and stirred for an additional 30 min. The mixture was then re-cooled to −78° C. and triethylamine (55 mL, 0.39 mol, 18 eq) was added dropwise. After 15 min, the cooling bath was removed and the reaction mixture was allowed to reach room temperature. A large amount of precipitate had formed. After a further 2 h, toluene (400 mL) was added and the precipitate was removed by filtration. The residue was washed with toluene and the filtrate was concentrated and purified by silica gel chromatography (cyclohexane/ethyl acetate 97:3 to 70:30) to afford diketone 6 (9.92 g, 76% yield) as an orange oil.

Synthesis of Compound 7

$C_{35}H_{36}O_6$ M=552.66 g·mol$^{-1}$
Mass: (ESI$^+$): 570.27 (M+H$_2$O); 575.33 (M+Na)

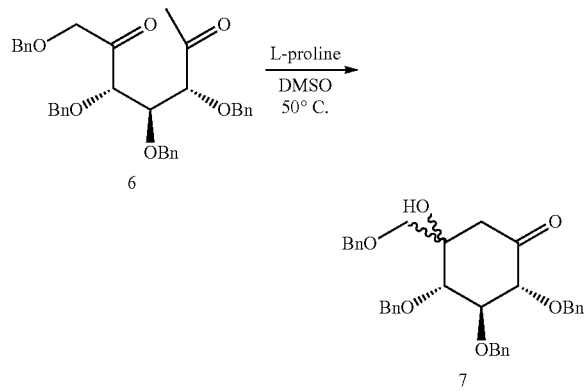

L-proline (7.35 g, 63.8 mmol, 1 eq) was added to a solution of diketone 6 (35.2 g, 63.7 mmol, 1 eq) in DMSO (561 mL). The mixture was stirred at 50° C. in air for 8 h before being poured into a mixture of water and brine (2:1), extracted with ethyl acetate, dried over sodium sulphate, filtered and concentrated. The crude mixture was purified on silica gel chromatography (cyclohexane/ethyl acetate 97:3 to 35:35) to afford compound 7 (13.0 g, 37%) as an orange oil.

Synthesis of Compound 8

$C_{35}H_{34}O_5$ M=534.64 g·mol$^{-1}$
Mass: (ESI$^+$): 535.00 (M+H); 552.00 (M+H$_2$O); 785.87; 1086.67 (2M+H$_2$O)

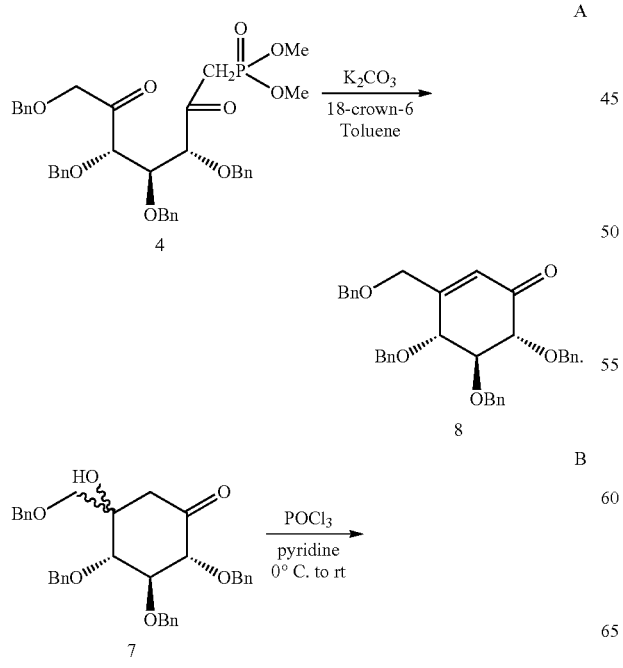

Procedure A:

To a solution of 4 (10.5 g, 15.89 mmol, 1 eq) in toluene (400 mL) were added 18-crown-6 (168 mg, 0.64 mmol, 0.04 eq) and potassium carbonate (6.69 g, 48.5 mmol, 3.05 eq.). The mixture was stirred overnight at room temperature, and then the remising insoluble material was filtered off and washed with toluene. The filtrate and the washings were combined, washed with 2N hydrochloric acid aqueous solution followed by saturated sodium hydrogencarbonate aqueous solution, dried over sodium sulphate, filtered and concentrated under reduced pressure. The residue was purified on silica gel chromatography (cyclohexane/ethyl acetate 98:2 to 80:20) to afford cyclohexenone 8 (4.07 g; 48% yield) as yellowish oil.

Procedure B:

A solution of 7 (3.27 g, 5.92 mmol, 1 eq) in pyridine (14 mL) was cooled to 0° C. before POCl$_3$ (2.75 mL, 29.6 mmol, 5 eq) was added dropwise. The mixture was stirred at this temperature for 10 min before the cooling bath was removed. The reaction mixture was stirred overnight at room temperature before being re-cooled to 0° C. POCl$_3$ (2.75 mL, 29.6 mmol, 5 eq) was added once again trying to complete the reaction. The mixture was stirred for an additional 20 h at room temperature before being diluted with Et$_2$O (20 mL) and poured onto crushed ice. 1M HCl aqueous solution (100 mL) was added, and the mixture was extracted with Et$_2$O (200 mL & 100 mL). The combined organic extracts were washed with brine (100 mL), dried over sodium sulphate, filtered and concentrated before being purified on silica gel chromatography (cyclohexane/ethyl acetate 98:2 to 80:20) to afford compound 8 (1.46 g, 46% yield) as an orange oil.

Synthesis of Compound 9

$C_{15}H_{12}BrClO_2$ M=339.61 g·mol$^{-1}$
Mass: (GC-MS): 338-340

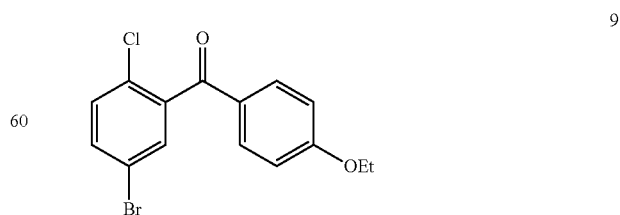

The synthesis of this product is described in *J. Med. Chem.* 2008, 51, 1145-1149.

Synthesis of Compound 10

C$_{15}$H$_{14}$BrClO M=325.63 g·mol$^{-1}$

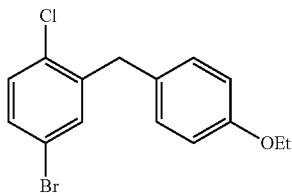

10

The synthesis of this product is described in *J. Med. Chem.* 2008, 5.1, 1145-1149.

Synthesis of Compound 11

C$_{50}$H$_{49}$ClO$_6$ M=781.37 g·mol$^{-1}$
Mass: (ESI$^+$): 798.20 (M+H$_2$O)

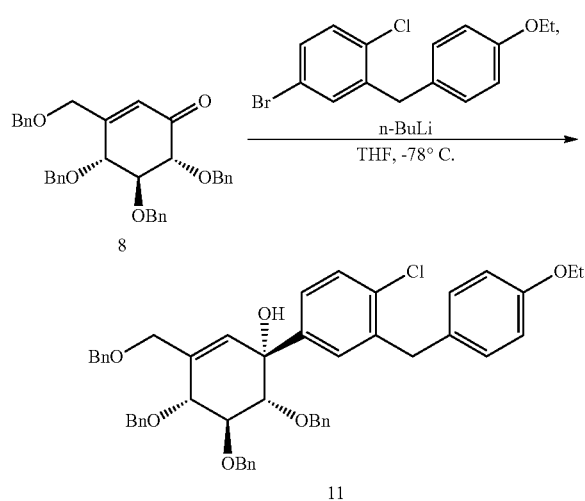

Under inert atmosphere, Mg powder (265 mg, 10.9 mmol, 2.44 was charged into a three necked flask, followed by addition of a portion of ⅓ of a solution of the 4-bromo-1-chloro-2-(4-ethylbenzyl)benzene (2.95 g, 9.1 mmol; 2 eq) in dry THF (25 mL) and 1,2-dibromoethane (10 mol % of Mg; 85 mg; 0.45 mmol). The mixture was heated to reflux. After the reaction was initiated (exothermic and consuming of Mg), the remaining solution of 2-(4-ethylbenzyl)-4-bromo-1-chlorobenzene in dry THF was added dropwise. The mixture was then allowed to react for another one hour under gentle reflux until most of the Mg was consumed.

The above Grignard reagent was added dropwise into the solution of cyclohexenone 8 (2.42 g, 4.53 mmol, 1 eq) in dry THF (25 mL) under inert atmosphere at room temperature (about 25° C.), then allowed to react for 3 h. A saturated aqueous solution of ammonium chloride was added into the mixture to quench the reaction. The mixture was extracted with Et$_2$O, washed with brine, dried over sodium sulphate, filtered and concentrated. The residue was purified on silica gel chromatography (cyclohexane/ethyl acetate 100:0 to 80:20) to afford the target compound 11 as a yellow oil (3.01 g, 86%).

Synthesis of Compound 12

C$_{50}$H$_{49}$ClO$_5$ M=765.37 g·mol$^-$
Mass: (ESI$^+$): 782.13 (M+H$_2$O)

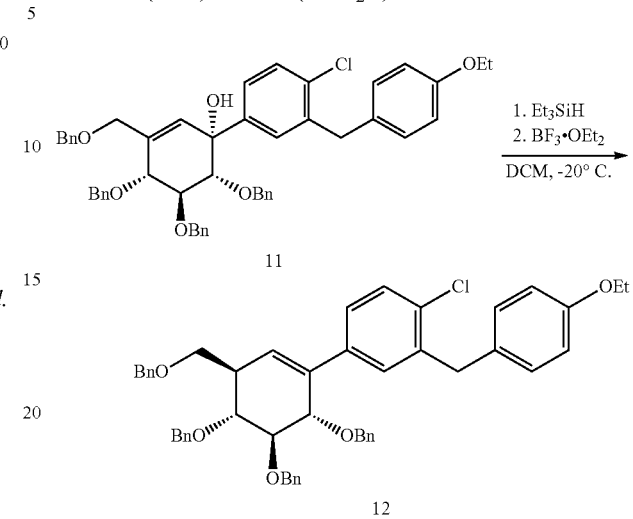

Triethylsilane (0.210 mL, 1.30 mmol, 3 eq) and boron-trifluoride etherate (48% BF$_3$, 0.110 mL, 0.866 mmol, 2 eq) were successively added into a solution of alcohol 11 (338 mg, 0.433 mmol, 1 eq) in dichloromethane (5 mL) under inert atmosphere at −20° C. After stirring for 2.5 h, a saturated aqueous solution of sodium chloride was added to quench the reaction. The mixture was extracted with CH$_2$Cl$_2$ (10 mL×3) and the organic layer was washed with brine, dried over Na$_2$SO$_4$, filtrated and concentrated. The residue was purified on silica gel chromatography (cyclohexane/ethyl acetate 9.8:0.2 to 8:2) to afford the target compound 12 as a white powder (278 mg, 0.363 mmol, 84%).

Synthesis of Compound 13

C$_{50}$H$_{51}$ClO$_6$ M=783.39 g·mol$^{-1}$
Mass: (ESI$^+$): 800 (M+H$_2$O); 1581 (2M+H$_2$O)

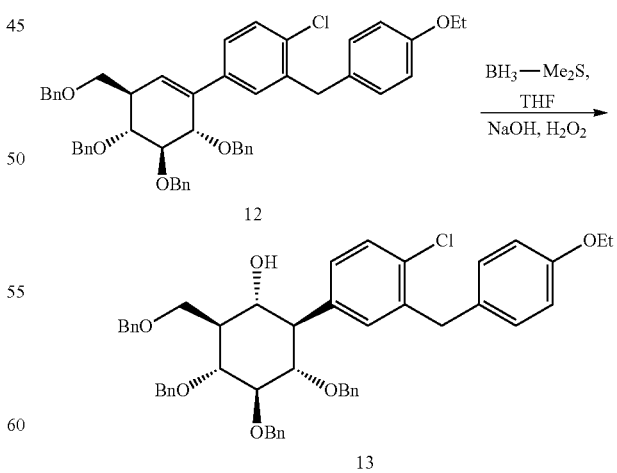

Under inert atmosphere, borane-dimethyl sulfide complex (2M in THF, 16.7 mL, 33 mmol, 10.5 eq) was added to a solution of 12 (2.41 g; 3.15 mmol, 1 eq) in dry THF (100 mL) cooled to 0° C. The reaction mixture was then refluxed for 1 h, cooled to 0° C. and treated carefully with sodium hydroxide (3M in H₂O, 10.5 mL, 31.5 mmol, 10 eq), followed by hydrogen peroxide (30% in H₂O, 3.2 mL, 31.5 mmol, 10 eq) at room temperature (above 30° C.). The mixture was allowed to react overnight at room temperature (~25° C.) before a saturated aqueous solution of ammonium chloride was added to quench the reaction. The mixture was extracted with ethyl acetate and the organic layer was washed with brine, dried over Na₂SO₄, filtered, and concentrated. The residue was purified by silica gel chromatography (cyclohexane/ethyl acetate 97:3 to 73:27) to afford the desired compound 13 (1.05 g; 43%) as a yellowish oil.

Synthesis of Compound 14

$C_{50}H_{49}ClO_6$ M=781.37 g·mol⁻¹
Mass: (ESI⁺): 798 (M+H₂O); 1471; 1579 (2M+H₂O)

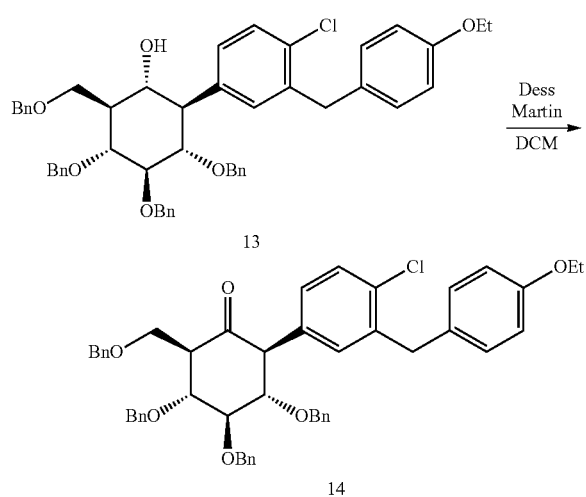

Dess-Martin periodinane (81 mg; 1.91 mmol; 1.5 eq) was added portion wise to a solution of alcohol 13 (1.0 g; 1.28 mmol, 1 eq) in anhydrous dichloromethane (20 mL) at 0° C. The reaction was then stirred overnight at room temperature before being quenched with 1N aqueous solution of sodium hydroxide. The organic layer was separated and the aqueous layer was extracted with dichloromethane. The combined organic layers were dried over sodium sulphate, filtered and concentrated. The residue was purified on silica gel chromatography (cyclohexane/ethyl acetate 98:2 to 82:18), to afford the target ketone 14 (783 mg, 79% yield) as a colorless oil.

Synthesis of Compound 15

$C_{50}H_{49}ClF_2O_6$ M=803.37 g·mol⁻¹
¹⁹F NMR (CDCl₃, 282.5 MHz): -100.3 (d, J=254 Hz, 1F, CFF); -113.3 (td, J1=254 Hz, J2=29 Hz, 1F, CFF).
Mass: (ESI⁺): 820.00 (M+H₂O)

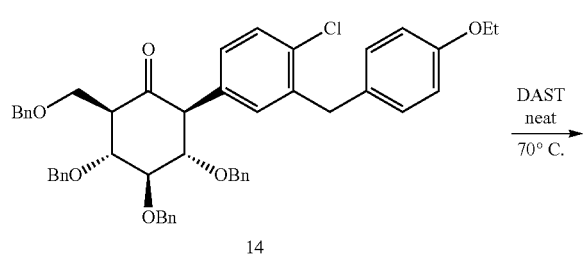

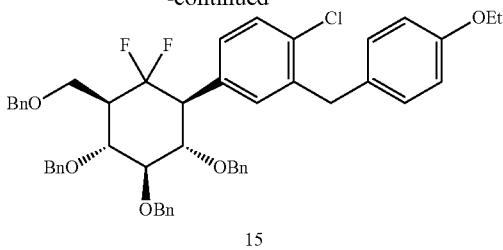

A solution of ketone 14 (421 mg, 0.539 mmol, 1 eq) in DAST (2 mL, 16.3 mmol, 30 eq.) was stirred under inert atmosphere at 70° C. for 12 h. The mixture was then cooled to room temperature and dichloromethane was added. The solution was poured on a mixture of water, ice and solid NaHCO₃. Agitation was maintained for 30 min while reaching room temperature. The aqueous layer was extracted with dichloromethane and the organic phase was dried over Na₂SO₄, filtered and concentrated. The crude product was purified on silica gel chromatography (cyclohexane/ethyl acetate 98:2 to 80:20) to afford the desired compound 15 as a yellowish oil (182 mg, 42% yield).

Synthesis of Compound 16

$C_{22}H_{25}ClF_2O_5$ M=442.88 g·mol⁻¹
¹⁹F NMR (MeOD, 282.5 MHz): -96.7 (d, J=254 Hz, 1F, CFF); -112.2 (td, J1=254 Hz, J2=28 Hz, 1F, CFF).
Mass: (ESI⁺): 465.3 (M+Na)

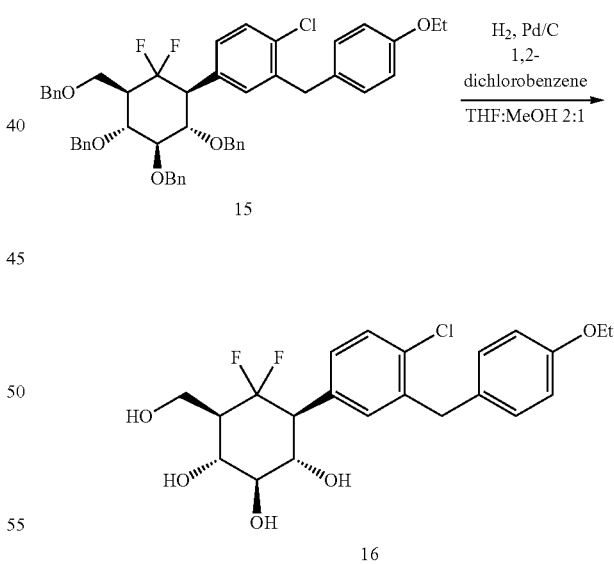

o-Dichlorobenzene (0.320 mL, 2.82 mol, 10 eq) followed by Pd/C 10% (0.342 g, 0.32 mol, 1.1 eq) were added to a solution of 15 (228 mg, 0.28 mmol, 1 eq) in a mixture of THF and MeOH (2:1, v/v, 160 mL). The reaction was placed under hydrogen atmosphere and stirred at room temperature for 2 h. The reaction mixture was filtered and concentrated before being purified on silica gel chromatography (dichloromethane/methanol 100:1 to 90:10) to afford compound 16 (105 mg, 83% yield).

Synthesis of Compound 17

$C_{35}H_{36}O_5$ M=536.66 g·mol$^{-1}$
Mass: (ESI$^+$): 554.13 (M+H$_2$O); 1095 (2M+Na)

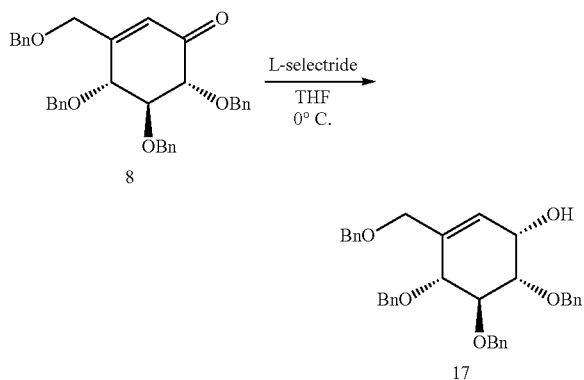

A 1M solution of L-selectride in THF (0.84 mL, 0.84 mmol, 1.5 eq), was added dropwise to a stirred and cooled (0° C.) solution of cyclohexenone 8 (0.300 g, 0.56 mmol, 1 eq) in THF (14 mL) under inert atmosphere. The mixture was stirred for 18 h allowing it to warm up to room temperature gradually. A saturated aqueous solution of ammonium chloride was then added and the resultant mixture was stirred for an additional 15 min. Water was added and the aqueous solution was then extracted with ethyl acetate and the combined organic layers were washed with brine, dried over sodium sulphate, filtered and concentrated to afford quantitatively the desired compound 17 (350 mg) as a yellow oil.

Synthesis of Compound 18

$C_{14}H_{12}O_3$ M=228.24 g·mol$^{-1}$
Mass: (GC-MS): 228 (M)

A.

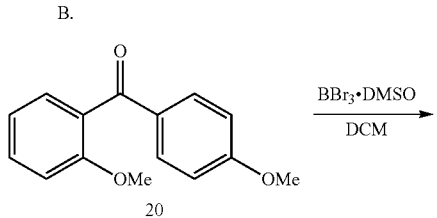

B.

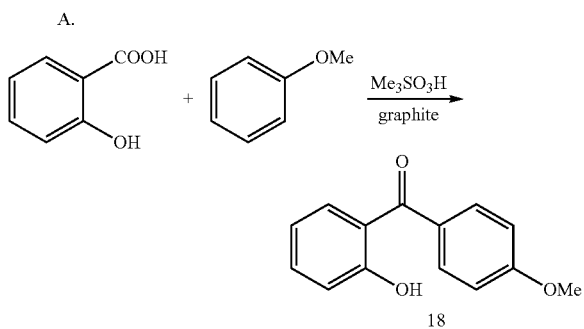

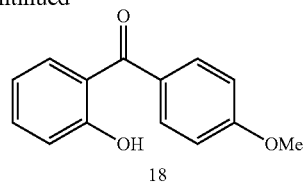

Procedure A.

2-Hydroxybenzoic acid (13.8 g, 0.1 mol, 1 eq) and anisole (10.9 mL, 0.1 mol, 1 eq) were added to a mixture of graphite (9.6 g, 0.8 mol, 8 eq) and methanesulfonic acid (25 mL, 0.4 mol, 4 eq) heated to 80° C. The reaction mixture was stirred at this temperature for 12 h before being cooled to room temperature. The mixture was then extracted twice with chloroform and the combined organic layers were washed with a saturated aqueous solution of NaHCO$_3$, dried over sodium sulphate, filtered and concentrated. The residue was purified on silica gel chromatography (cyclohexane/ethyl acetate 70:30) to afford compound 18 (4 g 17% yield) as an orange oil.

Procedure B.

BBr$_3$.DMSO (10.8 g, 34.42 mmol, 1.1 eq) was added portion wise to a solution of 20 (7.58 g, 31.29 mmol, 1 eq) in dichloromethane (150 mL) cooled to 0° C. The reaction was stirred at 0° C. for 3 h before being poured onto a mixture of water and ice. After 10 min stirring, the layers were separated and the aqueous layer was extracted with ethyl acetate. The combined organic layers ware washed with water and brine, dried over magnesium sulphate, filtered and concentrated to afford compound 18 (6.78 g) as a purple oil.

Synthesis of Compound 19

$C_{16}H_{16}O_3$ M=244.29 g·mol$^{-1}$
Mass: (ESI$^+$): 227.1 (M+H—H$_2$O)

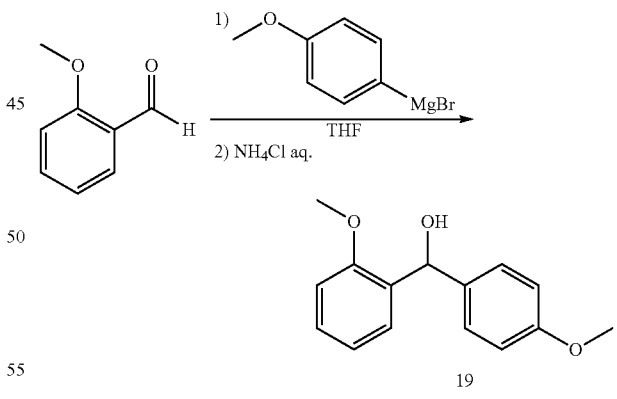

A solution of 4-methoxyphenylmagnesium bromide (0.5M in THF, 300 mL, 0.150 mol, 1.1 eq) was added drop wise under inert atmosphere to a solution of 2-methoxybenzaldehyde (18.75 g, 0.137 mol, 1 eq) in THF (188 mL) cooled to 0° C. The resulting mixture was stirred at room temperature overnight before being poured onto a saturated aqueous solution of NH$_4$Cl. The aqueous layer was extracted with ethyl acetate and the combined organic layers were dried over sodium sulphate, filtered and concentrated to afford compound 19 (37.5 g) as a brown oil.

Synthesis of Compound 20

$C_{15}H_{14}O_3$ M=242.27 g·mol$^{-1}$

Mass: (GC-MS): 51; 64; 77; 92; 107; 121; 128; 135; 139; 181; 197; 211; 225; 242

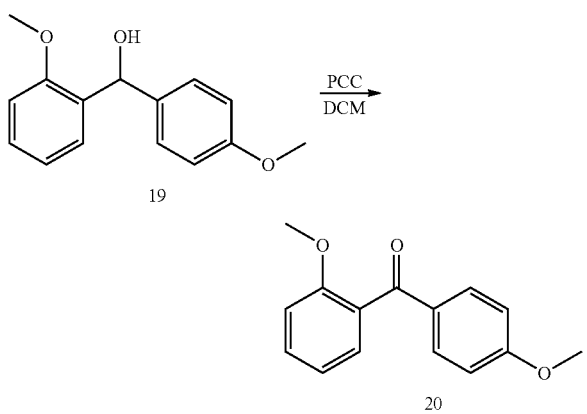

Pyridinium chlorochromate (34.3 g, 159 mmol, 2 eq) was added to a solution of alcohol 19 (19.4 g, 79.4 mmol, 1 eq) in dichloromethane (210 mL) containing molecular sieves. The reaction mixture was stirred overnight at room temperature, filtered to remove PCC residues and molecular sieves and concentrated. The crude residue was purified on silica gel chromatography (cyclohexane/ethyl acetate 100:0 to 85:15) to afford ketone 20 (12.6 g, 38% yield) as a yellowish solid.

Synthesis of Compound 21

$C_{14}H_{14}O_2$ M=214.26 g·mol$^{-1}$

Mass: (GC-MS): 214

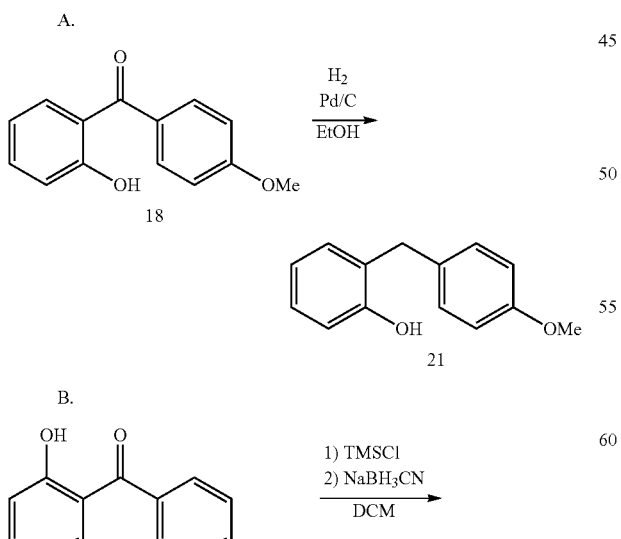

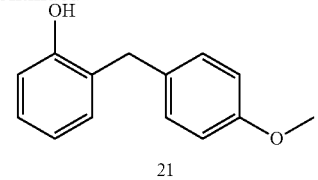

Procedure A.

10% Pd/C was added to a solution of 18 (1.5 g, 6.6 mmol, 1 eq) in ethanol. The solution was stirred under hydrogen atmosphere under 30 bars until completion of the reaction. Palladium particles were removed by filtration and the solution was concentrated to afford compound 21 (1.32 g, 93% yield) as a white powder.

Procedure B.

A solution of 18 (8.1 g, 35.5 mmol, 1 eq) in acetonitrile (130 mL) under inert atmosphere was cooled to 0° C. TMSCl (20.7 mL, 163.3 mmol, 4.6 eq) followed by NaBH$_3$CN (10.5 g, 1667 mmol, 4.7 eq) were slowly added (exothermic reaction). The resultant yellow suspension was stirred at room temperature for 2 h before being poured onto water. Dichloromethane was then added and the organic layer was separated, washed with brine, dried over magnesium sulphate, filtered and concentrated. The crude residue was purified on silica gel chromatography (cyclohexane/ ethyl acetate 100:0 to 83:17) to afford the target compound 21 (80% yield) as a yellowish solid.

Synthesis of Compound 22

$C_{49}H_{48}O_6$ M=732.90 g·mol$^{-1}$

Mass: (ESI$^+$): 755.4 (M+Na); 771.4 (M+K)

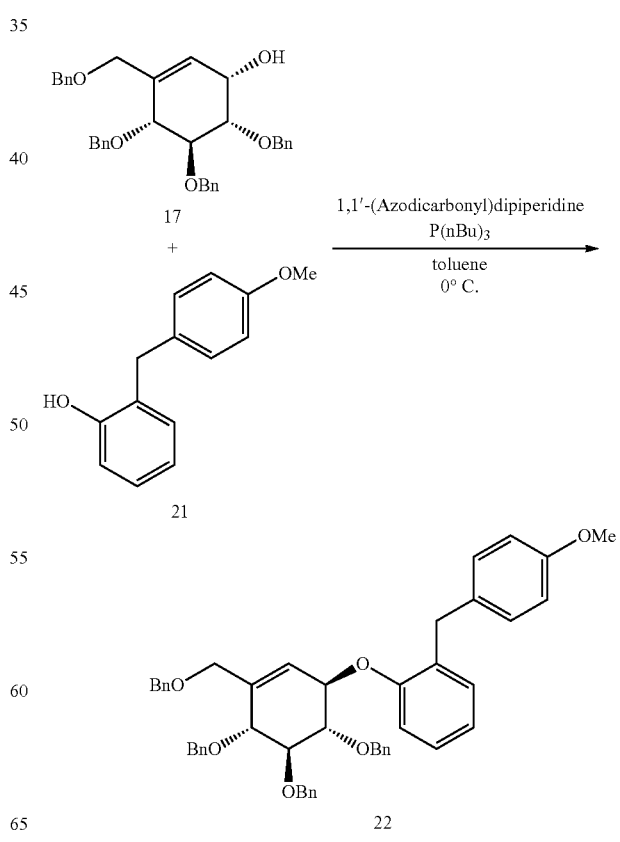

To a solution of 17 (50 mg, 0.093 mmol, 1 eq) in toluene (0.30 mL) cooled to 0° C. under inert atmosphere were successively added 21 (30 mg, 0.140 mmol, 1.5 eq), tributylphosphine (0.35 mL, 0.140 mmol, 1.5 eq) and 1,1'-(azodicarbonyl)dipiperidine (35 mg, 0.140 mmol, 1.5 eq). The reaction mixture was stirred at 0° C. for 30 min. A dense precipitate appeared and the mixture was dissolved with dichloromethane and concentrated under reduced pressure to give a white residue which was purified on silica gel chromatography (cyclohexane/ethyl acetate 100:0 to 80:20) to afford the target compound 22 (63 mg, 93% yield) as colorless oil.

Synthesis of Compound 23

$C_{49}H_{50}O_7$ M=750.92 g·mol$^{-1}$
Mass: (ESI$^+$): 7718 (M+Na); 789.7 (M+K)

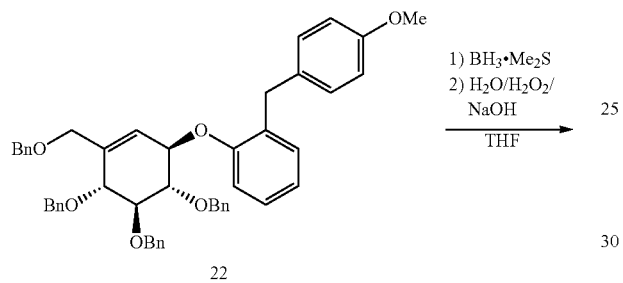

To a cooled solution (0° C.) of 22 (62 mg, 0.085 mmol, 1 eq) in anhydrous THF (0.837 mL) was added BH$_3$.Me$_2$S (2M solution in THF, 0.169 mL, 0.338 mmol, 4 eq). The resultant solution was stirred overnight at room temperature before being cooled again to 0° C. Water (0.107 mL, 23.6 mmol, 70 eq), hydrogen peroxide (30% aqueous solution, 0.258 mL, 10.1 mmol, 30 eq) and sodium hydroxide (2M aqueous solution, 0.338 mL, 2.7 mmol, 8 eq) were then successively added and the mixture was stirred at room temperature for 3 h. Water and ethyl acetate were added and the organic layer was washed with brine, dried over sodium sulphate, filtered and concentrated. The crude compound was then purified on silica gel chromatography (cyclohexane/ethyl acetate 100:0 to 75:25) to afford alcohol 23 (34 mg, 53% yield) as a white solid.

Synthesis of Compound 24

$C_{49}H_{48}O_7$ M=748.90 g·mol$^{-1}$
Mass: (ESI$^+$): 771.7 (M+Na); 787.7 (M+K)

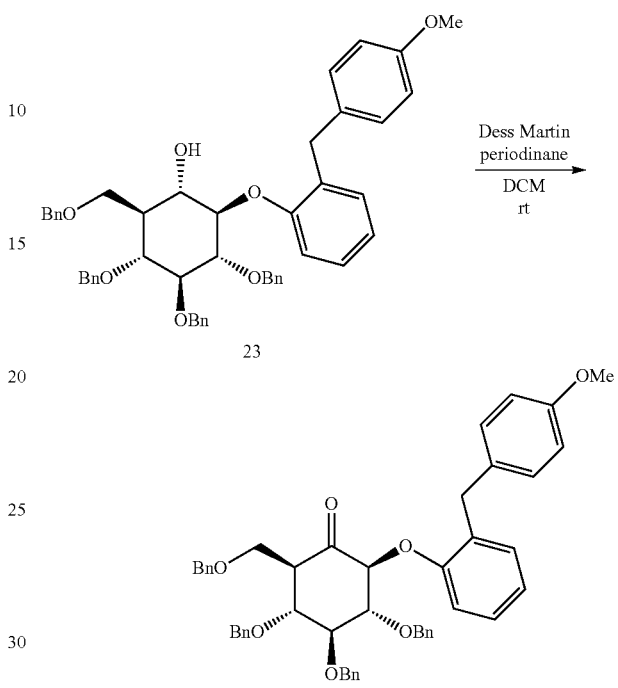

Dess Martin periodinane (29 mg, 0.068 mmol, 1.5 eq) was added to a solution of alcohol 23 (34 mg, 0.045 mmol, 1 eq) in dichloromethane (0.680 mL) cooled to 0° C. The resulting mixture was stirred at room temperature for 3 h before a solution of sodium hydroxide (1N aqueous solution) and dichloromethane were added to the mixture. The organic layer was separated, dried over sodium sulphate, filtered and concentrated to afford the desired ketone 24 (36 mg, 70% yield) as a white solid.

Synthesis of Compound 25

$C_{49}H_{48}F_2O_6$ M=770.90 g·mol$^{-1}$
$^{19}$F NMR (CDCl$_3$, 282.5 MHz): −109.3 (d, J=252 Hz, 1F, CFF); −120.3 (ddd, J1=252 Hz, J2=30 Hz, J3=19 Hz, 1F, CFF).
Mass: (ESI$^+$): 773.4 (M−HF); 793.5 (M+Na)

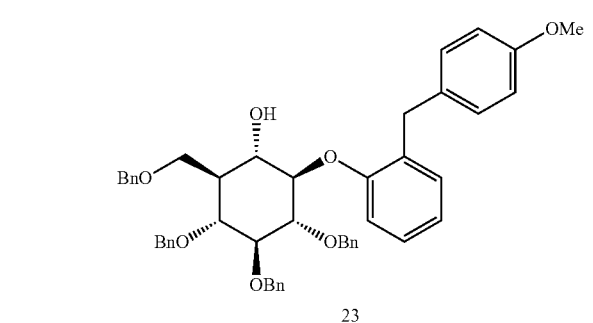

-continued

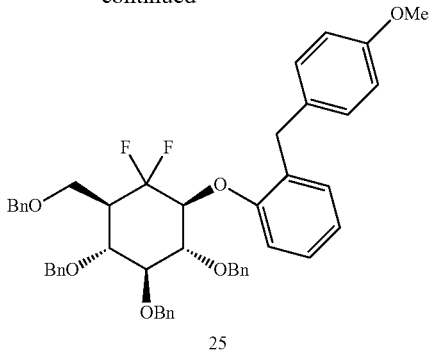
25

DAST (0.72 mL, 4.96 mmol, 20 eq) was added to a solution of ketone 24 (183 mg, 0.244 mmol, 1 eq) in dichloromethane (0.720 mL) under inert atmosphere and the reaction mixture was stirred overnight at room temperature. The solution was cooled to room temperature before being poured in water. Dichloromethane was added and the organic layer was washed with a saturated aqueous solution of NaHCO$_3$, dried over sodium sulphate, filtered and concentrated. The crude product was purified on silica gel chromatography (cyclohexane/ethyl acetate 100:0 to 90:10) followed by preparative HPLC (Kromasil C18, acetonitrile/water 89:11) to afford compound 25 in 32% yield as a white solid.

Synthesis of Compound 26

$C_{21}H_{24}F_2O_6$ M=410.41 g·mol$^{-1}$
$^{19}$F NMR (MeOD, 282.5 MHz): −109.6 (d, J=251 Hz, 1F CFF); −122.4 (ddd, J1=251 Hz, J2=28 Hz, J3=20 Hz, 1F, C FF).
Mass: (ESI$^-$): 445.2 (M+Cl)

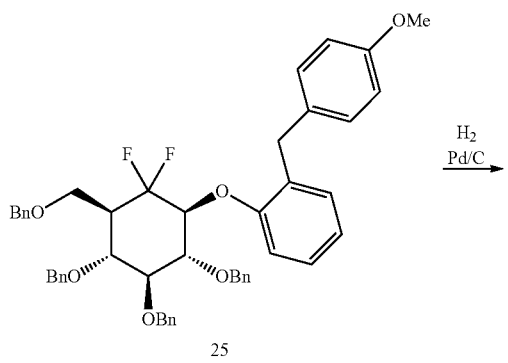

Compound 25 (48 mg, 0.06 mmol, 1 eq) was dissolved in a mixture of THF (6.3 mL) and methanol (6.3 mL) 10% Pd/C (48 mg, 0.04 mmol, 0.7 eq) followed by 2 drops of 12N aqueous solution of hydrochloric acid were added. The mixture was then stirred for 1 h under hydrogen atmosphere at room temperature before being filtered and concentrated. The crude mixture was purified on silica gel chromatography (dichloromethane/methanol 100:0 to 90:10) to afford the target compound 26 (42 mg, 67% yield) as a white solid.

Synthesis of Compound 27

$C_{48}H_{46}O_6$ M=718.88 g·mol$^{-1}$
Mass: (ESI$^+$): 741.8 (M+Na), 757.7 (M+K)

A solution of 17 (30 mg, 0.056 mmol, 1 eq) in toluene (0.180 mL) was cooled to 0° C. under an inert atmosphere and 4-(benzyloxy)phenol (17 mg, 0.085 mmol, 1.5 eq), tributylphosphine (0.42 mL, 0.168 mmol, 3 eq) and 1,1'-(azodicarbonyl)dipiperidine (42 mg, 0.167 mmol, 3 eq) were successively added. The reaction mixture was stirred at 0° C. for 30 min. The reaction mixture was diluted with dichloromethane and concentrated under reduced pressure to yield a white residue which was purified on silica gel chromatography (cyclohexane/ethyl acetate 100:0 to 80:20) to afford compound 27 (30 mg, 75% yield) as colorless oil.

Synthesis of Compound 28

$C_{48}H_{48}O_7$ M=736.88 g·mol$^{-1}$
Mass: (ESI+): 759.8 (M+Na), 775.7 (M+K)

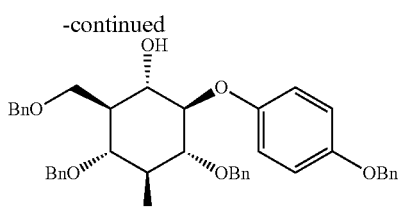

BH₃.Me₂S (3.48 mL, 6.96 mmol, 2 eq) was added, under inert atmosphere, to a solution of 27 (1.00 g, 1.39 mmol, 1 eq) in dry tetrahydrofuran (15 mL) cooled to 0° C. This mixture was stirred overnight at room temperature. Water (1.75 mL, 97.4 mmol, 70 eq) was then added at 0° C., followed by a 30% aqueous solution of H₂O₂ (4.73 mL, 41.7 mmol, 30 eq) and 1M aqueous solution of sodium hydroxide (11.1 mL, 11.1 mmol, 8 eq). The resultant mixture was stirred at room temperature for 3 hours. A large amount of water was then added, followed by extraction with EtOAc. The organic layer was washed with brine, dried over MgSO₄, filtered and concentrated. The crude mixture was purified by silica gel chromatography (cyclohexane/ethyl acetate 95:5 to 60:40) to afford 28 (791 mg, 78% yield) as a yellowish oil.

Synthesis of Compound 29

$C_{48}H_{46}O_7$ M=734.87 g·mol⁻¹

Mass: (ESI⁺): 757.8 (M+Na), 773.7 (M+K)

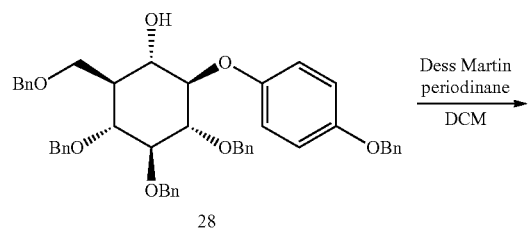

Dess-Martin periodinane (17 mg, 0.041 mmol, 1.5 eq) was added to a solution of alcohol 28 (682 mg, 1.61 mmol, 1 eq) in dry dichloromethane (20 mL) at room temperature. The reaction was stirred overnight at room temperature before being diluted with dichloromethane and quenched with a 1M aqueous solution of sodium hydroxide. After extraction with dichloromethane, the organic layer was dried over MgSO₄, filtered and concentrated to afford crude ketone 29 (730 mg, 91% yield) as a yellowish oil.

Synthesis of Compound 30

$C_{48}H_{46}O_7$ M=756.87 g·mol⁻¹

¹⁹F NMR (282.5 MHz): −120.6 (ddd, 1F, J1=251 Hz, J2=28 Hz, J3=20 Hz, CFF); −108.7 (d, 1F, J=251 Hz, CFF)

Mass: (ESI⁺): 779.3 [M+Na]⁺; 795.3 [M+K]⁺

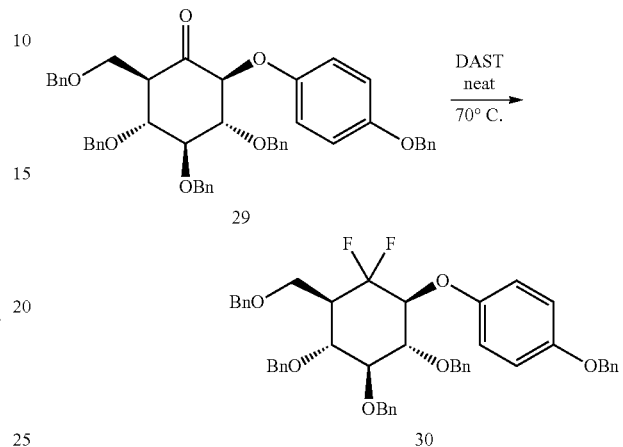

A solution of ketone 29 (15 mg, 2.04 μmol, 1 eq) in DAST (0.130 mL, 0.276 mmol, 130 eq) was stirred overnight under inert atmosphere at 70° C. The crude mixture was then diluted with dichloromethane and quenched carefully with H₂O. The organic layer was washed with a saturated aqueous solution of NaHCO₃, dried over MgSO₄, filtered and concentrated. The crude mixture was purified by preparative TLC (cyclohexane/ethyl acetate 85:15) to afford compound 30 as a yellowish oil.

Synthesis of Compound 31

$C_{13}H_{16}F_2O_6$ M=306.26 g·mol⁻¹

¹⁹F NMR (MeOD, 282.5 MHz): −109.2 (d, J=253 Hz, 1F, CFF); −123.0 (ddd, J1=253 Hz, J2=29 Hz, J3=20 Hz, 1F, CFF).

Mass: (ESI⁻): 341.0 [M+Cl]⁻

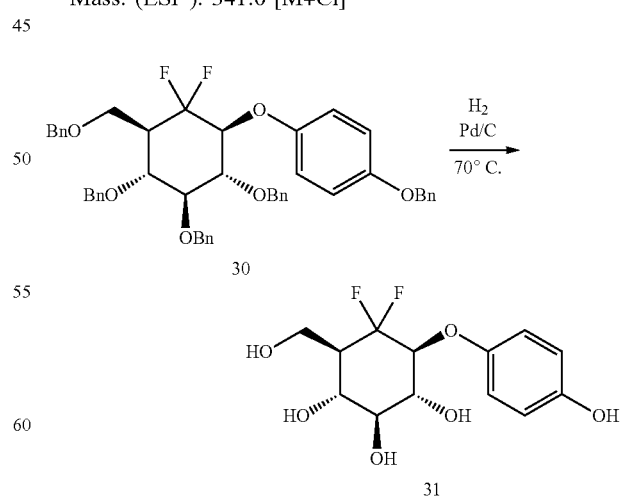

Compound 30 (191 mg, 0.252 mmol, 1 eq) was dissolved in a THF-ethanol (4:1, v/v, 120 mL) under inert atmosphere. 10% Pd/C (191 mg, 0.17 mmol, 0.7 eq) and 9 drops of 12N aqueous solution of hydrochloric acid were added to the mixture which was degassed 5 times with H$_2$. The resultant black suspension was stirred under an atmosphere of H$_2$ at room temperature for 45 min. The reaction mixture was filtered and the filtrate was concentrated. The crude product was purified on silica gel chromatography (dichloromethane/Methanol 100:0 to 90:10) to afford the target compound 31 in 73% yield as a colorless oil.

Synthesis of Compound 32

C$_{14}$H$_{12}$O$_2$ M=212.24 g·mol$^{-1}$
Mass: (CI$^+$): 213 (M+H)

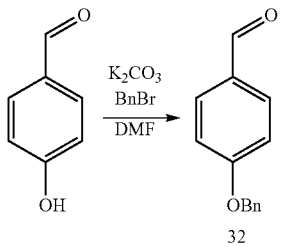

4-Hydroxybenzaldehyde (4 g, 32.8 mmol, 1 eq) and potassium carbonate (4.75 g, 34.4 mmol, 1.05 eq) were dissolved in dry DMF (30 mL). Benzyl bromide (4.1 mL, 34.4 mmol, 1.05 eq) was slowly added. The resultant mixture was stirred overnight under inert atmosphere at room temperature. Iced water was added to the reaction mixture to quench the reaction and which was then diluted with a large amount of water. The mixture was filtered and the residue was washed with water and dissolved in ethyl acetate. The organic layer was washed with brine, dried over MgSO$_4$, filtered and concentrated to give quantitatively crude aldehyde 32 as a yellowish oil which slowly crystallizes overtime.

Synthesis of Compound 33

C$_{14}$H$_{12}$O$_2$ M=21.4.26 g·mol$^{-1}$
Mass: (GC-MS): 91; 197; 214 (M).

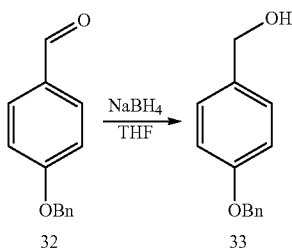

A solution of aldehyde 32 (6.5 g, 30.6 mmol, 1 eq) in dry tetrahydrofuran (25 mL) was added dropwise to a suspension of NaBH$_4$ (1.51 g, 39.8 mmol, 1.3 eq) in anhydrous tetrahydrofuran (25 mL). The resultant mixture was stirred 72 hours under inert atmosphere at room temperature before being quenched with iced water, diluted with diethyl ether, acidified with an aqueous solution of HCl 4N, and extracted with diethyl ether. The organic layer was washed with a saturated aqueous solution of NaHCO$_3$, dried over MgSO$_4$, filtered and concentrated to give crude alcohol 33 (97% yield) as a white amorphous solid.

Synthesis of Compound 34

C$_{14}$H$_{13}$BrO M=277.16 g·mol$^{-1}$
Mass: (CI+): 107; 197, 277 (M+H)

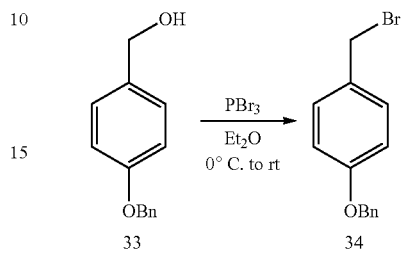

To an ice-cold suspension of crude alcohol 33 (6 g, 28.0 mmol, 2.4 eq.) in diethyl ether (50 mL), was added. PBr$_3$ (1.1 mL, 11.67 mmol, 1 eq) at a rate such that the temperature did not exceed 8° C. The resultant mixture was stirred 2 hours under inert atmosphere at room temperature. The reaction mixture was then cooled in an ice-bath, quenched with iced water and diluted with diethyl ether and ethyl acetate. The organic layer was washed with an aqueous saturated solution of NaHCO$_3$, dried over MgSO$_4$, filtered and concentrated to give crude compound 34 (99% yield) as a white amorphous solid.

Synthesis of Compound 35

C$_{20}$H$_{22}$O$_4$ M=326.39 g·mol$^{-1}$
Mass: (ESI$^+$): 349.1 (M+Na); 365.1 (M+K)

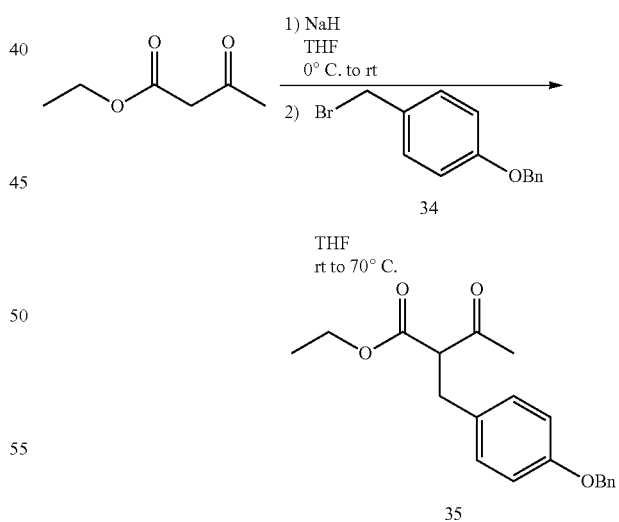

To a suspension of NaH 95% (0.61 g, 25.26 mmol, 1 eq) in dry THF (30 mL) under inert atmosphere, was added a solution ethylacetoacetate (3.5 mL, 27.79 mmol, 1.1 eq) in dry THF (10 mL) The resultant mixture was stirred 30 minutes at room temperature before adding dropwise a solution of 34 (7 g, 25.26 mmol, 1 eq) in THF (13 mL). The mixture was then stirred overnight at 70° C. and cooled to room temperature prior to be concentrated. The residue was

Synthesis of Compound 36

C$_{18}$H$_{18}$N$_2$O$_2$ M=294.35 g·mol$^{-1}$

Mass: (ESI$^+$): 317.1 (M+Na); 333.1 (M+K)

To a solution of 35 (6.5 g, 19.91 mmol, 1 eq) in ethanol (50 mL) was added hydrazine hydrate 55% (1.25 mL, 22.10 mmol, 1.1 eq) at room temperature. The resultant mixture was refluxed 3 hours at room temperature. The reaction media was then cooled in an ice bath and filtered. The precipitate was washed with cold ethanol to afford compound 36 (77% yield) as a white solid.

Synthesis of Compound 37

C$_{53}$H$_{52}$N$_2$O$_6$ M=812.99 g·mol$^{-1}$

Mass: (ESI$^+$): 813.5 (M+H); 835 (M+Na); 851.4 (M+K).

Compound 36 (328 mg, 1.11 mmol, 1.5 eq) was added to a solution of 17 (400 mg, 0.75 mmol, 1 eq) in dry THF (6.4 mL) under inert atmosphere followed by tri-n-butylphosphine (198 mg, 0.98 mmol, 1.3 eq) and azodicarboxylic acid dipiperidine (376 mg, 1.49 mmol, 2.0 eq). The resultant yellow suspension was stirred at 30° C. overnight. The solvent was removed and the crude mixture was purified on silica gel chromatography (cyclohexane/ethyl acetate 100:0 to 60:40) to afford compound 37 (262 mg, 43% yield) as a yellowish oil.

Synthesis of Compound 38

C$_{56}$H$_{58}$N$_2$O$_6$ M=855.07 g·mol$^{-1}$

Mass (ESI$^+$): 854.43 (M+Na); 893.5 (M+K).

Cesium carbonate (4.1 g, 12.5 mmol, 15 eq) followed by isopropyl iodide (0.99 g, 5.83 mmol, 7 eq) were added to a solution of 37 (0.68 g, 0.83 mmol, 1 eq) in DMF under inert atmosphere. The resultant suspension was stirred at room temperature for 3 h. The mixture was diluted with ethyl acetate and water. The organic layer was washed with brine, dried over sodium sulphate, filtered and concentrated. The crude yellow oil was purified on silica gel chromatography (cyclohexane/ethyl acetate 100:0 to 77:23) to afford the desired compound 38 (549 mg, 77% yield) as a yellowish oil.

Synthesis of Compound 39

$C_{56}H_{60}N_2O_7$ M=873.08 g·mol$^{-1}$

Mass (ESI$^+$): 873.6 (M+H); 895.6 (M+Na); 911.5 (M+K)

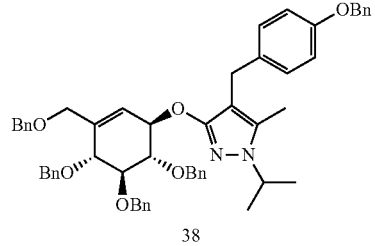

38

1) BH$_3$·Me$_2$S
2) H$_2$O/H$_2$O$_2$/NaOH
THF

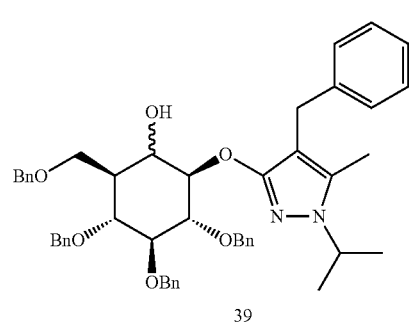

39

A solution of 9-BBN (0.5M in THF, 0.585 mL, 029 mmol, 10 eq) was added to a solution of 38 (25 mg, 0.03 mmol, 1 eq) in dry THF, under inert atmosphere. The colorless solution was refluxed overnight before being cooled to 0° C. Water (0.047 mL), aqueous solution of hydrogen peroxide (30% w/w, 0.100 mL) and 2N aqueous solution of sodium hydroxide (0.117 mL) were successively added. The resultant white suspension was stirred for an additional 3 h. The mixture was then diluted with ethyl acetate and poured onto water. The organic phase was then dried over magnesium sulphate, filtered and concentrated to afford a yellowish oil. Purification over silica gel chromatography (cyclohexane/ethyl acetate 100:0 to 80:20) yielded alcohol 39 (2 mg, 8% yield).

Synthesis of Compound 40

$C_{56}H_{58}N_2O_7$ M=871.07 g·mol$^{-1}$

Mass (ESI$^+$): 871.6 (M+H); 893.6 (M+Na); 909.5 (M+K)

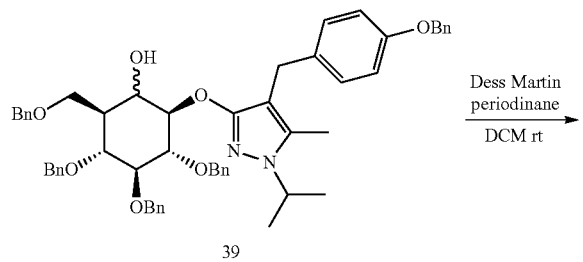

39

Dess Martin periodinane
DCM rt

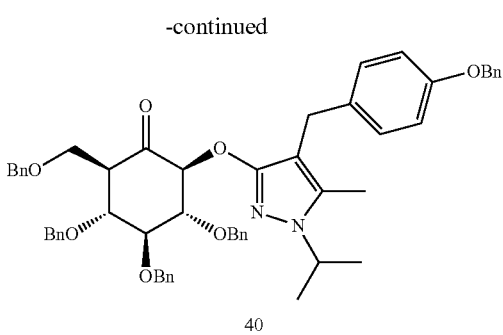

40

Dess-Martin periodinane (9 mg, 0.021 mmol, 1.5 eq) was added to a solution of 39 (12 mg, 0.014 mmol, 1 eq) in dry dichloromethane under inert atmosphere. The reaction mixture was stirred at room temperature for 2 h before being diluted with dichloromethane and 1N aqueous sodium hydroxide. The aqueous layer was then extracted with dichloromethane and the resultant organic layer was dried over sodium sulphate, filtered and concentrated. The crude yellow oil was then purified on silica gel chromatography (cyclohexane/ethyl acetate 100:0 to 72:28) to afford ketone 40 (8 mg, 67% yield) as a yellowish oil.

Synthesis of Compound 41

$C_{56}H_{58}F_2N_2O_6$ M=893.07 g·mol$^{-1}$

Mass (ESI$^+$): 893.4 (M+H); 911.5 (M+H$_2$O)$^+$

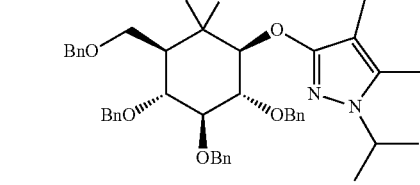

40

DAST
DCM, RT to 35° C.

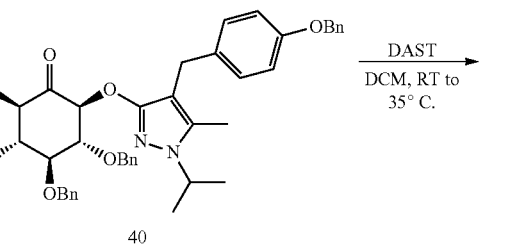

41

DAST (0.05 mL, 0.410 mmol, 45 eq) was added to a solution of 40 (8 mg, 0.009 mmol, 1 eq) in dry dichloromethane (0.05 mL) under inert atmosphere. The reaction mixture was stirred at room temperature overnight and 3 h at 35° C. The reaction mixture was allowed to reach room temperature before being diluted with dichloromethane and poured into water. The organic layer was then washed with a saturated aqueous solution of NaHCO$_3$, dried over magnesium sulphate, filtered and concentrated to afford crude compound 41 as an orange residue.

Synthesis of Compound 42

$C_{10}H_7FS$ M=178.23 g·mol$^{-1}$ $^{19}F$ NMR (CDCl$_3$, 282.5 MHz): −109.8 (m, 1F, Ar—F).

Mass (GC-MS): 133 (41%); 178 (100%)

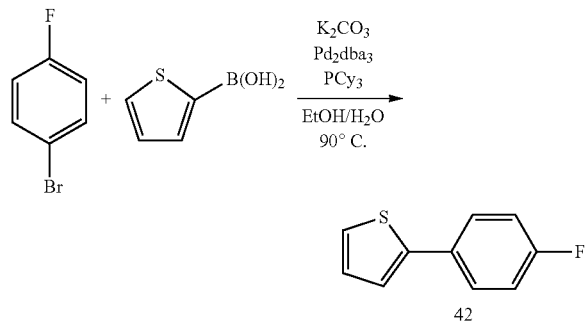

Into a freshly degassed mixture of EtOH (69 mL) and H$_2$O (9 mL) was added Pd$_2$dba$_3$ (534 mg, 0.58 mmol, 0.025 eq), PCy$_3$ (660 mg, 2.35 mmol, 0.1 eq), 2-thiophene boronic acid (3.00 g, 23.4 mmol, 1 eq), K$_2$CO$_3$ (6.48 g, 46.9 mmol, 2 eq), and 4-bromofluorobenzene (5.17 mL, 47.0 mmol, 2 eq). The resultant mixture was stirred overnight at 90° C. and then allowed to reach room temperature. MgSO$_4$ was added to quench water and the mixture was filtered on a pad of Celite using ethyl acetate. The filtrate was concentrated and purified on silica gel chromatography (cyclohexane/ethyl acetate 100:0 to 95:5) to afford compound 42 (3.84 g, 92% yield) as a white solid.

Synthesis of Compound 43

$C_{18}H_{12}BrFOS$ M=375.25 g·mol$^{-1}$ $^{19}F$ NMR (CDCl$_3$, 282.5 MHz): −1113 (m, 1F, Ar—F).

Mass (GC-MS): 375.0 (97%); 376.0 (28%); 377.0 (100%); 416.0 (23%); 418.0 (23%)

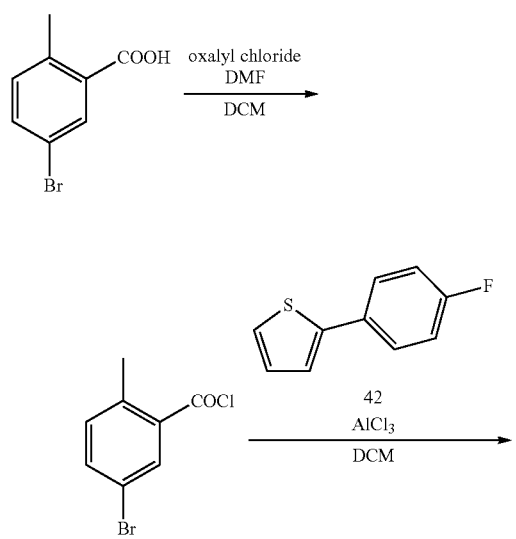

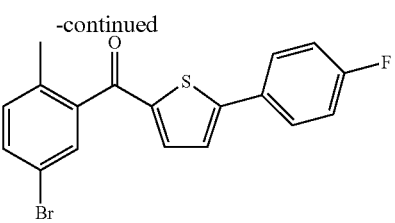

5-Bromo-2-methylbenzoic acid (725 mg, 3.37 mmol, 1 eq) was suspended in dry dichloromethane (9.7 mL). Oxalyl chloride (0.32 mL, 3.74 mmol, 1.1 eq) and N,N-dimethylformamide (0.013 mL, 0.17 mmol, 0.05 eq) were then added at room temperature and the mixture was stirred for 6 hours. The solvent was then evaporated to give 5-bromo-2-methylbenzoyl chloride as yellow oil. This crude product was dissolved in dry dichloromethane (19.3 mL), AlCl$_3$ (49.5 mg, 3.71 mmol, 1.1 eq) and 42 (600 mg, 3.37 mmol, 1 eq) were then added at 0° C. (internal temperature). The resultant mixture was stirred at this temperature for 30 minutes and then at room temperature overnight. The reaction mixture was poured into ice and water, the organic layer was separated and the aqueous layer was extracted with dichloromethane. The organic layers were gathered, dried over MgSO$_4$, filtered and concentrated. The residue was taken up with n-hexane to form a precipitate which was collected by filtration, washed with n-hexane and dried to afford compound 43 (69% yield) as yellowish crystals.

Synthesis of Compound 44

$C_{18}H_{14}BrFS$ M=361.27 g·mol$^{-1}$ $^{19}F$ NMR (CDCl$_3$, 282.5 MHz): −115.0 (m, 1F, Ar—F).

Mass (ESI$^+$): 133 (29%); 177 (49%); 182 (55%); 184 (70%); 191 (72%); 281 (39%); 360 (95%); 362 (100%)

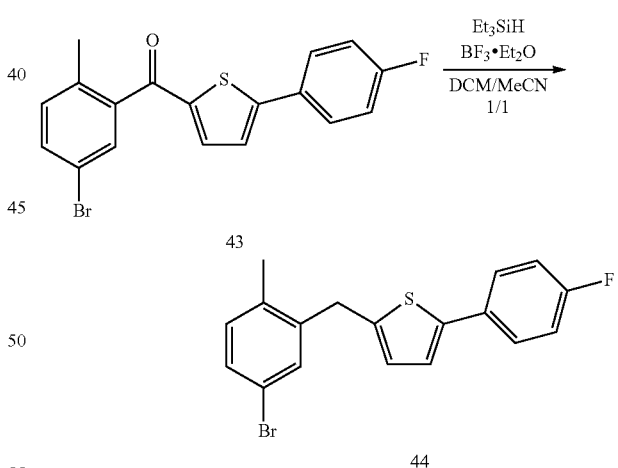

Et$_3$SiH (0.99 mL, 6.18 mmol, 2.9 eq) was added at room temperature to a solution of ketone 43 (800 mg, 2.13 mmol, 1 eq) in anhydrous dichloromethane-acetonitrile (1:1, v/v, 16 mL). The resultant mixture was cooled to 0° C. and BF$_3$.Et$_2$O (0.75 mL, 5.97 mmol, 2.8 eq) was slowly added. The reaction mixture was then stirred at room temperature for 3 hours. A saturated aqueous solution of NaHCO$_3$ was slowly added at 0° C. The aqueous layer was extracted with dichloromethane and the resultant organic layer was dried over MgSO$_4$, filtered and concentrated. The crude mixture was then recrystallized with MeOH to afford compound 44 (70% yield) as yellowish crystals.

Synthesis of Compound 45

$C_{53}H_{49}FO_5S$ M=817.02 g·mol$^{-1}$
$^{19}F$ NMR(CDCl$_3$, 282.5 MHz): −115.2 (m, 1F, Ar—F)
Mass (ESI$^+$): 839.5 [M+Na]$^+$; 855.4 [M+K]$^+$

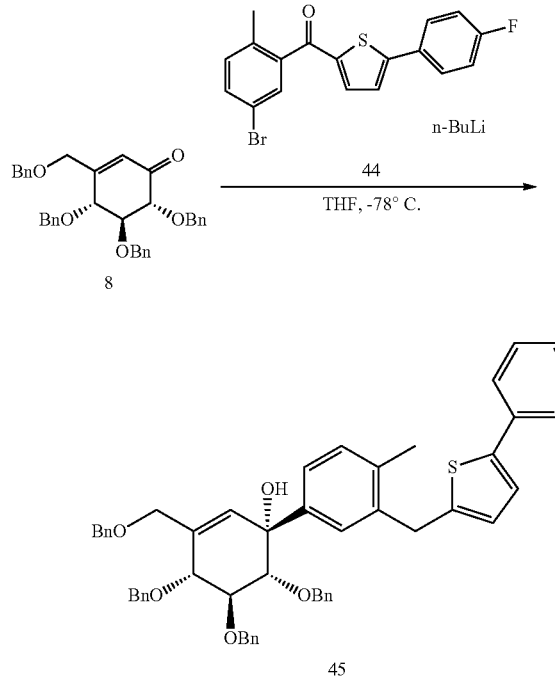

n-Butyllithium (1.4M in hexanes, 0.30 mL, 0.412 mmol, 1.1 eq) was slowly added to a cooled solution (−70° C.) of 44 (149 mg, 0.412 mmol, 1.1 eq) in anhydrous THF-toluene (1:1, v/v, 4.8 mL) under inert atmosphere. The resultant dark blue solution was stirred for 5 min at the same temperature before a cooled solution (−70° C.) of cyclohexenone 8 was slowly added. The reaction mixture was stirred for 15 min at −70° C. before being poured into water. The organic layer was then dried over sodium sulphate, filtered and concentrated to afford crude 45 (300 mg, 98% yield) as yellow oil which was used in the next step without further purification.

Synthesis of Compound 46

$C_{53}H_{49}FO_4S$ M=801.02 g·mol$^{-1}$
$^{19}F$ NMR (CDCl$_3$, 282.5 MHz): −115.3 (m, 1F, Ar—F)
Mass (ESI$^+$): 823.5 [M+Na]$^+$; 839.4 [M+K]$^+$

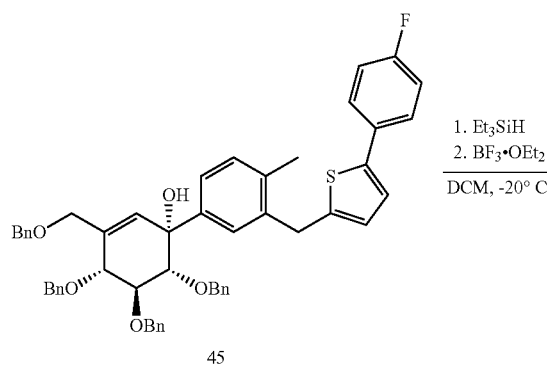

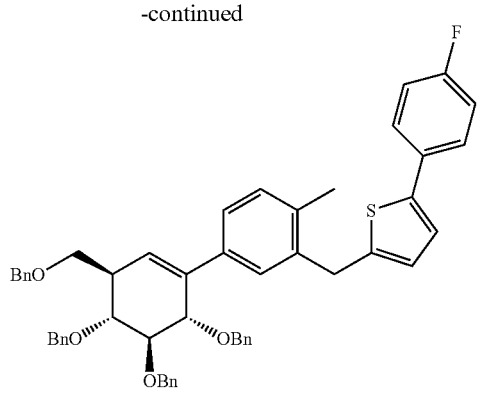

Et$_3$SiH (0.025 mL, 0.157 mmol, 3 eq) and BF$_3$·Et$_2$O (0.013 mL, 0.105 mmol, 2 eq) were successively added to a cooled solution (−20° C.) of 45 (43 mg, 0.052 mmol, 1 eq) in anhydrous dichloromethane (0.55 mL) under inert atmosphere. The resultant solution was stirred at −20° C. for 1 h 45, diluted with dichloromethane and poured into brine. The organic layer was dried over sodium sulphate, filtered and concentrated to yield a green oil which was then purified on silica gel chromatography (cyclohexane/ethyl acetate 100:0 to 82:18) to afford compound 46 (27 mg, 64% yield) as a green oil.

Synthesis of Compound 47

$C_{53}H_{51}FO_5S$ M=819.03 g·mol$^{-1}$
$^{19}F$ NMR (CDCl$_3$, 282.5 MHz): −115.3 (m, 1F, Ar—F)
Mass (ESI$^+$): 841.4 [M+Na]$^+$; 857.4 [M+K<]$^+$

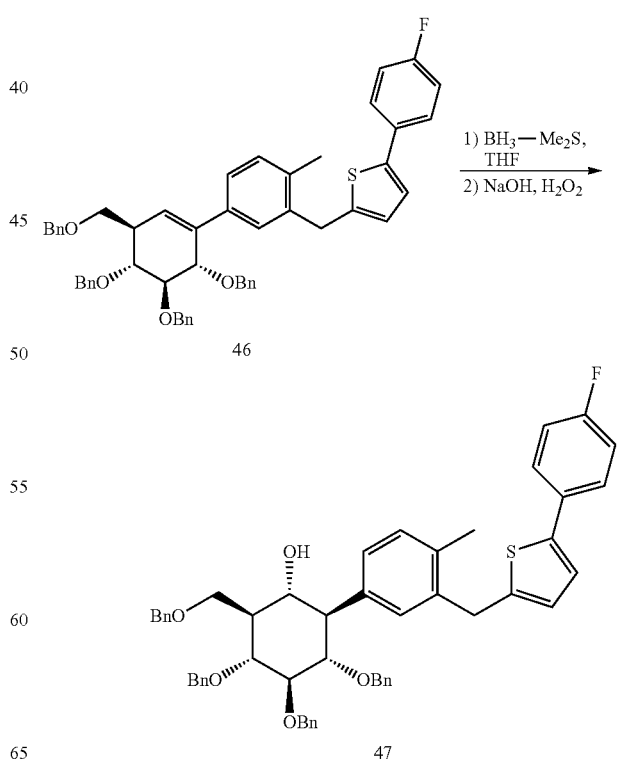

BH$_3$.Me$_2$S (2M in THF, 0.065 mL, 0.130 mmol, 4 eq) was added to a cooled solution (0° C.) of 46 (26 mg, 0.032 mmol, 1 eq) in dry THF (0.335 mL) under inert atmosphere. The resultant solution was stirred at room temperature overnight before being cooled to 0° C. Water (0.041 mL, 2.27 mmol, 70 eq) was then added carefully followed by hydrogen peroxide (30% w/v, 0.11 mL, 0.97 mmol, 30 eq) and 2N aqueous sodium hydroxide (0.13 mL, 0.26 mmol, 8 eq). The white suspension was stirred at room temperature for 4 h. The reaction mixture was then diluted with ethyl acetate and poured onto water. The organic layer was dried over sodium sulphate, filtered and concentrated to yield a colorless residue which was then purified on silica gel chromatography (cyclohexane/ethyl acetate 100:0 to 77:23) to afford alcohol 47 (7 mg, 26% yield) as a yellowish residue.

Synthesis of Compound 48

C$_{53}$H$_{49}$FO$_5$S M=817.02 g·mol$^{-1}$
$^{19}$F NMR (CDCl$_3$, 282.5 MHz): −115.4 (m, 1F, Ar—F)
Mass (ESI$^+$): 839.4[M+Na]$^+$; 855.4[M+K]$^+$

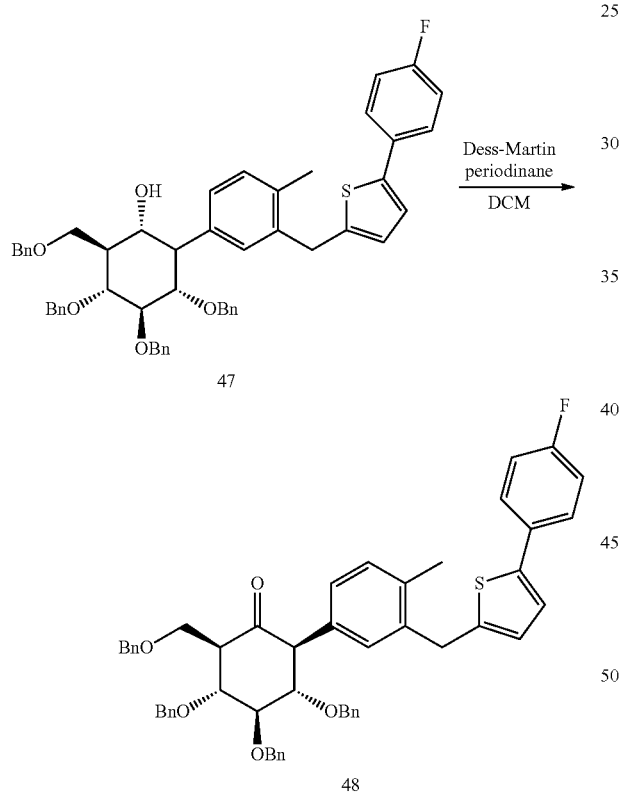

Dess Martin periodinane (5 mg, 0.013 mmol, 1.5 eq) was added to a solution of alcohol 47 (7 mg, 0.009 mmol, 1 eq) in dichloromethane (0.150 mL) The resultant mixture was stirred at room temperature for 1 h 30 before being poured in 1N aqueous sodium hydroxide. The organic layer was separated and the aqueous layer was extracted with dichloromethane. The combined organic layers were dried over sodium sulphate, filtered and concentrated. The crude residue was then purified on silica gel chromatography (cyclohexane/ethyl acetate 100:0 to 80:20) to afford ketone 48 (6 mg, 86% yield) as a yellowish residue.

Synthesis of Compound 49

C$_{53}$H$_{49}$F$_3$O$_4$S M=839.01 g·mol$^{-1}$
$^{19}$F NMR (CDCl$_3$, 282.5 MHz): −115.3 (m, 1F, Ar—F); 113.75 (dt, J1=254 Hz, J2=29 Hz, 1F, CFF); −100.4 (d, J=254 Hz, 1F, CFF).
Mass (ESI$^+$): 861.3 [M+Na]$^+$; 877.4 [M+K]$^+$

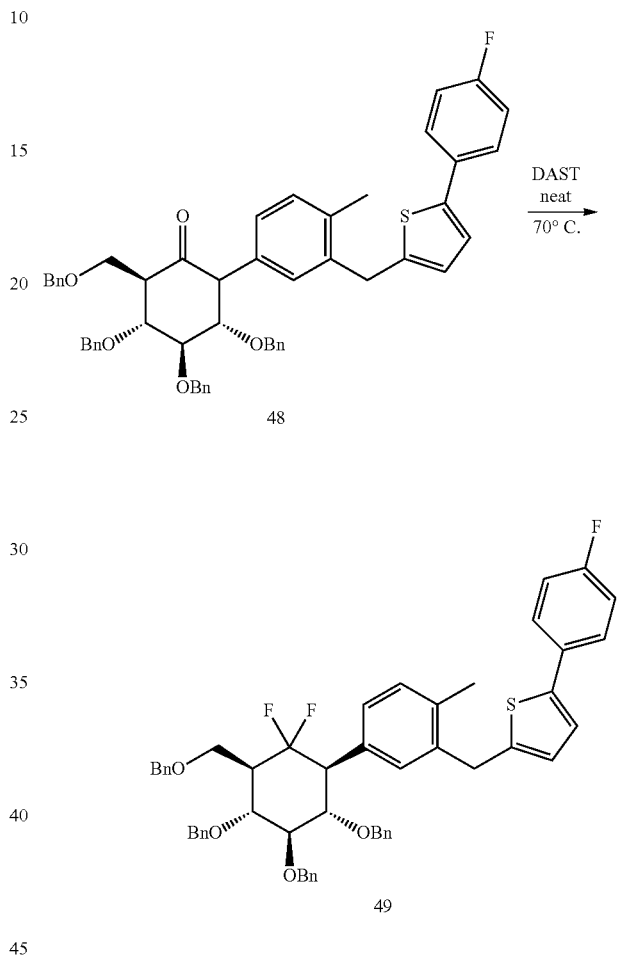

Ketone 48 (316 mg, 0.39 mmol, 1 eq) was dissolved in DAST (1.4 mL, 11.4 mmol, 30 eq) and the reaction mixture was stirred overnight under inert atmosphere at 70° C. Dichloromethane was added at room temperature and the reaction was poured into water. The aqueous phase was extracted with dichloromethane and the organic phase was dried over Na$_2$SO$_4$, filtered and concentrated. The crude product was purified on silica gel chromatography (cyclohexane/ethyl acetate 100:0 to 78:12) followed by preparative HPLC (Kromasil C18, MeOH/H$_2$O 95:5) to afford 49 (84 mg, 26% yield) as a colorless oil.

Synthesis of Compound 50

C$_{25}$H$_{25}$F$_3$O$_4$S M=478.52 g·mol$^{-1}$
$^{19}$F NMR (CDCl$_3$, 282.5 MHz): −100.2 (d, J=254 Hz, 1F, CFF); −116.2 (dt, J1=254 Hz, J2=28 Hz, 1F, CFF); −117.6 (m, 1F, Ar—F).
Mass (ESI$^+$): 501.2 [M+Na]$^+$
Mass (ESI$^-$): 513.2 [M+Cl]$^-$

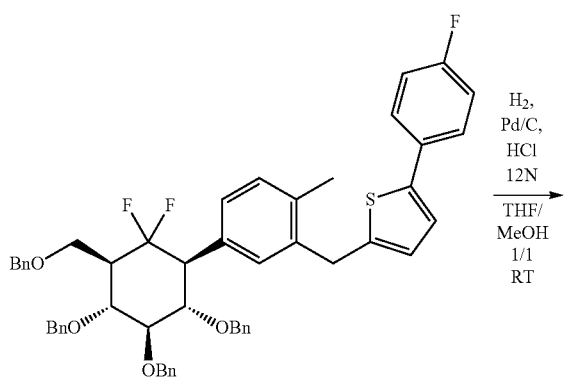

49

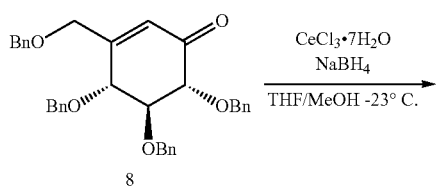

50

Compound 49 (48 mg, 0.057 mmol, 1 eq) was dissolved in THF-MeOH (1:1, v/v, 4.2 mL) under inert atmosphere. 10% Pd/C (96 mg, 0.02 mmol, 0.35 eq) and 5 drops of 12N aqueous hydrochloric acid were added to the mixture which was degassed 5 times with $H_2$. The resultant black suspension was stirred under an atmosphere of $H_2$ at room temperature for 72 h. The reaction mixture was filtered over a pad of Celite 545 and the filtrate was concentrated. The crude product was purified on silica gel chromatography (dichloromethane/Methanol 100:0 to 91:9) followed by preparative HPLC (5-amide C18, MeCN/$H_2O$ 38:62) to afford compound 50 in 27% yield as a white solid.

Synthesis of Compound 51

$C_{35}H_{36}O_5$ M=536.66 g·mol$^{-1}$
Mass: (ESI$^+$): 554.13 [M+H$_2$O]$^+$

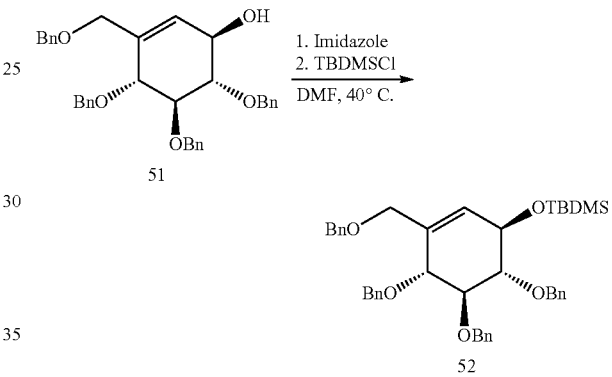

Under inert atmosphere, cerium chloride heptahydrate (167 mg; 0.449 mmol; 1.2 eq) was added to a solution of cyclohexenone 8 (200 mg; 0.374 mmol; 1 eq) in a MeOH-THF (3:1, v/v, 5 mL) cooled to −23° C. The reaction mixture was stirred for 30 minutes at this temperature and sodium borohydride (21 mg; 0.561 mmol; 1.5 eq) was added. After a further 45 minutes, a saturated aqueous solution of ammonium chloride (15 mL) and sodium chloride (15 mL) were added. The aqueous layer was extracted with ethyl acetate and the combined extracts were dried over sodium sulphate, filtered and concentrated. The residue was purified by silica gel chromatography (EtOAc/cyclohexane 3/97 to 35/65) to afford alcohol 51 (137 mg, 68% yield), as a white solid.

Synthesis of Compound 52

$C_{41}H_{50}O_5Si$ M=650.92 g·mol$^{-1}$
Mass (ESI$^+$): 673.5 [M+Na]$^+$; 689.3 [M+K]$^+$ To a solution of 51 (3.80 g; 7.09 mmol; 1 eq) in dry dimethylformamide (25 mL), under inert atmosphere, was added imidazole (1.45 g; 21.3 mmol; 3 eq). The reaction mixture was stirred for 30 minutes at room temperature before tert-butyldimethylsilyl chloride (1.70 g; 11.3 mmol; 1.6 eq) was added. The mixture was heated at 40° C. for 12 h then quenched with water and extracted with ethyl acetate. The organic layers were combined, washed with brine, dried over sodium sulphate, filtered and concentrated to afford compound 52 (4.57 g, 99% yield), as yellow oil. This compound was engaged in the next step without further purification.

Synthesis of Compound 53

$C_{41}H_{52}O_6Si$ M=668.93 g·mol$^{-1}$
Mass (ESI$^+$): 691.4 [M+Na]$^+$; 707.4 [M+K]$^+$

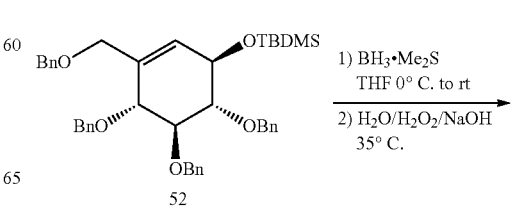

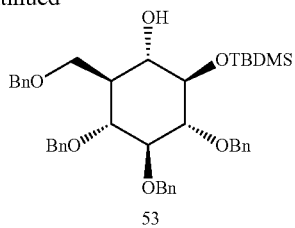

53

To a solution of 52 (4 g; 6.15 mmol; 1 eq) in dry THF (60 mL), under inert atmosphere, was added borane-dimethylsulfide complex (12.3 mL; 2M in THF; 24.6 mmol; 4 eq) at 0° C. The reaction medium was stirred overnight at room temperature before water (7.8 mL; 0.43 mol; 70 eq), hydrogen peroxide 30% in water (21.0 mL, 0.19 mol; 30 eq) and 3M aqueous sodium hydroxide (16.4 mL; 49.2 mmol; 8 eq) were successively added at 0° C. The mixture was stirred for 2 h at room temperature before being quenched with a saturated aqueous solution of ammonium chloride (300 mL) The aqueous layer was extracted with ethyl acetate and the combined organic layers were washed with brine, dried over sodium sulphate, filtered and concentrated. The residue was purified on silica gel chromatography (cyclohexane/ethyl acetate) to afford alcohol 53 (754 mg, 63% yield), as a yellow oil. (Crude 53 can also be engaged in the next step without further purification).

Synthesis of Compound 54

$C_{41}H_{50}O_6Si$ M=666.92 g·mol$^-$
Mass (ESI$^+$): 689.5 [M+Na]$^+$; 705.4 [M+K]$^+$

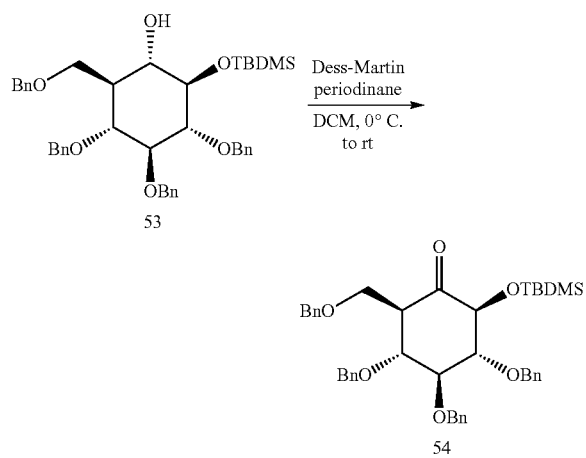

To a solution of 53 (1.51 g; 2.26 mmol; 1 eq) in dry dichloromethane (23 mL), under inert atmosphere, was added Dess-Martin periodinane (1.44 g; 3.39 mmol; 1.5 eq) at 0° C. The mixture was stirred overnight at room temperature before a 1M aqueous solution of sodium hydroxide (50 mL) was added. The aqueous layer was extracted with dichloromethane (2×100 mL) and the combined organic layers were dried over sodium sulphate, filtered and concentrated. The residue was purified on silica gel chromatography (EtOAc/cyclohexane 1/99 to 11/89) to afford ketone 54 (1.13 g, 75% yield), as yellow oil. Alternatively, ketone 54 can be obtained with 55% yield over 3 steps from 51, performing only one purification at this last step.

Synthesis of Compound 55

$C_{35}H_{36}O_6$ M=552.66 g·mol$^{-1}$
Mass (ESI$^+$): 575.3 [M+Na]$^+$; 591.3 [M+K]$^+$

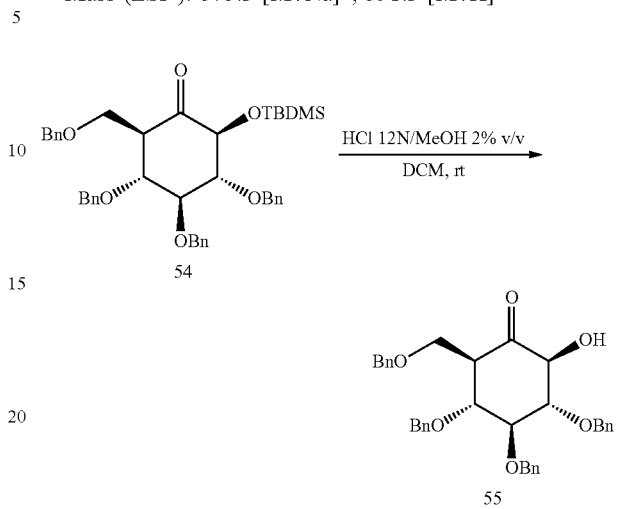

To a solution of 54 (560 mg; 0.84 mmol) in dichloromethane (4 mL) was added a solution of 12N HCl in methanol (2% v/v, 4 mL). The reaction mixture was stirred overnight at room temperature. Water was then added, followed by a saturated aqueous solution of sodium hydrogen carbonate until neutralization. The mixture was extracted with dichloromethane, dried over sodium sulfate, filtered and concentrated. The residue was triturated in ethanol and filtered to afford compound 55 (337 mg, 73% yield) as white solid.

Synthesis of Compound 56

Mass (ESI$^+$): 617.6 [M+Na]$^+$; 633.6 [M+K]$^+$

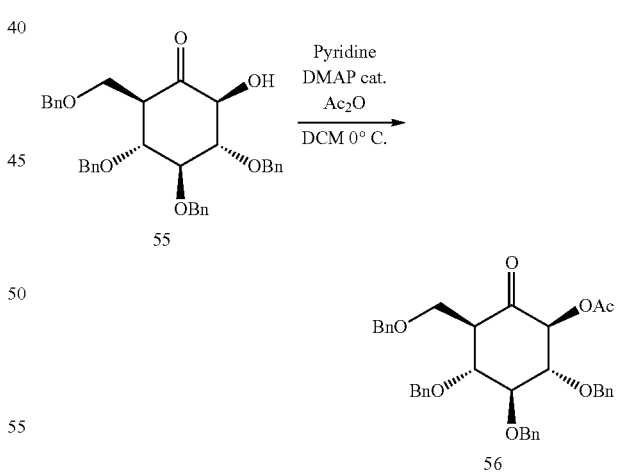

To a solution of 55 (1.27 g; 2.30 mmol; 1 eq) in dry dichloromethane (3 mL), under inert atmosphere, were successively added at 0° C., pyridine (0.93 mL; 11.5 mmol; 5 eq), 4-dimethylaminopyridine (60 mg; 0.46 mmol; 0.2 eq) and acetic anhydride (0.44 mL; 4.60 mmol; 2 eq). The mixture was stirred at the same temperature for 45 minutes. Water followed by 1N aqueous solution of hydrochloric acid were then added. The aqueous layer was extracted with dichloromethane and the combined organic layers were washed with brine, dried over sodium sulphate, filtered and concentrated to afford quantitatively ketone 56 (1.39 g) as a light yellow oil. Crude 56 was engaged in the next step without further purification.

Synthesis of Compound 57

$C_{37}H_{38}F_2O_6$ M=616.69 g·mol$^{-1}$ $^{19}$F NMR (CDCl$_3$, 282.5 MHz): −110.0 (d, J=250 Hz, 1F, CFF); −119.4 (ddd, J1=249 Hz, J2=21 Hz, J3=29 Hz, 1F, CFF).

Mass (ESI$^+$): 603.4 [M−HF+Li]$^+$; 619.3 [M−HF+Li]$^+$; 623.3 [M+Li]$^+$; 639.3 [M+Na]$^+$; 655.3 [M+K]$^+$

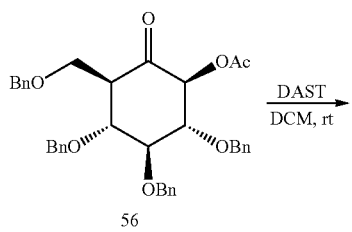

To a solution of 56 (1.30 g; 2.19 mmol; 1 eq) in dry dichloromethane (5.2 mL), under inert atmosphere, was added diethylaminosulfur trifluoride (5.2 mL; 42.4 mmol; 19 eq). The reaction medium was stirred for 16 h at room temperature. The solution was then diluted with dichloromethane and solid sodium hydrogen carbonate was added. The mixture was stirred for additional 30 minutes at 0° C. before water was added dropwise. The aqueous layer was extracted with dichloromethane and the combined organic layers were dried over sodium sulphate, filtered and concentrated. The residue was purified on silica gel chromatography (EtOAc/cyclohexane 2/98 to 12/88) to afford compound 57 (471 mg, 35% yield) in the form of a light yellow oil.

Synthesis of Compound 58

$C_{37}H_{40}O_6$ M=580.71 g·mol$^{-1}$

Mass (ESI$^+$): 603.3 (M+Na)$^+$; 619.3 (M+K)$^+$

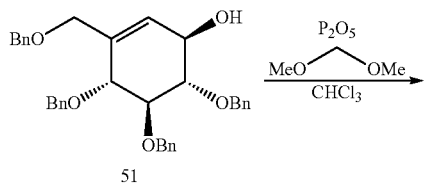

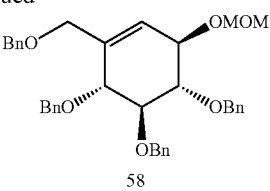

Under inert atmosphere, crude 51 (53.7 g) was dissolved in a mixture of dry chloroform (500 mL) and dimethoxymethane (292 mL, 3.3 mol, 33 eq). P$_2$O$_5$ (73.9 g, 521 mmol, 5.2 eq.) was added. The reaction was kept under mechanical stirring for 1 h at room temperature. The mixture was then filtered on a pad of Celite® 545 (elution with dichloromethane) and washed with a saturated aqueous solution of NaHCO$_3$ (700 mL) Water (1 L) was then added and the mixture was extracted with dichloromethane (2×300 mL), washed with brine, dried over Na$_2$SO$_4$, filtered and concentrated to afford 58 (57.7 g) in the form of a brown oil which slowly crystallized. 58 was engaged in the next step without further purification.

Synthesis of Compound 59

$C_{37}H_{42}O_7$ 598.73 g·mol$^{-1}$

Mass (ESI$^+$): 621.3 (M+Na)$^+$; 637.3 (M+K)$^+$

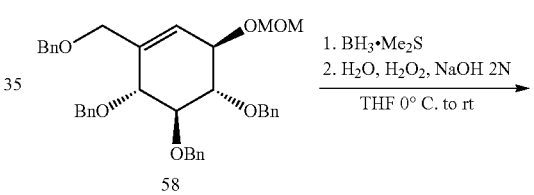

Under inert atmosphere, borane-dimethyl sulfide complex (2M in THF, 199 mL, 397 mmol, 4 eq) was added to a solution of 58 (57.7 g) in dry THF (497 mL) cooled to 0° C. The reaction mixture was then stirred overnight at room temperature before being cooled to 0° C. and carefully treated with water (125 mL, 6.96 mol, 70 eq.), followed by hydrogen peroxide (30% w/v in H$_2$O, 338 mL, 2.98 mol, 30 eq) and sodium hydroxide (2M in H$_2$O, 397 mL, 0.79 mol, 8 eq). The mixture was allowed to react for 2 h at room temperature (~25° C.) before a saturated aqueous solution of ammonium chloride (700 mL) and water (300 mL) were added to quench the reaction. The mixture was extracted with ethyl acetate (3×500 mL) and the combined organic layers were washed with water (600 mL) and brine (600 mL), dried over Na$_2$SO$_4$, filtered, and concentrated to afford crude 59 (59.5 g) in the form of a yellow oil. 59 was engaged in the next step without further purification.

Synthesis of Compound 60

$C_{37}H_{40}O_7$ M=596.71 g·mol$^{-1}$
Mass (ESI$^+$): 619.3 (M+Na)$^+$; 635.3 (M+K)$^+$

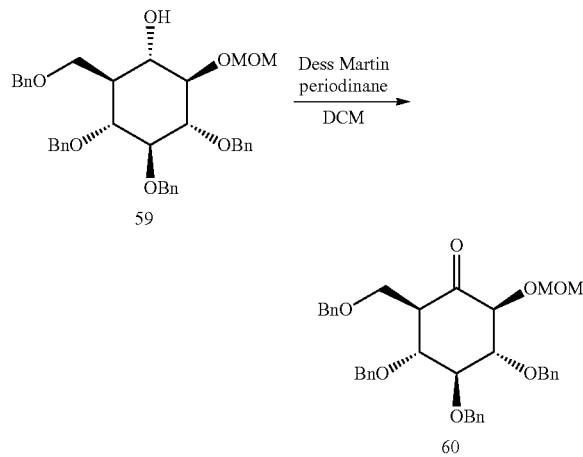

Dess-Martin periodinane (84.3 g; 199 mmol; 2 eq) was added portionwise to a solution of crude 59 (59.5 g) in dry dichloromethane (1 L) at 0° C. The reaction was then stirred 18 h at room temperature before sodium hydroxide (1N in H$_2$O, 1 L) and water (500 mL) were added. The aqueous layer was then extracted with dichloromethane (2×400 mL) and the combined organic layers were dried over sodium sulphate, filtered and concentrated. The residue was purified on silica gel chromatography (cyclohexane/ethyl acetate 98:2 to 86:14, v/v on Biotage SNAP 750 g cartridge), to afford the target ketone 60 (32 g, 48% yield over 4 steps) as a yellow solid.

Synthesis of Compound 61

$C_{37}H_{40}F_2O_6$ M=618.71 g·mol$^{-1}$
$^{19}$F NMR (CDCl$_3$, 282.5 MHz): −108.5 (d, J=252 Hz, 1F, CFF); −121.0 (ddd, J1=252 Hz, J2=30 Hz, J3=20 Hz, 1F, CFF).
Mass (ESI$^+$): 641.3 (M+Na)$^+$; 657.3 (M+K)$^+$

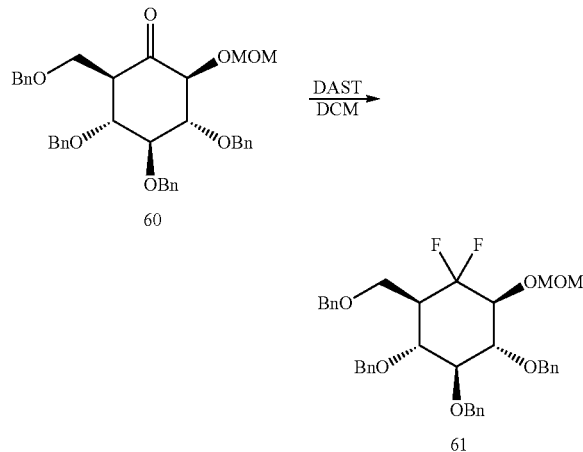

DAST (125 mL, 1.02 mol, 19 eq.) was slowly added to a cooled solution (0° C.) of 60 (32 g, 53.6 mmol, 1 eq.) in dry dichloromethane (145 mL) The reaction mixture was then allowed to reach room temperature and was stirred overnight. Dichloromethane (400 mL) was then added and the mixture was slowly poured into a mixture of ice (1 L), dichloromethane (300 mL) and NaHCO$_3$ (400 g). The mixture was vigorously stirred for 15 min. Water (500 mL) was added and the aqueous layer was extracted with dichloromethane (2×300 mL). The combined organic extracts were dried over Na$_2$SO$_4$, filtered and concentrated to afford crude 61 (32.6 g) in the form of a yellowish oil. 61 was engaged in the next step without further purification.

Synthesis of Compound 62

$C_{35}H_{36}F_2O_5$ M=574.65 g·mol$^{-1}$
$^{19}$F NMR (CDCl$_3$, 282.5 MHz): −110.7 (d, J=249 Hz, 1F, CFF); −123.7 (ddd, J1=248 Hz, J2=29 Hz, J3=19 Hz, 1F, CFF).
Mass (ESI$^+$): 577.5 [M−HF+Na]$^+$; 592.5 [M+H$_2$O]$^+$; 597.5 [M+Na]$^+$; 613.5 [M+K]$^+$

A.

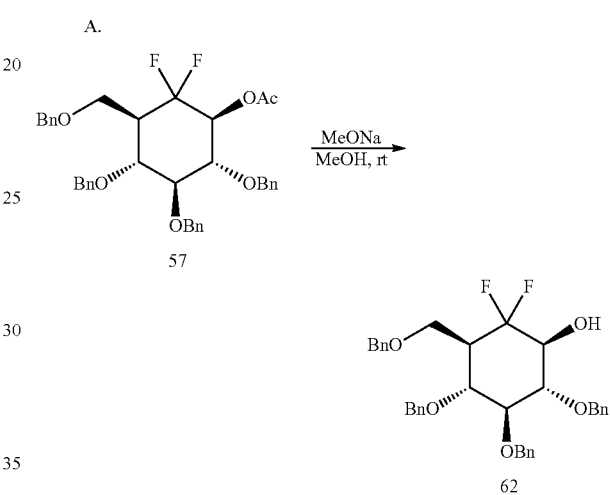

B.

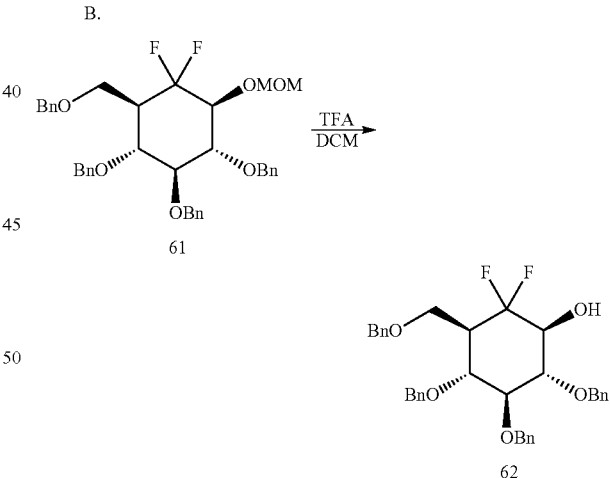

A.
To a solution of 57 (70 mg; 0.114 mmol; 1 eq) in dry methanol, under inert atmosphere, was added sodium methanolate (8 mg; 0.142 mmol; 1.25 eq). The reaction medium was stirred overnight at room temperature. Water was then added followed by a 1N aqueous solution of hydrochloric acid which was added until pH=6. The mixture was extracted with ethyl acetate, washed with brine, dried over sodium sulphate, filtered and concentrated to afford alcohol 62 (65 mg) in the form of a light orange solid, with a quantitative yield.

B.

Trifluoroacetic acid (98.0 mL, 1.32 mol, 25 eq.) was added to a solution of 61 (32.6 g) in dry dichloromethane (260 mL) under inert atmosphere. The reaction mixture was stirred overnight at room temperature. The mixture was cooled to 0° C. and water (500 mL) was added. The layers were separated and the organic layer was washed with water (500 mL) The combined aqueous layers were combined and extracted with dichloromethane (2×100 mL). The combined organic layers were washed with sat. NaHCO$_3$ (250 mL), dried over sodium sulfate, filtered and concentrated. The crude mixture was purified on silica gel chromatography (cyclohexane/ethyl acetate 98:2 to 82:18, v/v on Biotage SNAP 750 g cartridge) to afford 62 (13.6 g, 30% over 2 steps) as a white solid.

Synthesis of Compound 63

$C_{35}H_{36}F_2O_6/C_{35}H_{34}F_2O_5$ M=590.65 g·mol$^{-1}$/572.64 g·mol$^{-1}$ $^{19}$F NMR (CDCl$_3$, 282.5 MHz):

Hydrate form: −117.3 (dd, J1=257 Hz, J2=30 Hz, 1F, CFF); −125.6 (d, J1=258 Hz, 1F, CFF).

Ketone form: −112.1 (ddd, J1=260 Hz, J2=32 Hz, J3=6 Hz, 1F, CFF); −119.4 (dd, J1=260 Hz, J2=4 Hz, 1F, CFF).

Mass (ESI$^+$): 608.4 [M+H$_2$O]$^+$; 613.5 [M+Na]$^+$; 619.5 [M+K]$^+$

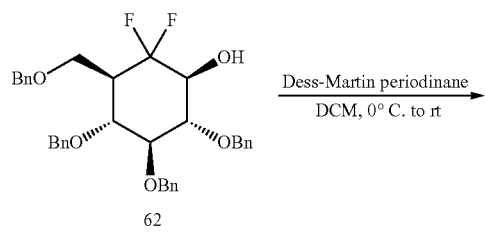

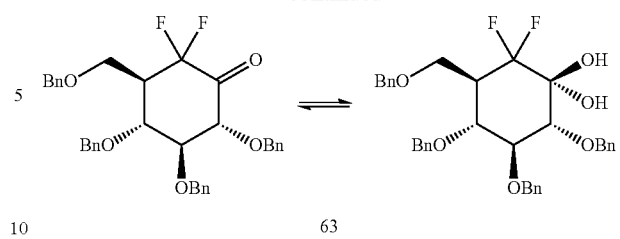

To a solution of 62 (200 mg; 0.35 mmol; eq) in dry dichloromethane, under inert atmosphere, was added Dess-Martin periodinane (295 mg; 0.70 mmol; 2 eq). The reaction medium was stirred for 3 h at room temperature before a 1N aqueous solution of sodium hydroxide (10 mL) was added. The aqueous layer was extracted with dichloromethane and dried over sodium sulphate, filtered and concentrated to afford ketone 63 (158 mg, 77% yield) as a light orange solid which rapidly evolves toward the formation of the hydrate form until equilibrium is reached.

Synthesis of Compound 64

$C_{50}H_{49}ClF_2O_6$ M=819.37 g·mol$^{-1}$ $^{19}$F NMR (CDCl$_3$, 282.5 MHz): −112.3 (dd, J1=266 Hz, J2=27 Hz, 1F, CFF); −113.7 (dd, J1=266 Hz, J2=6 Hz, 1F, CFF).

Mass (ESI$^+$): 836.7[M+H$_2$O]$^+$; 841.8[M+Na]$^+$; 857.7[M+K]$^+$

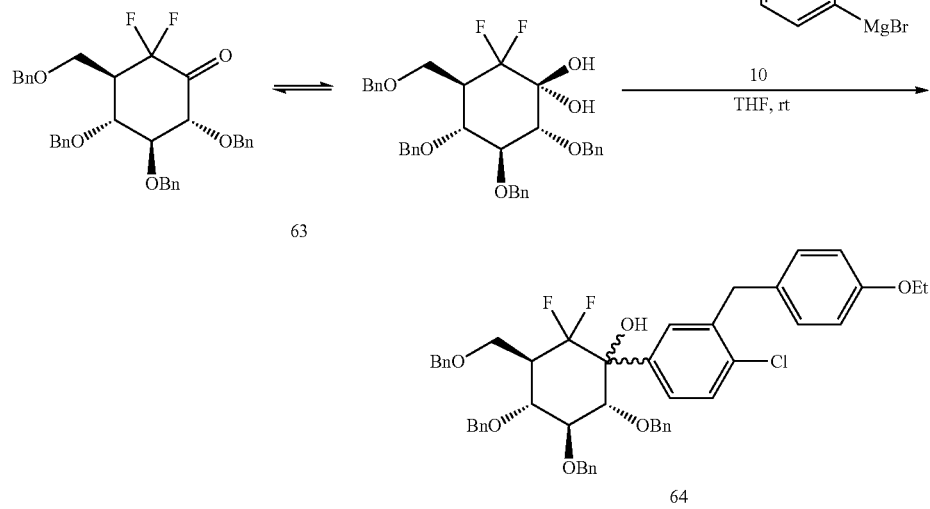

In a Schlenk tube under inert atmosphere containing magnesium turnings (50 mg, 2.04 mmol, 1.2 eq) was added 2 mL (out of 5 mL) of a solution of 10 (552 mg, 1.70 mmol, 1 eq) and 1,2-dibromoethane (15 µL, 0.17 mmol, 0.1 eq) in dry THF (5 mL). The mixture was heated at 75° C. for 5 min to initiate the reaction and the last 3 mL of the solution of 10 and 1,2-dibromoethane were then added dropwise at room temperature. This solution was then stirred at 75° C. for 1 h.

2.4 mL of this Grignard solution, previously cooled to room temperature, were then added to a solution of 63 (158 mg, 0.27 mmol) in dry THF (2 mL). The reaction mixture was stirred at room temperature for 2 h before a saturated aqueous solution of ammonium chloride was added. The aqueous layer was extracted with diethyl ether and the combined organic layers were washed with brine, dried over sodium sulphate, filtered and concentrated. The residue was purified on silica gel chromatography (cyclohexane/ethyl acetate 100:0 to 77:23) to afford compound 64 (152 mg) as a mixture of two diastereomers with 69% yield. These diastereomers can be separated by semi-preparative HPLC.

Synthesis of Compound 65

$C_{22}H_{25}ClF_2O_6$ M=458.88 g·mol$^{-1}$
$^{19}$F NMR (MeOD. 282.5 MHz): −114.0 (dd, J1=262 Hz, J2=7 Hz, 1F, CFF); −115.4 (dd, J1=262 Hz, J2=26 Hz, 1F, CFF).
Mass (ESI$^+$): 481.3 [M+Na]$^+$; 497.3 [M+K]$^+$

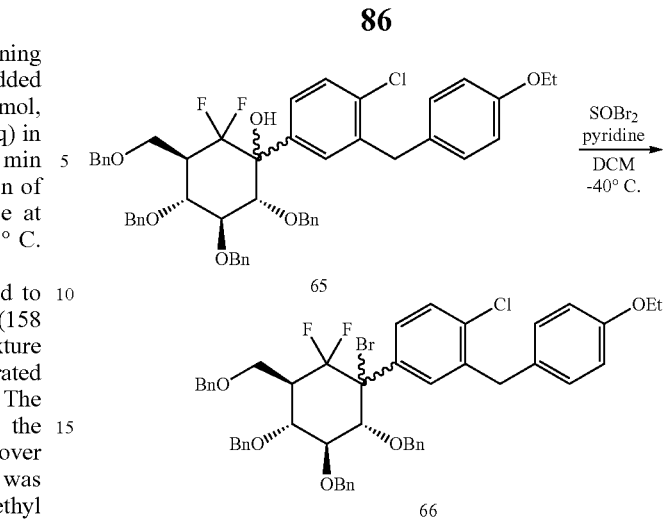

SOBr$_2$ (85 µL, 1.10 mmol, 15 eq) was added at −40° C. to a solution of 65 (60 mg, 0.07 mmol, 1 eq) in dry dichloromethane (0.73 mL) under inert atmosphere. The mixture was stirred while the temperature was gradually raised to 0° C. over 5 h. Pyridine (89 µL, 1.10 mmol, 15 eq) was then added and the solution was stirred for an additional 1 h at 0° C. A solution of aqueous 1M HCl was added and the solution was allowed to reach room temperature. The organic layer was collected and the aqueous layer was

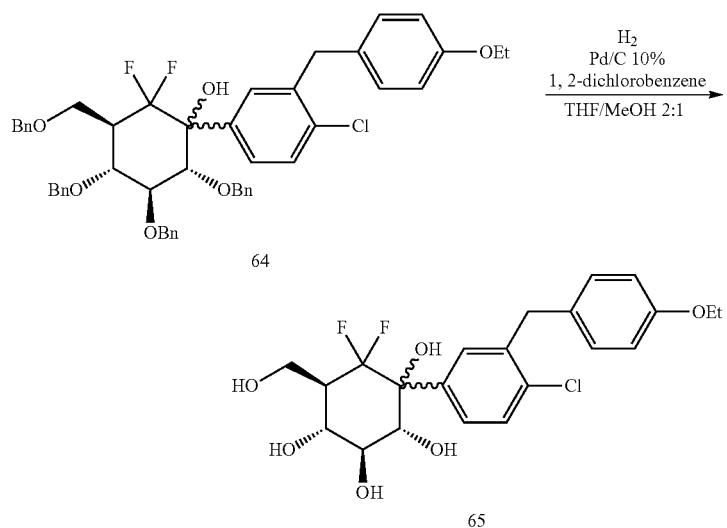

o-Dichlorobenzene (53 µL, 0.47 mmol, 10 eq) followed by Pd/C 10% (56.0 mg, 53.3 µmol, 1.1 eq) were added to a solution of 64 (38.0 mg, 46.4 µmol, 1 eq) in a mixture of THF and MeOH (2:1, v/v, 26 mL) The reaction was placed under hydrogen atmosphere and stirred at room temperature for 2 h. The reaction mixture was filtered and concentrated before being purified on silica gel chromatography to afford the target compound 65.

Synthesis of Compound 66

$C_{50}H_{48}BrClF_2O_5$ M=882.27 g·mol$^{-1}$
$^{19}$F NMR (CDCl$_3$, 282.5 MHz): Major anomer: −97.8 (dd, J1=246 Hz, J2=30 Hz, CFF); −102.6 (d, J=246 Hz, CF).
Mass (ESI$^+$): 4881.2 (M+H)$^+$; 898.3 (M+H$_2$O)$^+$.

extracted with dichloromethane. The combined organic layer was then dried over sodium sulfate, filtered and concentrated. The crude mixture was purified on silica gel chromatography (Biotage SNAP10 g, cyclohexane/ethyl acetate 100:0 to 92/8) to afford 66 (15 mg, 23%) as a colorless oil. The collected fraction contains one major isomer.

Synthesis of Compound 15

$C_{50}H_{49}ClF_2O_6$ M=803.37 g·mol$^{-1}$
$^{19}$F NMR (CDCl$_3$, 282.5 MHz): −100.3 (d, J=254 Hz, 1F, CFF); −113.3 (td, J1=254 Hz, J2=29 Hz, 1F, CFF).
Mass: (ESI$^+$): 820.00 (M+H$_2$O)

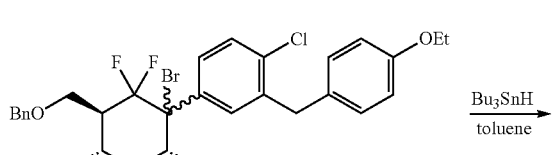

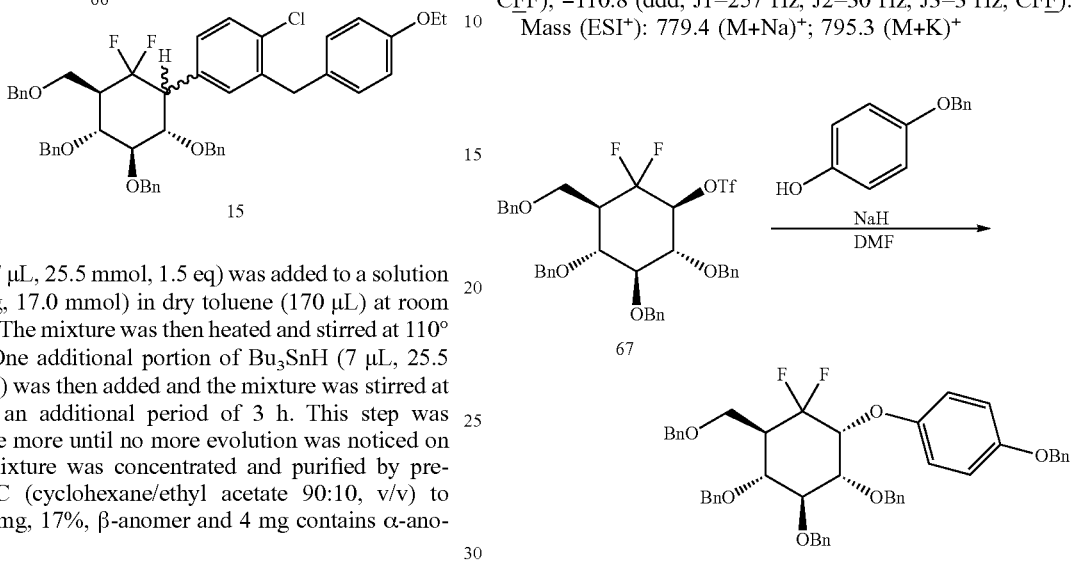

Bu₃SnH (7 µL, 25.5 mmol, 1.5 eq) was added to a solution of 66 (15 mg, 17.0 mmol) in dry toluene (170 µL) at room temperature. The mixture was then heated and stirred at 110° C. for 3 h. One additional portion of Bu₃SnH (7 µL, 25.5 mmol, 1.5 eq) was then added and the mixture was stirred at 110° C. for an additional period of 3 h. This step was repeated once more until no more evolution was noticed on TLC. The mixture was concentrated and purified by preparative TLC (cyclohexane/ethyl acetate 90:10, v/v) to afford 15 (2 mg, 17%, β-anomer and 4 mg contains α-anomer).

Synthesis of Compound 67

$C_{36}H_{35}F_5O_7S$ M=706.72 g·mol⁻¹

¹⁹F NMR (CDCl₃, 282.5 MHz): −74.0 (d, J=12 Hz, C$\underline{F}_3$); −108.2 (dq, J1=252 Hz, J2=12 Hz, CF$\underline{F}$); −119.5 (ddd, J1=253 Hz, J2=31 Hz, J3=18 Hz, CF$\underline{F}$).

Mass (ESI⁺): 724.3 (M+H₂O⁺); 729.2 (M+Na)⁺; 745.2 (M+K)⁺

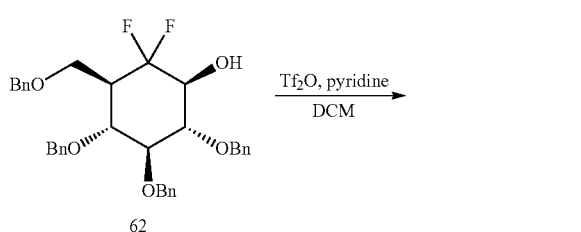

Trifluoromethanesulfonic anhydride (9.5 mL, 57.4 mmol, 3 eq) and pyridine (4.6 mL, 57.4 mmol, 3 eq.) were added to a cooled solution (0° C.) of 62 (11.0 g, 19.1 mmol, 1 eq.) in dry dichloromethane (190 mL) under inert atmosphere. The solution was allowed to warm to room temperature and was stirred overnight. Water (400 mL) was then added to =the cooled mixture (0° C.) which was then extracted with dichloromethane (2×150 mL), dried over sodium sulfate, filtered and concentrated to afford crude 67 (13.6 g) as a brown solid. 67 was engaged in the next step without further purification.

Synthesis of Compound 68

$C_{48}H_{46}F_2O_6$ M=756.87 g·mol⁻¹

¹⁹F NMR (CDCl₃, 282.5 MHz): −107.9 (brd, J1=256 Hz, CF$\underline{F}$); −110.8 (ddd, J1=257 Hz, J2=30 Hz, J3=3 Hz, CF$\underline{F}$).

Mass (ESI⁺): 779.4 (M+Na)⁺; 795.3 (M+K)⁺

Sodium hydride (95%, 1.38 g, 57.3 mmol, 3 eq.) was added to a cooled (0° C.) solution of 4-(benzyloxy)phenol (13.4 g, 66.9 mmol, 3.5 eq.) in dry DMF (95 mL). The reaction mixture was stirred 1 h at the same temperature before a solution of 67 (11.0 g) in dry DMF (95 mL) was added. The reaction mixture was stirred at 50° C. overnight before being cooled again at 0° C. Water (250 mL) followed by a 1N aqueous solution of sodium hydroxide (600 mL) were then added. The mixture was extracted with diethyl ether (300 mL then 2×150 mL) and the combined organic layers were washed with water (2×600 mL) and brine (600 mL) before being dried over sodium sulfate, filtered and concentrated to afford crude 68 (13.5 g) in the form of a purple oil. 68 was engaged in the next step without further purification.

Synthesis of Compound 69

$C_{13}H_{16}F_2O_6$ M=306.26 g·mol⁻¹

¹⁹F NMR (D₂O, 282.5 MHz): −107.6 (brd, J=262 Hz, 1F, CFF); −111.6 (brdd, J1=262 Hz, J2=31 Hz, 1F, CFF).

Mass (ESI−): 285.1 (M−H—HF)⁻; 305.1 (M−H)⁻, 341.1 (M+Cl)⁻; 351.1 (M+HCO₂)⁻

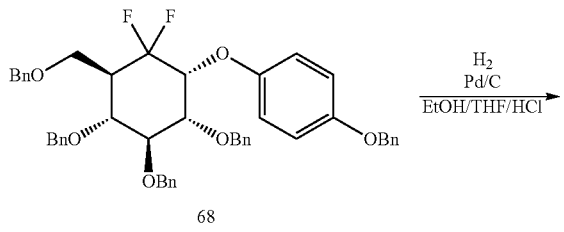

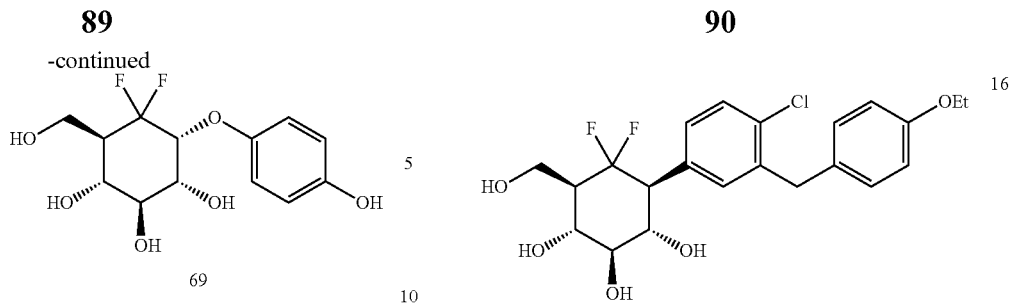

69

Crude 68 (13.5 g) was dissolved in a mixture of ethanol/12N HCl 4% (v/v, 117 mL), tetrahydrofurane (63 mL). Palladium on activated carbon (10%, 3.8 g, 0.2 eq.) was then suspended in the solution and the reaction mixture was placed under hydrogen atmosphere and stirred for 3 days at room temperature. The reaction medium was filtered and concentrated before being purified on silica gel chromatography (dichloromethane/methanol 100:0 to 85:15, v/v on Biotage SNAP 340 g cartridge) to afford 69 (4.92 g, 90%) which was freeze-dried in the form of a white solid.

2. Biological Activity a) Assay for the Facilitatory Effect on Glucose Excretion.

As experimental animal, female CD1 mice (CDM or Charles River) were used. A test compound was dissolved in the vehicle (5% N-methyl pyrrolidone, 20% PEG 400, 75% 20 mM $Na_4P_2O_7$ buffer, v/v/v) at the concentration of 1 mg/mL After the body weights of the mice were measured and the mice randomized, the test article was orally administered at the dose of 1 mg/kg, 3 mg/kg and 10 mg/kg. For control, just the vehicle (5% N-methyl pyrrolidone, 20% PEG 400, 75% 20 mM $Na_4P_2O_7$ buffer, v/v/v) was orally administered. The oral administration was performed with gastric tube for mice and a 1 mL syringe. The minimum count in one group was 3 but could reach 12 for some groups. Collection of the urine was performed manually by gentling massaging the abdomen in order to collect urine (3 µL) via a calibrated pipette. Urine was collected at 1, 2, 4, 6, 8 and then 16, 18, 20, 22, 24, 26 and 28 hrs. The urine glucose concentration was measured using a WAKO glucose kit as follows: 3 µL of urine was deposited into a 96-well micro plate for spectrometric readout. The urine aliquot was diluted with 350 µL of the WAKO working solution. For glucose concentrations that may be over the range of the WAKO glucose kit, an aliquot (35 µL) of the last solution was deposited into another 96-well micro plate and further diluted (10×) with 315 µL of the WAKO working solution. The absorbance of the 96-well plates were then read at 505 nm using a BioTek SynergyMX plate fluorometer/absorbance photometer and the glucose concentration was calculated. The glucose concentrations for controls and test articles at the different time points were averaged using Excel 2007 and plotted using GraphPad Prism 5.

Figure 1:
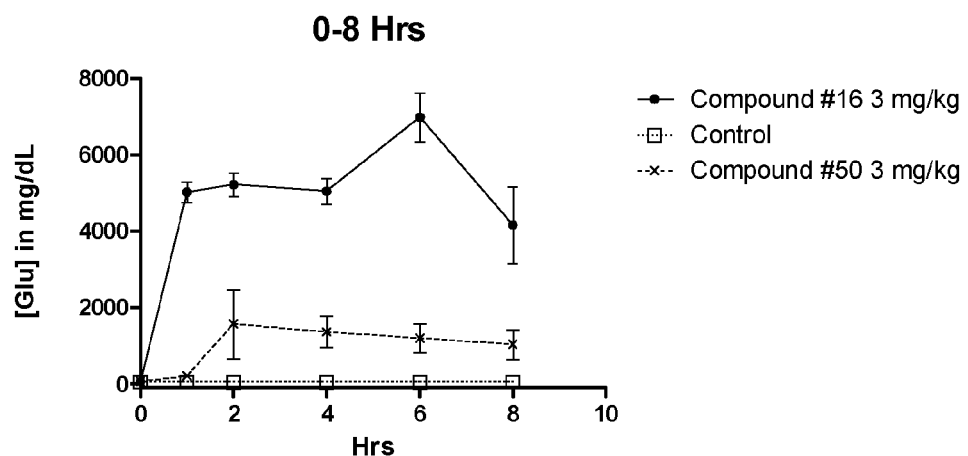
Figure 2:
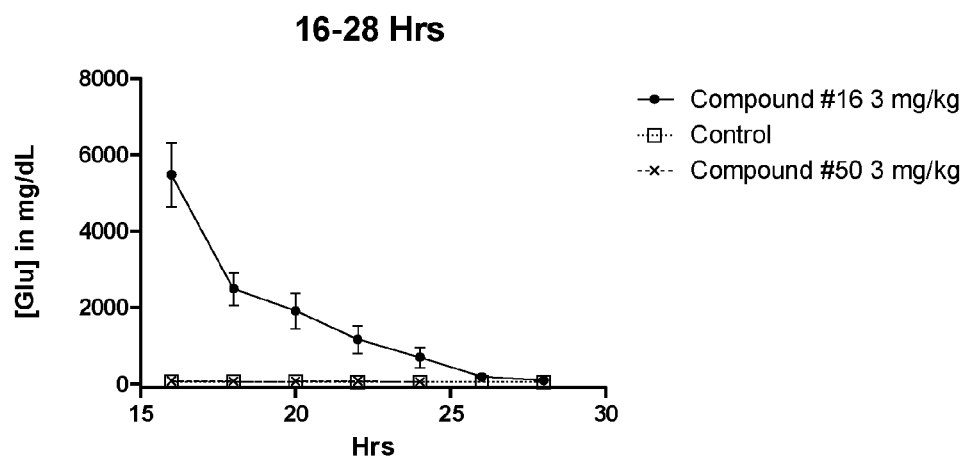

The results obtained with 16 and 50 are shown on FIGS. 1 and 2. It appears thus that 16 (3 mg/kg) triggered a lasting glucosuria (up to 26 hrs, FIG. 2).

b) Assays to Compare the Duration of Action of Compounds According to the Invention to the One of Compounds of Prior Art by Studying the Facilitatory Effect on Glucose Excretion The assays have been performed as described for a).

Compound 16 according to the invention has been compared to Dapaglifozin to underline the improvement of the duration of action, i.e. the longer duration of glucosuria, of the compound when the intracyclic oxygen atom of the glucose moiety is replaced by a $CF_2$ moiety.

This assay has been carried out at a dose of 3 mg/kg.

The results obtained are presented on FIG. 5. It appears thus that 16 (3 mg/kg) triggered glucosuria that lasted beyond 24 hours compared to Dapagliflozin.

Compound 16 according to the invention has been compared to the compound 9 of WO 2009/1076550 to underline the improvement of the duration of action of the compound when a mimic of glucose bearing a CH—OH moiety instead of the intracyclic oxygen atom is replaced by a mimic of glucose bearing a $CF_2$ in place of the CH—OH moiety.

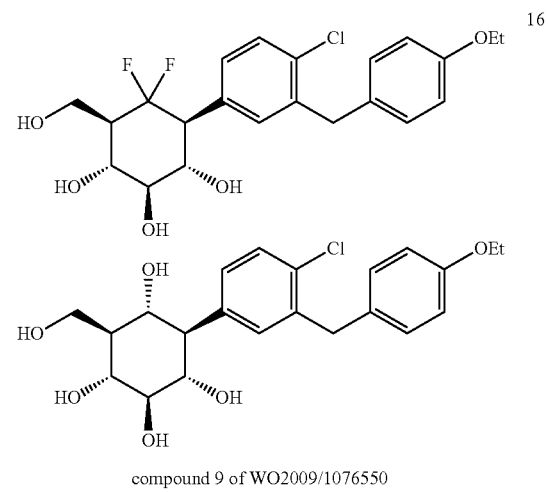

compound 9 of WO2009/1076550

This assay has been carried out at a dose of 3 mg/kg.

The results obtained are presented on FIG. 6. It appears thus that 16 (3 mg/kg) triggered a longer lasting glucosuria (up to 24 hrs) when none could be detected for the same time period for the compound 9 of WO 2009/1076550.

c) Assay for the Facilitatory Effect in Decreasing Blood Glucose Excursions Following Glucose Challenge.

As experimental animal, 18 hrs fasted female CD1 mice (CDM or Charles River) were used. A test compound was dissolved in the vehicle (5% N-methyl pyrrolidone, 20% PEG 400, 75% 20 mM $Na_4P_2O_7$ buffer, v/v/v) at the concentration of 1 mg/mL. After the body weights of the mice were measured and the mice randomized, the test article was orally administered at the dose of 1 mg/kg, 3 mg/kg and 10 mg/kg. For control, just the vehicle (5% N-methyl pyrrolidone, 20% PEG 400, 75% 20 mM $Na_4P_2O_7$ buffer, v/v/v) was orally administered. 15 min after this oral administration, a 20% glucose solution in deionised water was orally administered to all mice. The oral administration was performed with gastric tube for mice and a 1 mL syringe. The minimum count in one group was 3 but could reach 5 for some groups. Collection of the blood was performed via the saphenous vein. Blood was collected at 5, 10, 30, 45, 60 and 120 min post glucose challenge. One experiment consisted in administrating the test article 18 hrs prior to a glucose challenge i.e. 18 hrs post po of test article. The blood glucose concentration was measured using Johnson and Johnson's OneTouch® Ultra Blood Glucose Monitoring System. The glucose concentrations for controls and test articles at the different time points were averaged using Excel 2007 and plotted using GraphPad Prism 5.

Figure 3:
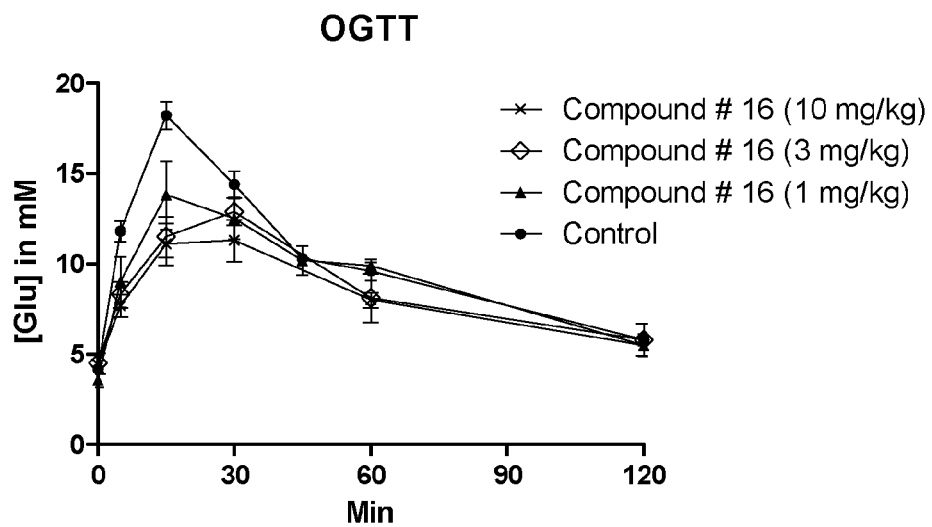
FIG. 3 represents oral glucose tolerance test for compound 16 at 1, 3 and 10 mg/kg po.
Figure 4:
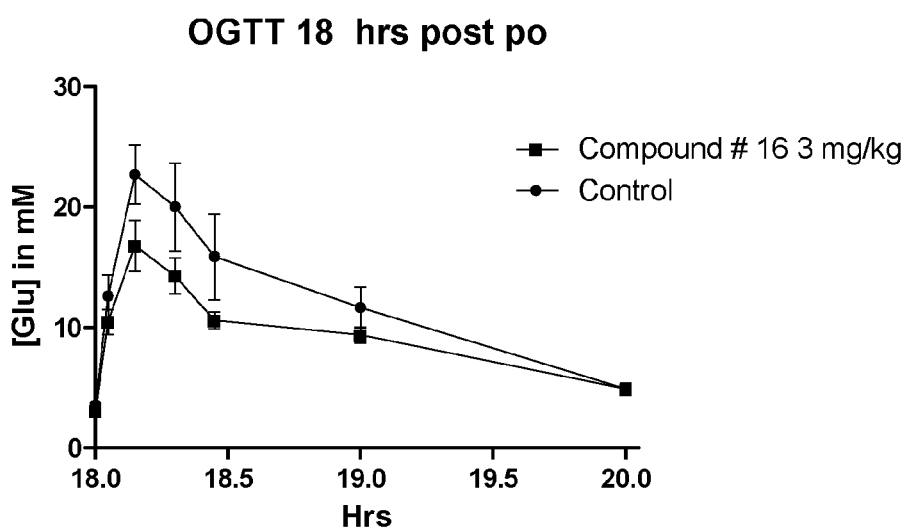
FIG. 4 represents oral glucose tolerance test for compound 16 18 hours post oral administration of compound 16 (3 mg/kg po).

The results obtained with 16 are shown on FIGS. 3 and 4.

It appears thus that 16 reduced blood glucose levels in a dose-dependent manner in normal mice following glucose challenge (FIG. 3). Moreover, 16 (3 mg/kg) administered orally 18 hrs prior to glucose challenge still reduced blood glucose excursions following glucose challenge (FIG. 4).

d) Assay to Evaluate and Compare the Stability Against Glycosidase of Compound 26 According to the Invention to a Compound of Prior Art (Sergliflozin-A).

The enzymatic stability assay has been performed with compound 26 according to the invention and compound A used as a reference compound to control the efficacy of the β-glucosidase. The sergliflozin-A stability has also been evaluated in order to compare the improvement of metabolic stability obtained through the replacement of the intracyclic oxygen atom of the glucose moiety by a $CF_2$ moiety.

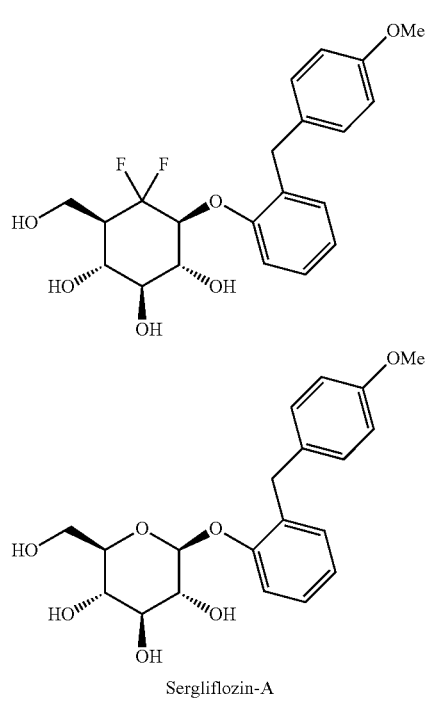

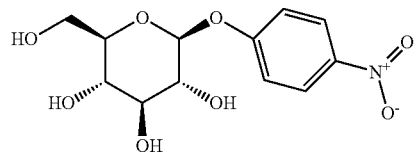

All the compounds have been treated with β-glucosidase. The stability of compound 26 and Sergliflozin-A has been assessed by HPLC analysis after incubation with β-glucosidase.

A Gilson HPLC system was used, equipped with a manual injection system (V=20 μL), a Diode Array Detector (DAD172) set at a wavelength of 230 nm and a 150 mm×4.6 mm, 5 μm HICHROM Kromasil 100-5C18 reverse phase column. A linear HPLC binary gradient was used as follows: solvent A was water and solvent B was acetonitrile. Following the injection of 20 μL of a sample, solvent B was held at 20% for 3 min, increased from 20% to 90% in 17 min, held at 90% for 4 min; finally, solvent B was decreased back to 20% over 5.5 min and was held at 20% for 3.5 min.

The procedure has been adapted from J. Agric. Food Chem. 2005, 53, 4918-4924.

100 μL of a solution of compound 26 at $4.5 \cdot 10^{-4}$ mol·$L^{-1}$ in acetonitrile was added to a solution containing 800 μL of phosphate buffer (73173 Fluka, pH 7) in the presence of β-glucosidase from Almonds (10 U, 100 μL of a 5.6 mg·$mL^{-1}$ solution in phosphate buffer, (G4511sigma 18.7 U per mg)) and was kept 4 h at 37° C.

100 μL of a solution of sergliflozin-A at $4.5 \cdot 10^{-4}$ mol·$L^{-1}$ in acetonitrile has been treated in the presence of β-glucosidase following the same process.

In parallel, 100 μL of a solution of p-nitrophenyl-β-glucoside (compound A) at $4.5 \cdot 10^{-4}$ mol·$L^{-1}$ in phosphate buffer (73173 Fluka, pH 7) was added to a solution containing 700 μL of phosphate buffer and 100 μL of acetonitrile, with the presence of β-glucosidase from Almonds (10 U, 100 μL of a 5.6 mg·$mL^{-1}$ solution in phosphate buffer, (G4511 sigma 18.7 U per mg)) and was kept 4 h at 37° C. During the process in the presence of β-glucosidase, a yellow coloration was observed that underlines the decomposition of compound. A.

Sergliflozin A as referred in several publications (*Discov. Med.* 2011, (58): 255-263; *Nature Reviews Drug Discovery* 2010, 9, 551-559) is known to undergo cleavage by β-glucosidase.

HPLC of compound 21 (FIG. 7), compound 26 (FIG. 8) and Sergliflozin-A (FIG. 10) have been performed to follow up in the experiments the formation of compound 21 (the aglycone part) implying a degradation of the starting material.

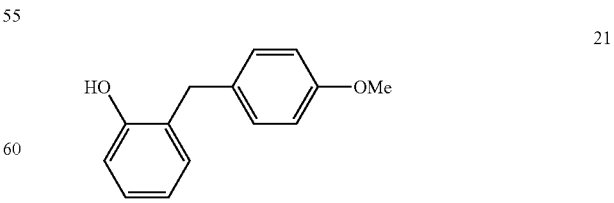

HPLC of compound 26 in the presence of β-glucosidase has been performed (FIG. 9) and underlines that no degradation occurs as the formation of compound 21 was not observed.

HPLC of Sergliflozin-A in the presence of β-glucosidase has been performed (FIG. 11) and underlines that degradation occurs as the formation of compound 21 was observed. In order to evaluate the percentage of degradation, a calibration has been done on compound 21 giving the following results:

| Concentration g/L | Area % |
|---|---|
| 0.005 | 260 |
| 0.01 | 506 |
| 0.05 | 2962 |
| 0.1 | 5226 |

Data have been plotted (Area % versus concentration) and the linear regression obtained was characterized by the equation y=53629x and a $R^2$=0.994.

In FIG. 11, the HPLC spectrum of Sergliflozin-A in the presence of β-glucosidase underlines that degradation occurs with the formation of compound 21 (Area %=416).

The previous equation allows us to determine that the concentration of compound 21 is $7.76 \cdot 10^{-3}$ g/L, which corresponds to $3.6 \cdot 10^{-8}$ mol.

This equals to 80% of degradation for Sergliflozin-A after 4 h of incubation at 37° C. with β-glucosidase, while no degradation occurs for Compound 26 in the same condition.

e) Assay for the Inhibition of Tyrosine-Tyrosinase Reaction

Inhibition of tyrosinase, i.e. inhibition of the hydroxylation of Tyrosine into DOPA, was measured by visible spectrophotometry, and more specifically by measuring the absorbance at 477 nm, indicative of the amount of melanine produced in vitro from the Tyrosine substrate by Tyrosinase.

In order to make sure that the measured absorbance is proportional to the enzymatic activity in the range of studied concentrations, five standard solutions were prepared as follows.

| Standard solution # | Solution A | Bis Tris buffer | Solution B | milliQ water QS | Absorbance (477 nm) |
|---|---|---|---|---|---|
| 1 | 0 mL | 2 mL | 2 mL | 10 mL | 0.0002 |
| 2 | 2 mL | 2 mL | 2 mL | 10 mL | 0.2626 |
| 3 | 4 mL | 2 mL | 2 mL | 10 mL | 0.4832 |
| 4 | 6 mL | 2 mL | 2 mL | 10 mL | 0.5774 |
| 5 | 8 mL | 2 mL | 2 mL | 10 mL | 0.5447 |

Absorbance has been measured on a Perkin Elmer UV/Vis Spectrometer Lambda 12.

Solution A (1,000 U/mL mother solution of Tyrosinase) was prepared by dissolving 40 mg of 1,250 U/mg Mushroom Tyrosinase in 1 mL 100 mM pH6.5 bis Tris buffer and QS to 50 mL with milliQ water.

Bis Tris buffer (100 mM pH6.5 bis Tris buffer) was prepared by dissolving 2.09 g of Bis Tris in milliQ water and QS to 100 mL.

Solution B (mother solution of Tyrosine) was prepared by dissolving 100 mg of Tyrosine in milliQ water and QS to 100 mL.

The standard solutions were incubated for 2 h at 37° C., then quickly cooled to 4° C. The absorbance of the solutions #2-5 was measured at 477 nm against the blank solution free of Tyrosinase (solution #1). Data have been graphed (absorbance versus Tyrosinase concentration) and the straight line obtained, in the range of absorbance from 0 to 0.5, was characterized by the equation y=0.2415x−0.2343 and a $R^2$=0.9975.

The following test solutions were prepared and their absorbance was measured at 477 nm:

| | Solution C | Solution D Description | Solution E |
|---|---|---|---|
| | Witness Solution (100% of Tyrosinase activity) | Compound 31 (n = $5 \cdot 10^{-5}$ mol) | Hydroquinone (n = $5 \cdot 10^{-5}$ mol) |
| Test compound (mg) | 0 | 15.3 | 5.5 |
| Solution A (mL) | 1 | 1 | 1 |
| Solution B (mL) | 0.5 | 0.5 | 0.5 |
| Bis Tris buffer (mL) | 0.5 | 0.5 | 0.5 |
| Absorbance (477 nm) | 0.4354 | 0.1292 | 0.1528 |

With an absorbance of 0.1292, compound 31 (solution D) shows an inhibition of tyrosinase as hydroquinone (solution E).

f) Assay to Evaluate and to Compare the IC50 of Compound 31 According to the Invention to a Compound of Prior Art (β-Arbutin).

The protocol performed is the same as in assay e.

Solution A (1,000 U/mL mother solution of Tyrosinase) was prepared by dissolving all of 50 kU Mushroom Tyrosinase in 1 mL 100 mM pH6.5 bis Tris buffer and QS to 50 mL with milliQ water.

Bis Tris buffer (100 mM pH6.5 bis Tris buffer) was prepared by dissolving 2.09 g of Bis Tris in milliQ water and QS to 100 mL. pH was adjusted at 6.5 using hydrochloric acid.

Solution B (mother solution of Tyrosine) was prepared by dissolving 20 mg of Tyrosine in milliQ water and QS to 20 mL.

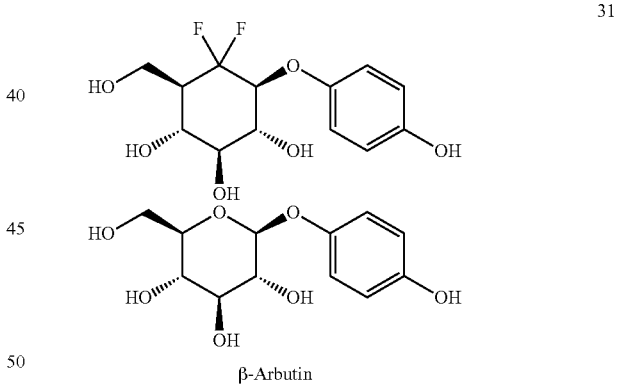

β-Arbutin

Stock solution of compound 31 was prepared as follow: 10 mg of compound 31 was dissolved in Bis Tris buffer up to 1 ml.

Stock solution of β-arbutin was prepared as follow: 20 mg of compound β-arbutin was dissolved in Bis Tris buffer up to 1 ml.

The solutions were incubated for 1 h 30 at 37° C., then quickly cooled to 4° C. 100 µL of each solution were deposited on 96-well plate. The absorbance of the different solutions were measured at 477 nm (Molecular Devices: Spectra Max 340PC).

The different solutions were prepared as described in the different tables below and their absorbances were reported. The absorbance of witness solution (without inhibitor) was set at 100% of enzymatic activity, allowing us to determine the percentage of enzymatic activity of the different solutions.

|  | Entry 1 | Entry 2 | Entry 3 | Entry 4 | Entry 5 | Witness |
|---|---|---|---|---|---|---|
| Solution B (μL) | 50 | 50 | 50 | 50 | 50 | 50 |
| Solution of compound 31 (μL) | 10 | 20 | 30 | 50 | 60 | 0 |
| Water (μL) | 240 | 230 | 220 | 200 | 190 | 250 |
| Solution A(μL) | 30 | 30 | 30 | 30 | 30 | 30 |
| Absorbance (477 nm) | 0.5855 | 0.3535 | 0.255 | 0.220 | 0.200 | 0.718 |
| Inhibitor Concentration mg/mL | 0.17 | 0.33 | 0.50 | 0.67 | 0.83 | 0.00 |
| % activity | 81.55 | 49.23 | 35.52 | 30.57 | 27.86 | 100.00 |

|  | Entry 1 | Entry 2 | Entry 3 | Entry 4 | Entry 5 | Witness |
|---|---|---|---|---|---|---|
| Solution B (μL) | 50 | 50 | 50 | 50 | 50 | 50 |
| Solution of β-Arbutin (μL) | 10 | 20 | 30 | 40 | 50 | 0 |
| Water (μL) | 210 | 200 | 190 | 180 | 170 | 220 |
| Solution A(μL) | 30 | 30 | 30 | 30 | 30 | 30 |
| Absorbance (477 nm) | 0.5010 | 0.3040 | 0.2380 | 0.2035 | 0.1970 | 0.722 |
| Inhibitor Concentration mg/mL | 0.67 | 1.33 | 2.00 | 2.67 | 3.33 | 0.00 |
| % activity | 66.62 | 40.43 | 31.65 | 27.06 | 26.20 | 100.00 |

Data have been plotted (% of activity versus concentration of inhibitors) and the linear regression of the curve was used to calculate the 1050 of both compounds. The results obtained are presented in the table below:

|  | Concentration Tyrosinase 100 U/mL |  |
|---|---|---|
| IC50 | Compound 31 | 0.328 mg/mL |
|  | ☐☐Arbutin | 1.1 mg/mL |

The results clearly underline that compound 31 is a better tyrosinase inhibitor than β-Arbutin.

The invention claimed is:

1. A compound having the following formula (I):

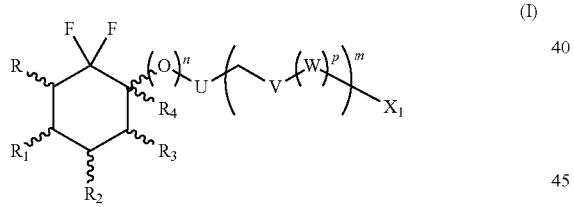

(I)

or a pharmaceutically or cosmetically acceptable salt thereof, or a tautomer, or a stereoisomer or a mixture of stereoisomers, wherein:

n=1 and m=0, p=0,

R is $CH_2OH$, $R_1$, $R_2$ and $R_3$ are OH, $R_4$ is a hydrogen atom, $X_1$ is a hydrogen atom, an halogen atom, OH, $(C_1-C_6)$-alkyl, $OR^{24}$, or $OCOR^{24}$, U is a phenyl ring, said ring being optionally substituted with one or more substituents selected from the group consisting of an halogen atom, OH, $(C_1-C_6)$-alkyl, $OR^{24}$, and $OCOR^{24}$, and $R^{24}$ is a $(C_1-C_6)$-alkyl.

2. The compound according to claim 1, having the following formula (I-1), (I-1), (I-1b) or (I-1c):

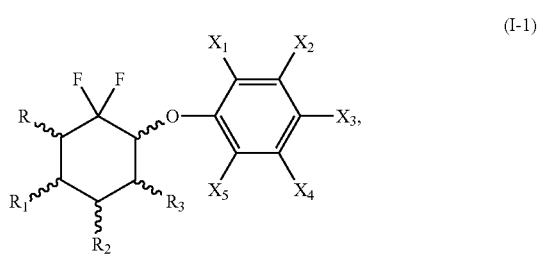

(I-1)

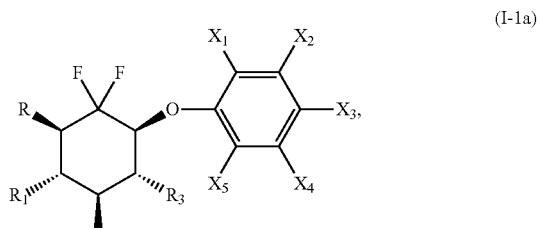

(I-1a)

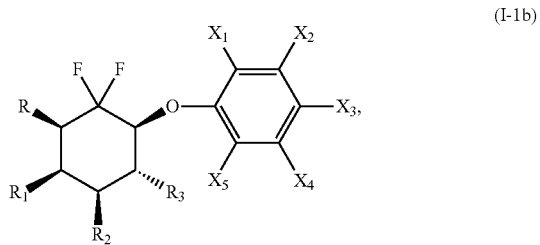

(I-1b)

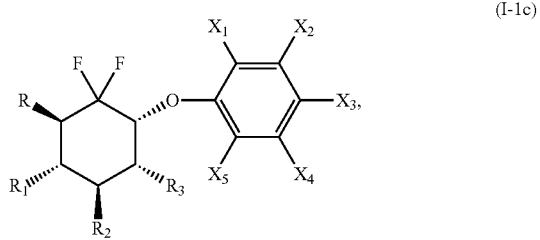

(I-1c)

or a pharmaceutically or cosmetically acceptable salt thereof, a tautomer, a stereoisomer or a mixture of stereoisomers, wherein:

X$_1$, X$_2$, X$_3$, X$_4$ and X$_5$ are, independently from one another, a hydrogen atom, an halogen atom, OH, (C$_1$-C$_6$)-alkyl, OR$^{24}$, or OCOR$^{24}$.

3. The compound according to claim 1, wherein U is a phenyl ring, said ring being optionally substituted with one or more substituents selected from the group consisting of an halogen atom, OH, (C$_1$-C$_6$)-alkyl, and OR$^{24}$, and X$_1$ is selected from the group consisting of a hydrogen atom, a halogen atom, OH, (C$_1$-C$_6$)-alkyl, and OR$^{24}$.

4. The compound according to claim 1, selected from:

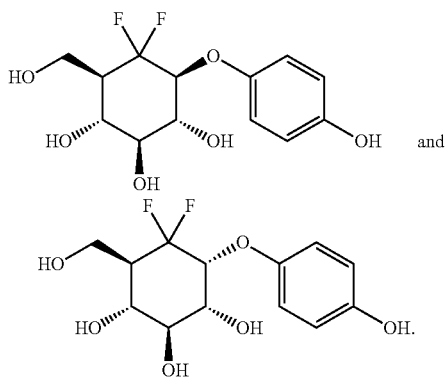

5. The compound according to claim 2, wherein X$_1$, X$_2$, X$_3$, X$_4$ and X$_5$ are, independently from one another, a hydrogen atom, an halogen atom, OH, (C$_1$-C$_6$)-alkyl or OR$^{24}$.

6. The compound according to claim 2, wherein X$_1$, X$_2$, X$_3$, X$_4$ and X$_5$ are, independently from one another, a hydrogen atom, an halogen atom, OH, or OR$^{24}$.

7. The compound according to claim 3, wherein U is a phenyl ring, said ring being optionally substituted with one or more substituents selected from the group consisting of an halogen atom, OH, and OR$^{24}$, and X$_1$ is selected from the group consisting of a hydrogen atom, a halogen atom, OH, and OR$^{24}$.

8. A method for lightening, bleaching, depigmenting the skin, or removing blemishes from the skin, comprising the topical application of at least one compound according to claim 1.

9. The method according to claim 8, wherein the blemishes of the skin are age spots or freckles.

10. A pharmaceutical or cosmetic composition including at least one compound according to claim 1 and at least one pharmaceutically or cosmetically acceptable vehicle.

11. A compound of following formula:

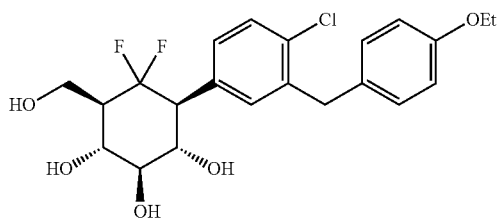 [SMILES: CCOc1ccc(Cc2cc([C@H]3[C@H](O)[C@@H](O)[C@H](O)[C@@H](CO)C3(F)F)ccc2Cl)cc1]

or a pharmaceutically or cosmetically acceptable salt thereof.

12. A method for inhibiting a sodium-dependent glucose co-transporter comprising the administration to a person in need thereof of an effective amount of a compound according to claim 11.

13. The method according to claim 12, wherein the sodium-dependent glucose co-transporter is SGLT1, SGLT2 or SGLT3.

14. A method for treating diabetes; diabetes-related complications selected from the group consisting of arteritis of the lower extremities, cardiac infarction, renal insufficiency, neuropathy and blindness; hyperglycemia; hyperinsulinemia; obesity; hypertriglyceridemia; X syndrome; or arteriosclerosis, or for an anti-cancer, anti-infective, anti-viral, anti-thrombotic or anti-inflammatory treatment, including the administration of an effective amount of at least one compound according to claim 11 to a patient in need thereof.

15. The method according to claim 14, wherein the method is for treating type-II diabetes, arteritis of the lower extremities, cardiac infarction, renal insufficiency, neuropathy or blindness.

16. A pharmaceutical or cosmetic composition including at least one compound according to claim 11 and at least one pharmaceutically or cosmetically acceptable vehicle.

* * * * *

UNITED STATES PATENT AND TRADEMARK OFFICE
CERTIFICATE OF CORRECTION

| | | |
|---|---|---|
| PATENT NO. | : 9,434,670 B2 | Page 1 of 1 |
| APPLICATION NO. | : 14/119265 | |
| DATED | : September 6, 2016 | |
| INVENTOR(S) | : Geraldine Deliencourt-Godefroy and Lenaig Lopes | |

It is certified that error appears in the above-identified patent and that said Letters Patent is hereby corrected as shown below:

In the Specification

Column 35, Line 55, "compound no." should be --compound T30.--.

Column 42, Line 4, "compound M." should be --compound 21.--.

Column 71, ". " should be -- 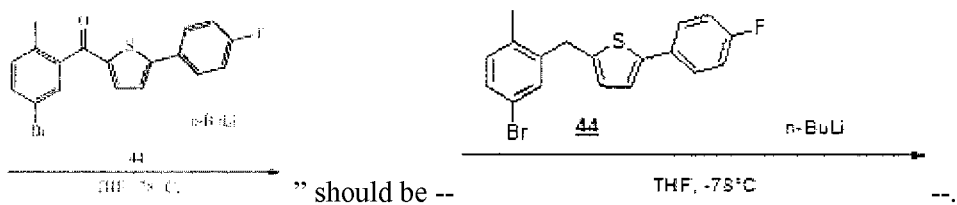 --.

Column 78, Line 35, after "Synthesis of Compound 56" insert on the next line:
--$C_{37}H_{38}O_7$    $M=594.69 g.mol^{-1}$--.

Column 94, the lower portion of header of the table at Line 9 should read as follows:

| Description | Witness-Solution (100% of Tyrosinase activity) | Compound 31 ($n=5.10^{-5}$ mol) | Hydroquinone ($n=5.10^{-5}$ mol) |
|---|---|---|---|

In the Claims

Column 96, Claim 2, Line 21, "(I-1), (I-1), (I-1b)" should be --"(I-1), (I-1a), (I-1b)--.

Signed and Sealed this
Fourteenth Day of November, 2017

Joseph Matal
*Performing the Functions and Duties of the
Under Secretary of Commerce for Intellectual Property and
Director of the United States Patent and Trademark Office*